United States Patent
Jensen et al.

(10) Patent No.: US 11,130,775 B2
(45) Date of Patent: Sep. 28, 2021

(54) SOLID FORMS OF (2S,3S,4S,5R,6S)-3,4,5-TRIHYDROXY-6-(((4AR,10AR)-7-HYDROXY-1-PROPYL-1,2,3,4,4A,5,10,10A-OCTAHYDROBENZO[G]QUINOLIN-6-YL)OXY)TETRAHYDRO-2H-PYRAN-2-CARBOXYLIC ACID

(71) Applicant: H. Lundbeck A/S, Valby (DK)

(72) Inventors: Klaus Gjervig Jensen, Valby (DK); Lisbet Kværnø, Valby (DK); Morten Jørgensen, Valby (DK); Martin Juhl, Valby (DK); Heidi Lopez de Diego, Valby (DK); Karin Fredholt, Valby (DK); Frans Dennis Therkelsen, Valby (DK); Tobias Gylling Frihed, Valby (DK); Mikkel Fog Jacobsen, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/876,908

(22) Filed: May 18, 2020

(65) Prior Publication Data
US 2020/0392176 A1 Dec. 17, 2020

(30) Foreign Application Priority Data

May 20, 2019 (DK) .............................. PA201900598
May 20, 2019 (DK) .............................. PA201900599
May 21, 2019 (DK) .............................. PA201900612
May 24, 2019 (DK) .............................. PA201900636

(51) Int. Cl.
*C07H 15/26* (2006.01)

(52) U.S. Cl.
CPC .......... *C07H 15/26* (2013.01); *C07B 2200/13* (2013.01)

(58) Field of Classification Search
None
See application file for complete search history.

(56) References Cited

U.S. PATENT DOCUMENTS

| | | |
|---|---|---|
| 4,543,256 A | 9/1985 | Neumeyer |
| 4,565,818 A | 1/1986 | Nordmann et al. |
| 4,692,453 A | 9/1987 | Seiler |
| 5,747,513 A | 5/1998 | Montanari et al. |
| 5,885,988 A | 3/1999 | Neumann et al. |
| 5,955,468 A | 9/1999 | Markstein |
| 8,129,530 B2 | 3/2012 | Jorgensen et al. |
| 10,729,710 B2 * | 8/2020 | Jensen ................ A61K 31/473 |
| 2009/0062324 A1 | 3/2009 | Jorgensen et al. |
| 2012/0077836 A1 | 3/2012 | Wilkstrom et al. |
| 2017/0335357 A1 | 11/2017 | Divi et al. |
| 2020/0338102 A1 | 1/2020 | Balmer et al. |
| 2020/0369615 A1 | 11/2020 | Jacobsen et al. |
| 2020/0369705 A1 | 11/2020 | Juhl et al. |
| 2020/0369706 A1 | 11/2020 | Juhl et al. |

FOREIGN PATENT DOCUMENTS

| | | |
|---|---|---|
| CN | 102746351 A | 10/2012 |
| CN | 105218606 A | 1/2016 |
| GB | 2 192 394 A | 1/1998 |
| JP | S60-172975 A | 9/1985 |
| WO | 90/12574 A1 | 11/1990 |
| WO | WO 97/03054 A1 | 1/1997 |
| WO | 98/38155 A1 | 9/1998 |
| WO | WO 00/47571 A1 | 8/2000 |
| WO | WO 01/36428 A1 | 5/2001 |
| WO | WO 01/76602 A1 | 10/2001 |
| WO | WO 2001/078713 A1 | 10/2001 |
| WO | 02/13827 A1 | 2/2002 |
| WO | WO 2002/100377 A1 | 12/2002 |
| WO | WO 03/006458 A1 | 1/2003 |
| WO | 03/013532 A1 | 2/2003 |
| WO | WO 03/074511 A1 | 9/2003 |
| WO | WO 03/080074 A1 | 10/2003 |
| WO | 2005/062894 A2 | 7/2005 |
| WO | 2006/012640 A2 | 2/2006 |

(Continued)

OTHER PUBLICATIONS

Morissette, Advanced Drug Delivery Reviews 56 (2004) 275-300. (Year: 2004).*
PCT/EP2020/063910, dated Jul. 14, 2020, International Search Report and Written Opinion.
International Search Report and Written Opinion dated Jul. 14, 2020 in connection with Application No. PCT/EP2020/063910.
Alexander et al., Functional architecture of basal ganglia circuits: neural substrates of parallel processing. Trends Neurosci. Jul. 1990;13(7):266-71. doi: 10.1016/0166-2236(90)90107-1.
Bibbiani et al., Continuous dopaminergic stimulation reduces risk of motor complications in parkinsonian primates. Exp Neurol. Mar. 2005;192(1):73-8. doi: 10.1016/j.expneurol.2004.11.013.

(Continued)

*Primary Examiner* — Layla D Berry
(74) *Attorney, Agent, or Firm* — Wolf, Greenfield & Sacks, P.C.

(57) ABSTRACT

The present invention relates to new solid forms of the compound (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid with the formula (Id) below.

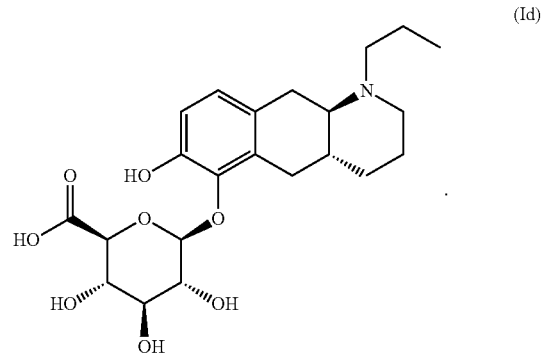

The compound of formula (Id) is a prodrug of a catecholamine for use in treatment of neurodegenerative diseases and disorders such as Parkinson's Disease.

16 Claims, 21 Drawing Sheets

(56) References Cited

FOREIGN PATENT DOCUMENTS

| WO | WO 2006/056604 A1 | 6/2006 | |
|---|---|---|---|
| WO | WO 2009/026934 A1 | 3/2009 | |
| WO | WO 2009/026935 A1 | 3/2009 | |
| WO | WO 2010/097092 A1 | 9/2010 | |
| WO | 2013/020979 A1 | 2/2013 | |
| WO | WO 2013/034119 A1 | 3/2013 | |
| WO | WO 2015/067927 A1 | 5/2015 | |
| WO | WO 2017/184871 A1 | 10/2017 | |
| WO | WO 2019/101917 A1 | 5/2019 | |
| WO | WO-2019101917 A1 * | 5/2019 | ........... C07D 405/12 |

OTHER PUBLICATIONS

Campbell et al., Behavioral effects of (−)10,11-methylenedioxy-N-n-propylnoraporphine, an orally effective long-acting agent active at central dopamine receptors, and analogous aporphines. Neuropharmacology. Oct. 1982;21(10):953-61. doi: 10.1016/0028-3908(82)90106-x.

Cannon et al., N?Alkyl derivatives of trans?6, 7?dihydroxy?1, 2, 3, 4, 4a, 5, 10, 10b?octahyrobenzo [g] quinoline A congener of apomorphine lacking the non?oxygenated aromatic ring. J Heterocycl Chem. Nov. 1980;17(7):1633-6.

Cavero et al., Safety Pharmacology assessment of drugs with biased 5-HT(2B) receptor agonism mediating cardiac valvulopathy. J Pharmacol Toxicol Methods. Mar.-Apr. 2014;69(2):150-61. doi: 10.1016/j.vascn.2013.12.004. Epub Dec. 19, 2013.

Delong et al., Primate models of movement disorders of basal ganglia origin. Trends Neurosci. Jul. 1990;13(7):281-5. doi: 10.1016/0166-2236(90)90110-v.

Gerfen et al., D1 and D2 dopamine receptor-regulated gene expression of striatonigral and striatopallidal neurons. Science. Dec. 7, 1990;250(4986):1429-32. doi: 10.1126/science.2147780.

Giardina et al., Adrogolide HCl (ABT-431; DAS-431), a prodrug of the dopamine D1 receptor agonist, A-86929: preclinical pharmacology and clinical data. CNS Drug Rev. 2001 Fall;7(3):305-16. doi: 10.1111/j.1527-3458.2001.tb00201.x.

Goswami et al., Intestinal absorption and metabolism of retinoyl beta-glucuronide in humans, and of 15-[14C]-retinoyl beta-glucuronide in rats of different vitamin A status. J Nutr Biochem. Dec. 2003;14(12):703-9. doi: 10.1016/j.jnutbio.2003.08.008.

Grosset et al., Inhaled dry powder apomorphine (VR040) for 'off' periods in Parkinson's disease: an in-clinic double-blind dose ranging study. Acta Neurol Scand. Sep. 2013;128(3):166-71. doi: 10.1111/ane.12107. Epub Mar. 26, 2013.

Hauser et al., Sublingual apomorphine (APL-130277) for the acute conversion of OFF to ON in Parkinson's disease. Mov Disord. Sep. 2016;31(9):1366-72. doi: 10.1002/mds.26697. Epub Jul. 19, 2016.

Liu et al., A novel synthesis and pharmacological evaluation of a potential dopamine D1/D2 agonist: 1-propyl-1,2,3,4,4a,5,10,10a-octahydrobenzo[g]quinoline-6,7-diol. Bioorg Med Chem. Mar. 15, 2008;16(6):3438-44. doi: 10.1016/j.bmc.2007.06.036. Epub Jun. 23, 2007.

Liu et al., Extremely potent orally active benzo[g]quinoline analogue of the dopaminergic prodrug: 1-propyl-trans-2,3,4,4a,5,7,8,9,10,10a-decahydro-1H-benzo-[g]quinolin-6-one [corrected]. J Med Chem. Feb. 23, 2006;49(4):1494-8. doi: 10.1021/jm051111h.

Loozen et al., An approach to the synthesis of [2] benzopyrano [3, 4?c] pyrroles; alternative dopaminergic molecules. Recueil des Travaux Chimiques des Pays?Bas. 1982;101(9):298-310.

Nolen et al., Budesonide-beta-D-glucuronide: a potential prodrug for treatment of ulcerative colitis. J Pharm Sci. Jun. 1995;84(6):677-81. doi: 10.1002/jps.2600840603.

Poewe et al., Parkinson disease. Nat Rev Dis Primers. Mar. 23, 2017;3:17013. doi: 10.1038/nrdp.2017.13.

Rothman et al., Evidence for possible involvement of 5-HT(2B) receptors in the cardiac valvulopathy associated with fenfluramine and other serotonergic medications. Circulation. Dec. 5, 2000;102(23):2836-41. doi: 10.1161/01.cir.102.23.2836.

Sozio et al., Designing prodrugs for the treatment of Parkinson's disease. Expert Opin Drug Discov. May 2012;7(5):385-406. doi: 10.1517/17460441.2012.677025. Epub Apr. 12, 2012.

Sprenger et al., Management of motor and non-motor symptoms in Parkinson's disease. CNS Drugs. Apr. 2013;27(4):259-72. doi: 10.1007/s40263-013-0053-2.

Stain-Texier et al., Intestinal absorption and stability of morphine 6-glucuronide in different physiological compartments of the rat. Drug Metab Dispos. May 1998;26(5):383-7.

U.S. Appl. No. 16/198,917, filed Nov 23, 2018, Granted, U.S. Pat. No. 10,729,710[2].

U.S. Appl. No. 16/872,802, filed May 12, 2020, Allowed, 2020-0338102[1].

U.S. Appl. No. 16/876,843, filed May 18, 2020, Allowed, 2020-0369705[1].

U.S. Appl. No. 16/876,878, filed May 18, 2020 Published, 2020-0369706[1].

U.S. Appl. No. 16/876,966, filed May 18, 2020, Published, 2020-0369615[1].

PCT/EP2018/082361, dated Feb 22, 2019, International Search Report and Written Opinion.

PCT/EP2020/063909, dated Jul. 2, 2020, International Search Report and Written Opinion.

PCT/EP2020/063913, dated Jul. 15, 2020, International Search Report and Written Opinion.

PCT/EP2020/063908, dated Sep. 11, 2020, International Search Report and Written Opinion.

International Search Report and Written Opinion for Application No. PCT/EP2018/082361 dated Feb. 22, 2019.

International Search Report and Written Opinion for Application No. PCT/EP2020/063909 daetd Jul. 2, 2020.

International Search Report and Written Opinion for Application No. PCT/EP2020/063913 dated Jul. 15, 2020.

International Search Report and Written Opinion for Application No. PCT/EP2020/063908 daetd Sep. 11, 2020.

Fan et al., Differential effects of pro-BDNF on sensory neurons after sciatic nerve transection in neonatal rats. Eur J Neurosci. May, 2008;27(9):2380-90. doi: 10.1111/j.1460-9568.2008.06215.x. Epub Apr. 22, 2008.

Fan et al., Modifications of the isonipecotic acid fragment of SNS-032: analogs with improved permeability and lower efflux ratio. Bioorg Med Chem Lett. Dec. 1, 2008;18(23):6236-9. doi: 10.1016/j.bmcl.2008.09.099. Epub Oct. 2, 2008.

Knobloch et al., Keto Esters Derived from 2-(Trimethylsilyl) ethanol: An Orthogonal Protective Group for β-Keto Esters. Synthesis 2008.14 (2008): 2229-2246.

Kotsuki et al., Highly practical, enantiospecific synthesis of the cyclohexyl fragment of the immunosuppressant FK-506. J Org Chem. Aug. 1992;57(18):5036-40.

Ahari et al., A direct stereoselective approach to trans-2,3-disubstituted piperidines: application in the synthesis of 2-Epi-CP-99,994 and (+)-epilupinine. Org Lett. Jun. 19, 2008;10(12):2473-6. doi: 10.1021/ol800722a. Epub May 14, 2008.

Billeter et al., 8-Hydroxyflavonoid Glucuronides from Malva Sylvestris. Phytochemistry. 1991; 30(3):987-90.

Brown et al., Structurally constrained hybrid derivatives containing octahydrobenzo[g or f]quinoline moieties for dopamine D2 and D3 receptors: binding characterization at D2/D3 receptors and elucidation of a pharmacophore model. J Med Chem. Dec. 25, 2008;51(24):7806-19. doi: 10.1021/jm8008629.

Fumeaux et al., First synthesis, characterization, and evidence for the presence of hydroxycinnamic acid sulfate and glucuronide conjugates in human biological fluids as a result of coffee consumption. Org Biomol Chem. Nov. 21, 2010;8(22):5199-211. doi: 10.1039/c0ob00137f. Epub Sep. 14, 2010.

Zhang et al., Flavonoid metabolism: the synthesis of phenolic glucuronides and sulfates as candidate metabolites for bioactivity studies of dietary flavonoids. Tetrahedron. 2012; 68:4194-4201.

* cited by examiner

Time (min)

SOLID FORMS OF (2S,3S,4S,5R,6S)-3,4,5-TRIHYDROXY-6-(((4AR,10AR)-7-HYDROXY-1-PROPYL-1,2,3,4,4A,5,10,10A-OCTAHYDROBENZO[G]QUINOLIN-6-YL)OXY)TETRAHYDRO-2H-PYRAN-2-CARBOXYLIC ACID

CROSS-REFERENCE TO RELATED APPLICATIONS

This application claims priority to Danish Application No. PA201900612, filed May 21, 2019, Danish Application No. PA201900598, filed May 20, 2019, Danish Application No. PA201900599, filed May 20, 2019, and Danish Application No. PA201900636, filed May 24, 2019, the entire contents of the aforementioned applications are hereby incorporated herein by reference.

FIELD OF THE INVENTION

The present invention relates to new solid forms of (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid which is a compound for use in the treatment of neurodegenerative diseases and disorders such as Parkinson's Disease.

BACKGROUND OF THE INVENTION

Parkinson's disease (PD) is a common neurodegenerative disorder that becomes increasingly prevalent with age and affects an estimated seven to ten million people worldwide. Parkinson's disease is a multi-faceted disease characterized by both motor and non-motor symptoms. Motor symptoms include resting tremor (shaking), bradykinesia/akinesia (slowness and poverty of movements), muscular rigidity, postural instability and gait dysfunction; whereas non-motor symptoms include neuropsychiatric disorders (e.g. depression, psychotic symptoms, anxiety, apathy, mild-cognitive impairment and dementia) as well as autonomic dysfunctions and sleep disturbances (Poewe et al., Nature Review, (2017) vol 3 article 17013: 1-21).

A key hallmark of Parkinson's disease pathophysiology is the loss of pigmented dopaminergic neurons in the substantia nigra pars compacta that provides dopaminergic innervation to the striatum and other brain areas. Such progressive neurodegeneration leads to the decrease in dopamine striatal levels which ultimately results in a series of changes in the basal ganglia circuitry, ultimately ending up in the occurrence of the four cardinal motor features of Parkinson's disease. The main target of dopamine in the striatum consists of medium spiny GABAergic neurons (MSNs) selectively expressing D1 or D2 receptors pending topographical projections. GABAergic-MSN projecting to the external pallidum, also called striata-pallidal 'indirect pathway' express D2 receptors (MSN-2); whereas GABAergic-MSN projecting to the substantia nigra pars reticulata and internal pallidum, also called striata-nigral 'direct pathway' express D1 receptors (MSN-1). Depletion of dopamine because of neuronal loss results in an imbalanced activity of the two pathways, resulting in a marked reduction of thalamic and cortical output activities and ultimately motor dysfunctions (Gerfen et al, Science (1990) 250: 1429-32; Delong, (1990) Trends in Neuroscience 13: 281-5; Alexander et Crutcher, (1990) Trends in Neuroscience 13: 266-71; and for review Poewe et al., Nature Review (2017) vol. 3 article 17013: 1-21).

The most effective therapeutic strategies available to patients suffering from Parkinson's disease, and aiming at controlling motor symptoms are primarily indirect and direct dopamine agonists. The classic and gold standard treatment regimen includes chronic oral intake of L-3,4-dihydroxy phenylalanine (L-DOPA) which is decarboxylated in the brain to form dopamine. Other approaches consist in the administration of dopamine receptor agonists such as apomorphine which acts both on the D1 and D2 receptors subtypes, or pramipexole, ropinirole and others which are predominantly directed towards D2 receptors subtypes. Optimal motor relief is obtained with use of both L-DOPA and apomorphine due to their activation of both D1 and 02 receptor subtypes and holistic re-equilibrium of the indirect-direct pathways (i.e. while D2 agonists only reverse the indirect pathway dysfunction).

L-DOPA and apomorphine with the structures depicted below are currently the most efficacious PD drugs in clinical use.

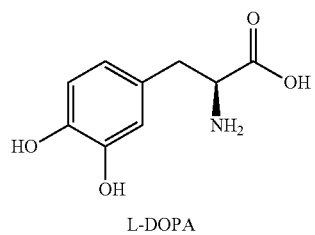

L-DOPA

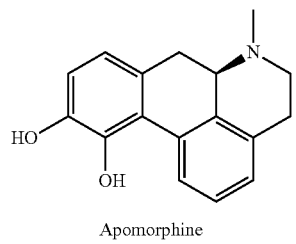

Apomorphine

L-DOPA is a prodrug of dopamine and remains the most efficacious drug in the treatment of motor Parkinson's disease. However, after several years of treatment (i.e. honeymoon period), complications arise due the inherent progression of the disease (i.e. sustained loss of dopaminergic neurons) as well as poor pharmacokinetic (PK) profile of L-DOPA. Those complications include[1] dyskinesia which are abnormal involuntary movements occurring during the optimal 'on-time effect' of the drug; and[2] off fluctuations, periods during which the L-DOPA positive effect wears off and symptoms re-emerge or worsen (Sprenger and Poewe, CNS Drugs (2013), 27: 259-272).

Direct dopamine receptor agonists are able to activate the dopamine autoreceptors as well as the postsynaptic dopamine receptors located on the medium spiny neurons MSN-1 and MSN-2. Apomorphine belongs to a class of dopamine agonists with a 1,2-dihydroxybenzene (catechol) moiety. When combined with a phenethylamine motif, catecholamines often possess low or no oral bioavailability as is the case for apomorphine. Apomorphine is used clinically in PD therapy albeit with a non-oral delivery (typically intermittent subcutaneous administration or daytime continuous parenteral infusion via a pump). For apomorphine, animal studies have shown that transdermal delivery or implants may provide possible forms of administration. However, when the delivery of apomorphine from implants was studied in monkeys (Bibbiani et al., Chase Experimental Neurology (2005), 192: 73-78) it was found that in most cases the animals had to be treated with the immunosuppressant Dexamethasone to prevent local irritation and other complications following the implantation surgery. Alternative delivery strategies for apomorphine therapy in PD such as inhalation and sublingual formulations have been extensively explored (see e.g. Grosset et al., Acta Neural Scand. (2013), 128:166-171 and Hauser et al., Movement Disorders (2016), Vol. 32 (9): 1367-1372). However, these efforts are yet not in clinical use for the treatment of PD.

An alternative to the non-oral formulations of the catecholamines involves the use of a prodrug masking the free catechol hydroxyl groups to enable oral administration. However, a known problem associated with the development of prodrugs for clinical use is the difficulties associated with predicting conversion to the parent compound in humans.

Various ester prodrugs of catecholamines have been reported in the literature such as enterically coated N-propyl-noraporphine (NPA) and the mono pivaloyl ester of apomorphine for duodenal delivery (see eg. WO 02/100377), and the D1-like agonist adrogolide, a diacetyl prodrug of A-86929 (Giardina and Williams; CNS Drug Reviews (2001), Vol. 7 (3): 305-316). Adrogolide undergoes extensive hepatic first-pass metabolism in man after oral dosing and, as a result, has a low oral bioavailability (app. 4%). In PD patients, intravenous (IV) adrogolide has antiparkinson efficacy comparable to that of L-DOPA (Giardina and Williams; CNS Drug Reviews (2001), Vol. 7 (3): 305-316).

In addition to the ester prodrugs of catecholamines, an alternative prodrug approach involves the masking of the two catechol hydroxyl groups as the corresponding methylene-dioxy derivative or di-acetalyl derivative. This prodrug principle has been described for example in Campbell et al., Neuropharmacology (1982); 21(10): 953-961 and in U.S. Pat. No. 4,543,256, WO 2009/026934 and WO 2009/026935.

Yet another suggested approach for a catecholamine prodrug is the formation of an enone derivative as suggested in for example WO2001/078713 and in Liu et al., Bioorganic Med. Chem. (2008), 16: 3438-3444. For further examples of catecholamine prodrugs see for example Sozio et al., Exp. Opin. Drug Disc. (2012); 7(5): 385-406.

The compound (4aR,10aR)-1-Propyl-1,2,3,4,4a,5,10,10a-octahydro-benzo[g]quinoline-6,7-diol depicted as compound (I) below is disclosed in WO2009/026934. The trans-isomer was disclosed previously in Liu et al., J. Med. Chem. (2006), 49: 1494-1498 and then in Liu et al., Bioorganic Med. Chem. (2008), 16: 3438-3444 including pharmacological data indicating that the compound has a low oral bioavailability in rats. The racemate was disclosed for the first time in Cannon et al., J. Heterocyclic Chem. (1980); 17: 1633-1636.

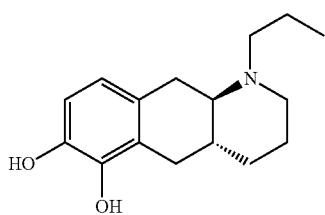

(I)

Compound (I) is a dopamine receptor agonist with mixed D1 and D2 activity. Three prodrug derivatives of compound (I) are known in the art.

Liu et al., J. Med. Chem. (2006), 49: 1494-1498 and Liu et al., Bioorganic Med. Chem. (2008), 16: 3438-3444 disclose the enone derivative of formula (Ia) depicted below which was shown to be converted to the active compound (I) in rats.

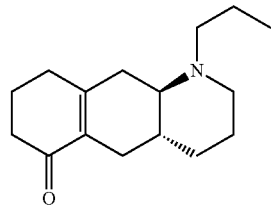

(Ia)

WO2009/026934 and WO2009/026935 disclose two types of prodrug derivatives of compound (I) including a methylenedioxy (MDQ) derivative with the formula (Ib) below:

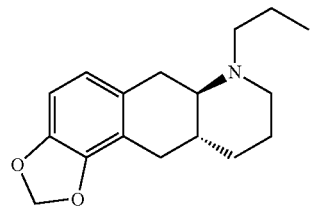

(Ib)

The conversion of compound (Ib) to compound (I) in rat and human hepatocytes has been demonstrated in WO2010/097092. Furthermore, the in vivo pharmacology of the compounds (Ia) and (Ib) as well as the active "parent compound" (I) has been tested in various animal models relevant for Parkinson's Disease (WO2010/097092). Both compound (I) and compounds (Ia) and (Ib) were found to be effective, indicating that compounds (Ia) and (Ib) are converted in vivo to compound (I). All three compounds were reported to have a duration of action that was longer than observed for L-dopa and apomorphine.

The other prodrug of compound (I) disclosed in WO2009/026934 and WO2009/026935 is an ester prodrug of the formula (Ic):

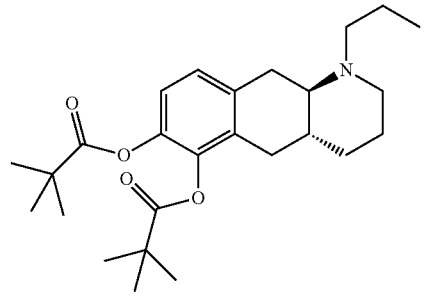

(Ic)

Despite the long-standing interest in the field, there is evidently still an unmet need as regards developing efficient, well-tolerated and orally active drugs for the treatment of PD. A prodrug derivative of a mixed D1/D2 agonist giving a stable PK profile which can provide continuous dopaminergic stimulation may fulfil such unmet needs.

SUMMARY OF THE INVENTION

The inventors of the present invention have surprisingly found that (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid, compound (Id), is advantageous since testing in vivo and in vitro have shown that the compound differs from the prodrugs Ia, Ib and Ic, as demonstrated in Examples 6 to 10 herein. Additionally, the inventors of the present invention have further identified several novel solid forms of the compound of formula (Id), whereof the heptahydrate of the zwitterion, the dihydrate of the zwitterion and the potassium salt as described in Examples 1 to 5 are particularly advantageous. More specifically, the potassium salt and the dihydrate solid form of the zwitterion of compound (Id) were found to have advantageous stability (see Examples 4 and 5). In particular the dihydrate of the zwitterion of compound (Id) was shown to be highly stable in terms of stability testing, water absorption and desorption, and physical stability after grinding and pressure (see Examples 4 and 5), The present invention relates to new solid forms of (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid with the formula (Id) below

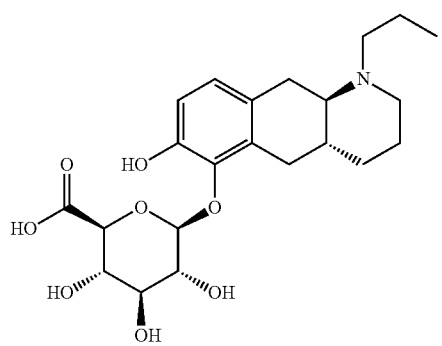

(Id)

Accordingly, the invention relates to a solid form of the compound of formula (Id), wherein said solid form is selected from:
 a) a form of the zwitterion of compound (Id);
 b) an alkali metal salt of the compound of formula (Id); and
 c) a halogen salt of the compound of formula (Id).

In a specific embodiment, the solid form is crystalline. In another specific embodiment, the solid form is crystalline and selected from the group consisting of solid forms listed in Table 2.

In a specific embodiment, the solid form of the compound of formula (Id) is a heptahydrate of the zwitterion of compound (Id), a dihydrate of the zwitterion of compound (Id), or an alkali metal salt of the of compound of formula (Id), preferably a potassium salt of the compound of formula (Id). Preferably, the solid form of the compound of formula (Id) is the dihydrate of the zwitterion of compound (Id) characterized by one or more of the XRPD peaks listed in group (a) of Table 2, or an alkali metal salt of the of compound of formula (Id), such as the potassium salt of the compound of formula (Id), e.g. such as the potassium salt of the compound of formula (Id) characterized by one or more of the XRPD peaks listed in group (a) of Table 2.

In an even more specific embodiment, the solid form of the compound of formula (Id) is the dihydrate solid form of the zwitterion of the compound of formula (Id) (DH1) characterized by one or more of the XRPD peaks listed in group (a) of Table 2.

In one embodiment, the invention relates to a pharmaceutical composition comprising a therapeutically effective amount of a solid form according to the invention of the compound of formula (Id), and one or more pharmaceutically acceptable excipients.

In one embodiment, the invention relates to a solid form according to the invention of the compound of formula (Id), for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

In one embodiment, the invention relates to a method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a solid form according to the invention of the compound of formula (Id).

In one embodiment, the invention relates to the use of a solid form of the compound of formula (Id) as provided herein in the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

Definitions

Prodrug

In the present context, the terms "prodrug" or "prodrug derivative" indicates a compound that, after administration to a living subject, such as a mammal, preferably a human; is converted within the body into a pharmacologically active moiety. The conversion preferably takes place within a mammal, such as in a mouse, rat, dog, minipig, rabbit, monkey and/or human. In the present context a "prodrug of the compound (4aR,10aR)-1-Propyl-1,2,3,4,4a,5,10,10a-octahydro-benzo[g]quinoline-6,7-diol" or "a prodrug of the compound of formula (I)" or "a prodrug of compound (I)" is understood to be a compound that, after administration, is converted within the body into the compound (4aR,10aR)-1-Propyl-1,2,3,4,4a,5,10,10a-octahydro-benzo[g]quinoline-6,7-diol. Said administration may be by any conventional route of administration of pharmaceutical compositions known in the art, preferably by oral administration.

In the present context, the terms "parent compound" and "parent molecule" indicate the pharmacologically active moiety obtained upon conversion of a corresponding prodrug. For example, the "parent compound" of the compound of formula (Id) is understood to be the compound of formula (I).

Pharmacokinetic Definitions and Abbreviations

As used herein, a "PK profile" is an abbreviation of "pharmacokinetic profile". Pharmacokinetic profiles and pharmacokinetic parameters described herein are based on the plasma concentration-time data obtained for the compound of formula (I) after oral dosing of the compound of formula (Id), using non-compartmental modelling. Abbreviated PK parameters are: $C_{max}$ (maximum concentration); $t_{max}$ (time to $C_{max}$); $t_{1/2}$ (half-life); AUC 0-24 (area under the curve from time of dosing and 24 hours after dosing), and "Exposure at 24 h" is the plasma concentration measured 24 hours after dosing.

Therapeutically Effective Amount

In the present context, the term "therapeutically effective amount" of a compound or a solid form of a compound (Id) means an amount sufficient to alleviate, arrest, partly arrest, remove or delay the manifestations, e.g. clinical manifestations of a given disease and its complications in a therapeutic intervention comprising the administration of said compound. An amount adequate to accomplish this is defined as "therapeutically effective amount". Effective amounts for each purpose will depend e.g. on the severity of the disease or injury as well as the weight and general state of the subject.

In the context of the present invention, a "therapeutically effective amount" of the compound of formula (Id) or a solid form thereof, indicates an amount of said compound of the invention that is able to provide an amount of compound (I) that is sufficient to alleviate, arrest, partly arrest, remove or delay the clinical manifestations of a given disease and its complications when said compound of the invention is administered, preferably by the oral route, to a mammal, preferably a human.

Treatment and Treating

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Conditions for Treatment

The solid forms of compound (Id) as prepared by the process of the present invention is intended for treatment of neurodegenerative and neuropsychiatric diseases and disorders such as Parkinson's disease and/or other conditions for which treatment with a dopamine agonist is therapeutically beneficial.

Therapeutic indications include a variety of central nervous system disorders characterized by motor and/or non-motor disturbances and for which part of the underlying pathophysiology is a dysfunction of the striatal-mediated circuitry. Such functional disturbances can be seen in neurodegenerative diseases such as but not limited to Parkinson's disease (PD), Restless leg syndrome, Huntington's disease, and Alzheimer's disease but also neuropsychiatric diseases such as, but not limited to schizophrenia, attention deficit hyperactivity disorder and drug addiction.

In addition to neurodegenerative diseases and disorders, other conditions in which an increase in dopaminergic turnover may be beneficial are in the improvement of mental functions including various aspects of cognition. It may also have a positive effect in depressed patients, and it may also be used in the treatment of obesity as an anorectic agent and in the treatment of drug addiction. It may improve minimal brain dysfunction (MBD), narcolepsy, attention deficit hyperactivity disorder and potentially the negative, the positive as well as the cognitive symptoms of schizophrenia.

Restless leg syndrome (RLS) and periodic limb movement disorder (PLMD) are alternative indications, which are clinically treated with dopamine agonists. In addition, impotence, erectile dysfunction, SSRI induced sexual dysfunction, ovarian hyperstimulation syndrome (OHSS) and certain pituitary tumors (prolactinoma) are also likely to be improved by treatment with dopamine agonists. Dopamine is involved in regulation of the cardiovascular and renal systems, and accordingly, renal failure and hypertension can be considered alternative indications for the compound of formula (Id) and solid forms thereof.

The invention encompasses use of the compound of formula (Id) obtained by a process of the invention for treatment of the diseases and disorders listed above.

Administration Routes

Pharmaceutical compositions comprising a solid form of the compound of formula (Id), either as the sole active compound or in combination with another active compound, may be specifically formulated for administration by any suitable route such as the oral, rectal, nasal, buccal, sublingual, pulmonal, transdermal and parenteral (e.g. subcutaneous, intramuscular, and intravenous) route. In the context of the present invention the oral route is the preferred route of administration.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, carriers, fillers, diluents, antiadherents, binders, coatings, colours, disintegrants, flavours, glidants, lubricants, preservatives, sorbents, sweeteners, solvents, vehicles and adjuvants.

The present invention also provides a pharmaceutical composition comprising the solid forms of compound of formula (Id), such as one of the compounds disclosed in the Experimental Section herein. The present invention also provides a process for making a pharmaceutical composition comprising a solid form of compound of formula (Id). The pharmaceutical compositions according to the invention may be formulated with pharmaceutically acceptable excipients in accordance with conventional techniques such as those disclosed in Remington, "The Science and Practice of Pharmacy", $22^{th}$ edition (2013), Edited by Allen, Loyd V., Jr.

The pharmaceutical composition comprising a solid form of compound (Id) of the present invention is preferably a pharmaceutical composition for oral administration. Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses

In one embodiment, solid forms of compound (Id) of the invention is administered in an amount from about 0.0001 mg/kg body weight to about 5 mg/kg body weight per day. In particular, daily dosages may be in the range of 0.001 mg/kg body weight to about 1 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.01-100 mg/day of a solid form or compound (Id) of the present invention, such as 0.05-50 mg/day, such as 0.1-10 mg/day or 0.1-5 mg/day. Conveniently, the compounds of the invention are administered in a unit dosage form containing said compounds in an amount of about 0.01 to 50 mg, such as 0.05 mg, 0.1 mg, 0.2 mg, 0.5 mg, 1 mg, 5 mg, 10 mg, 15 mg, 20 mg or up to 50 mg of a compound of the present invention.

Non-Hygroscopic

The term "non-hygroscopic" as used herein indicates that the increase in mass of a drug substance between about 0 percent to 80 percent relative humidity is less than 0.2 percent.

Halogen Salt

The term "halogen salt" as used herein indicates a halogenide salt of compound (Id). A halogenide salt is for example a hydrohalogenide salt, such as a HBr or a HCl salt.

XRPD

The term "a solid form characterized by XRPD peaks" or the like is used to denote a solid form that is identifiable by reference to an x-ray powder diffraction pattern as defined by the listed peaks. In particular, peaks listed in Table 2 group (a) for each solid form are useful for identifying solid forms of the invention.

BRIEF DESCRIPTION OF FIGURES

FIG. 2: X-axis: Time (min); Y-axis: Distance travelled (cm)±SEM/5-minute-bins.

FIG. 3: Y-axis: Total distance travelled (cm)±SEM. Significance levels for post-hoc comparisons (relative to the vehicle group) are indicated: *<0.05, <0.01, *<0.001, ****<0.0001.

X-axis time (min); Y-axis left: Distance travelled (cm) ±SEM/5-minute-bins; Y-axis right (FIG. 4): Plasma concentration of compound (I) (pg/mL); Y axis right (FIG. 5): Plasma concentration of apomorphine (ng/mL).

☐: Distance travelled (cm), ● plasma concentration.

Figure 6A:
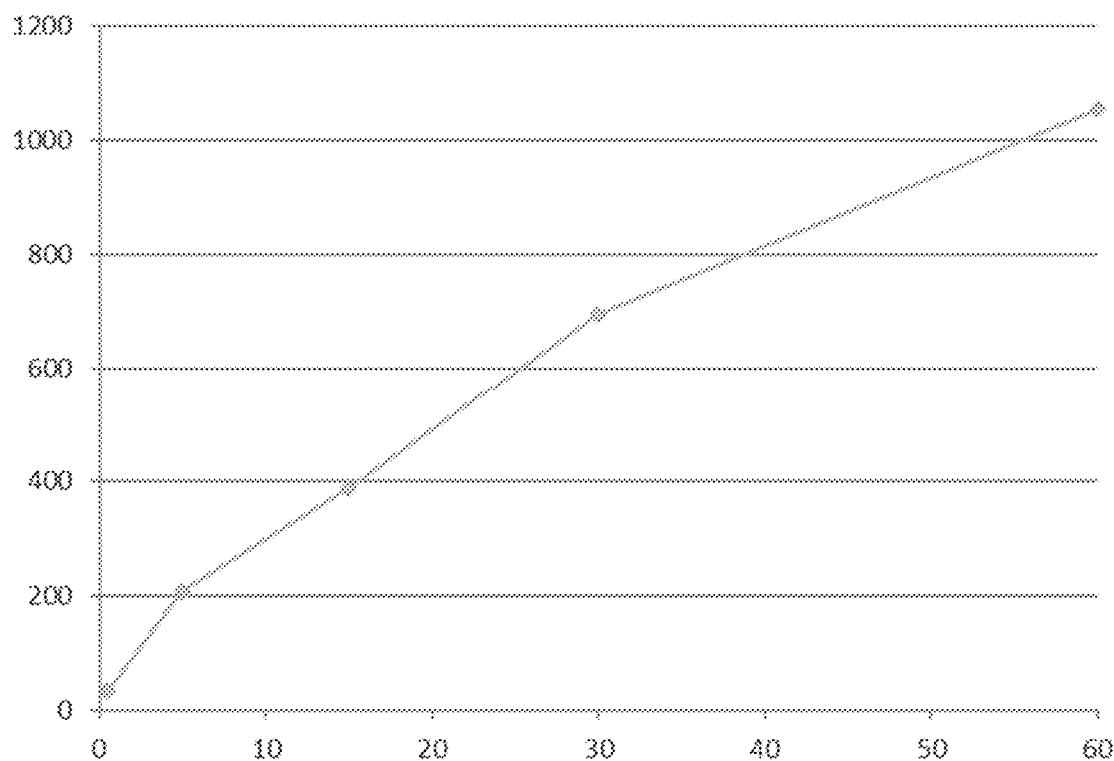
Figure 6B:
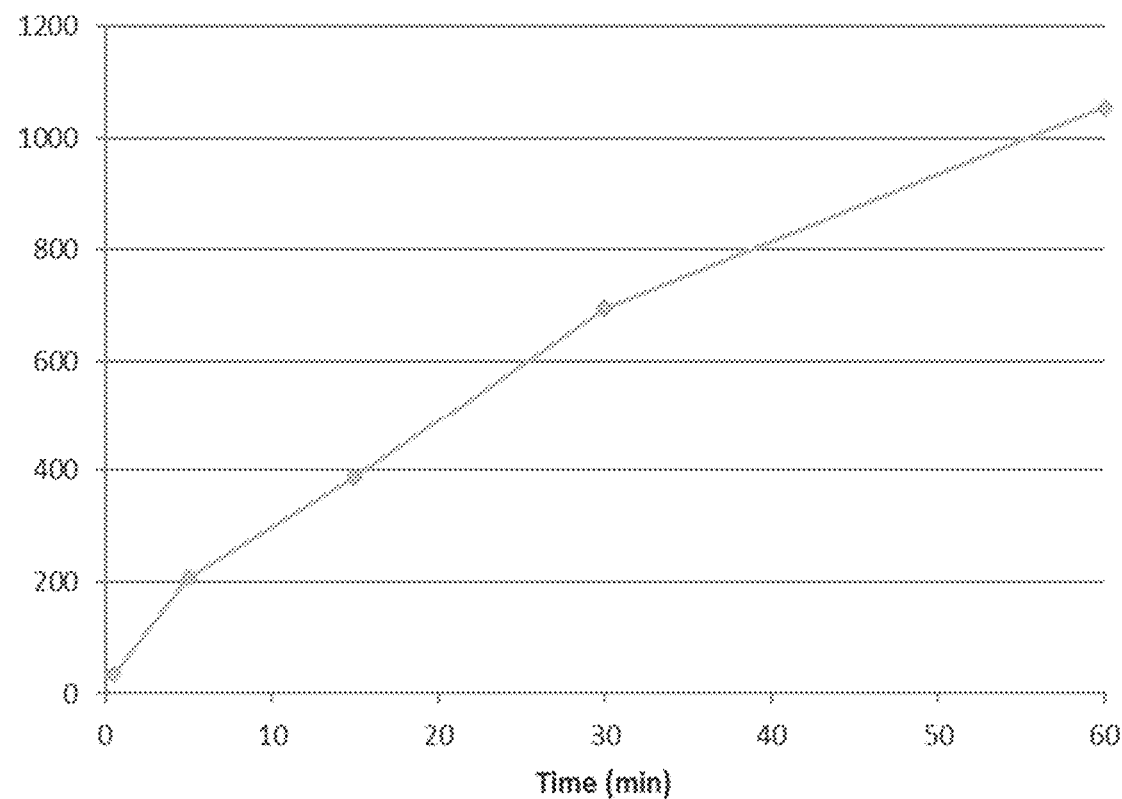

FIGS. 6A-6B: Conversion of compound (Id) to compound (I) in rat (FIG. 6A) and human (FIG. 6B) hepatocytes. X-axis time (min); Y-axis: Concentration of compound (I) (pg/mL).

Figure 7A:
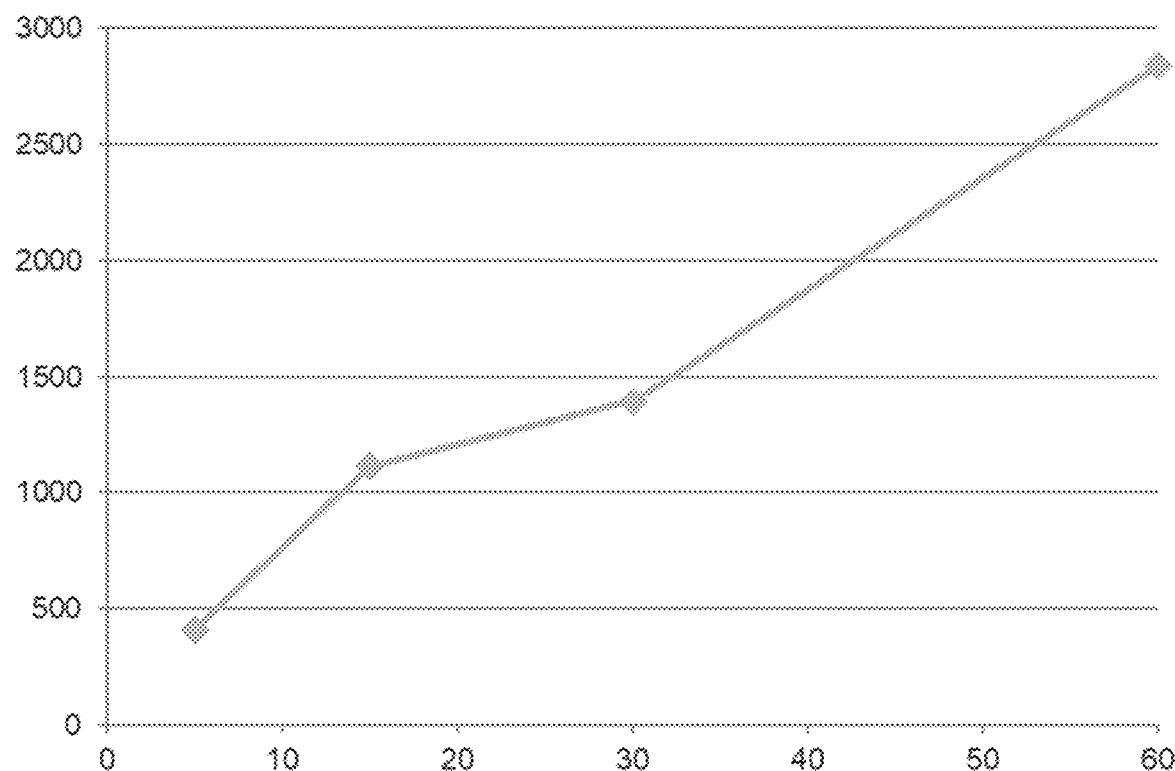
Figure 7B:
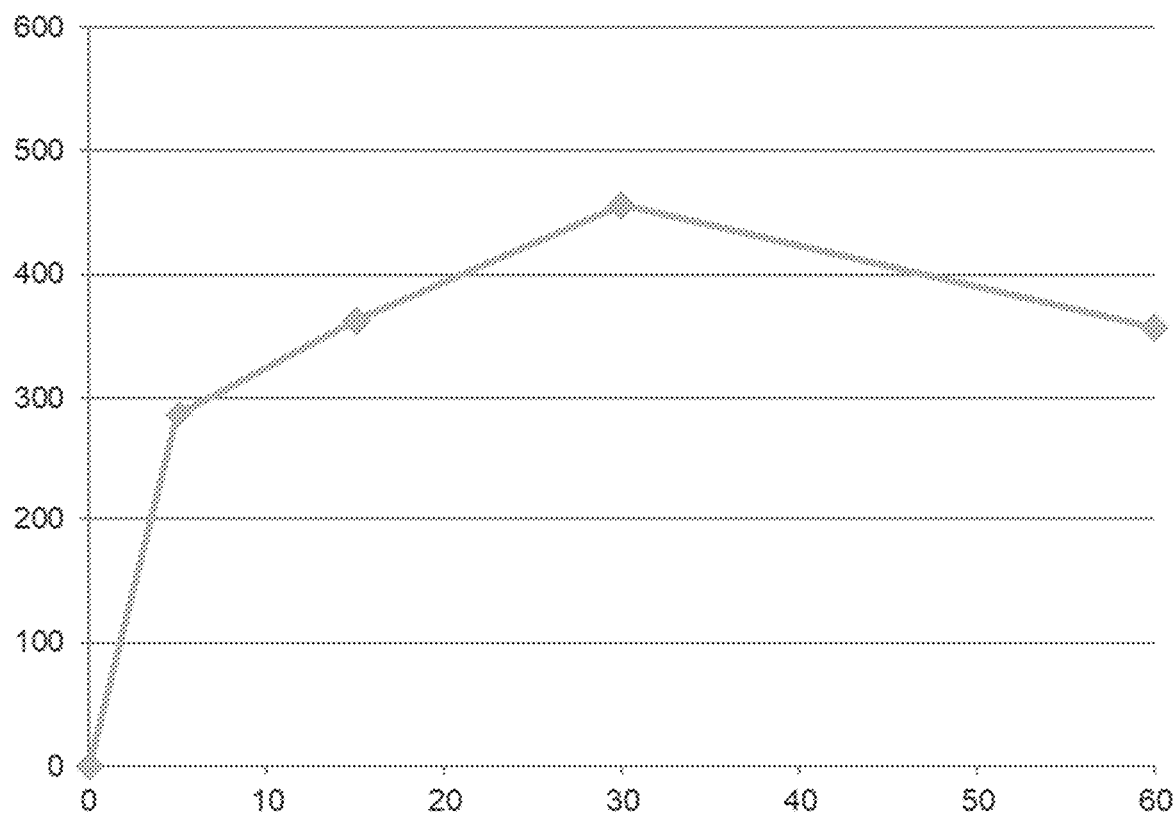

FIGS. 7A-7B: Conversion of compound (Id) in rat (FIG. 7A) and human (FIG. 7B) whole blood. X-axis time (min); Y-axis: concentration of compound (I) (pg/mL).

Figure 8A:
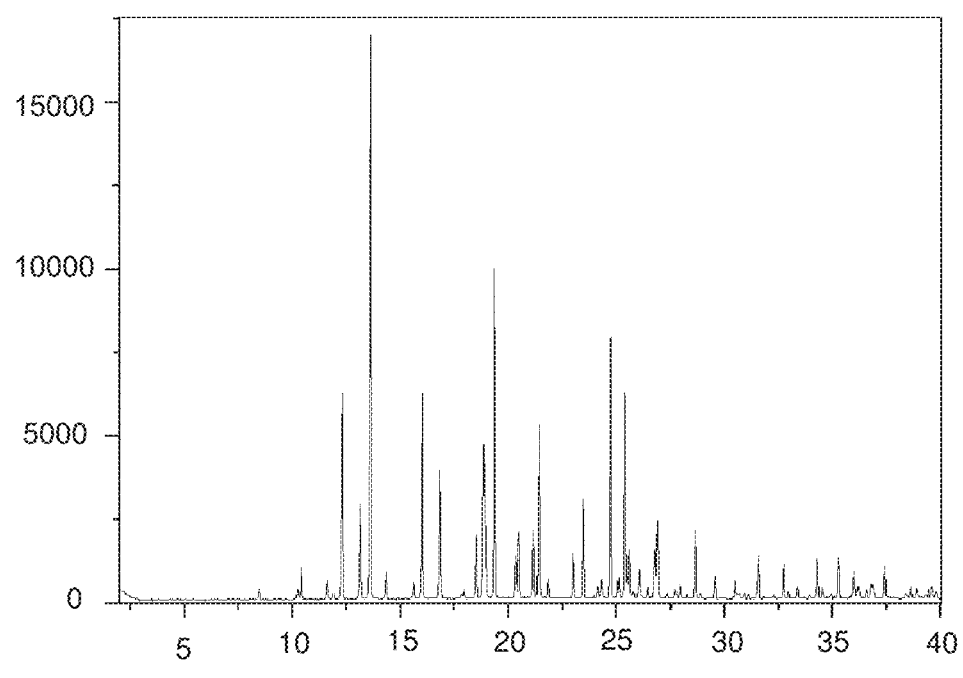
Figure 8B:
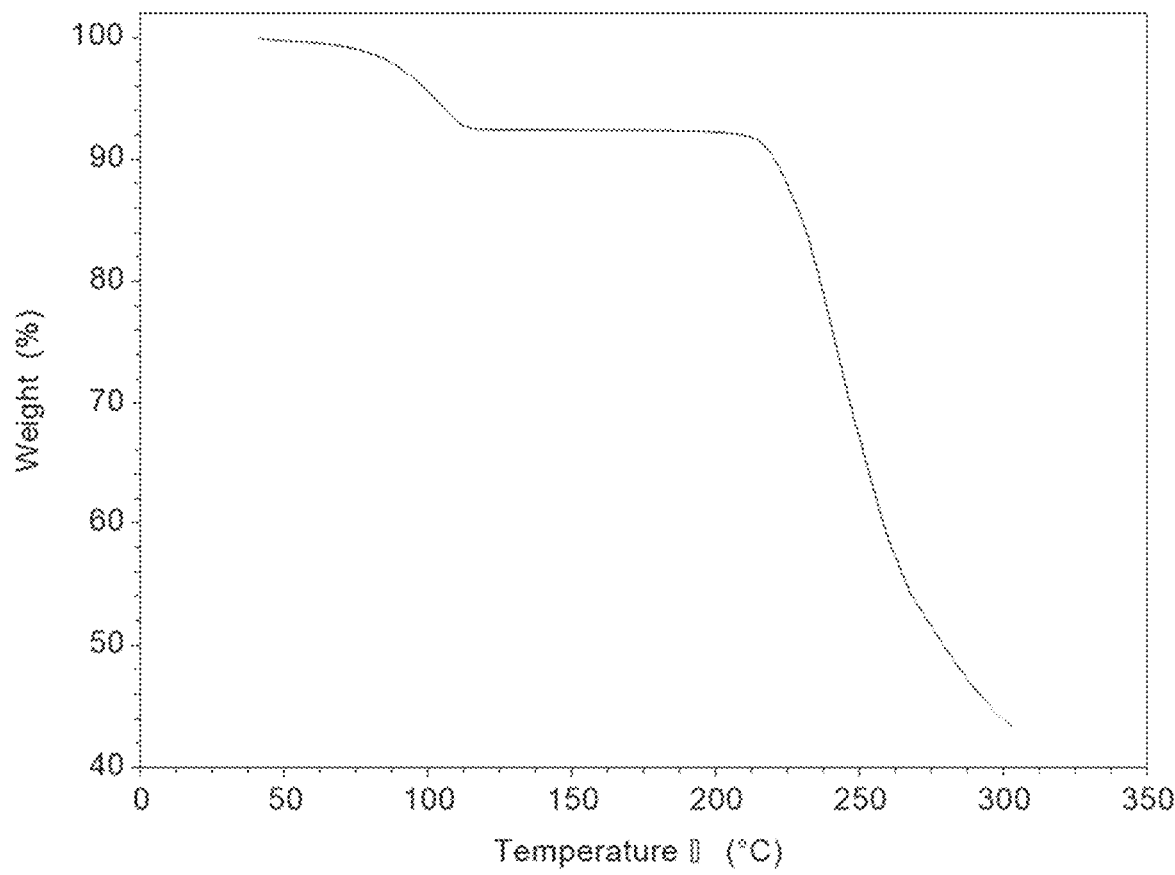

FIGS. 8A-8B: Characterisation of the dihydrate (DH1) of compound (Id) by XRPD (FIG. 8A) and TGA (FIG. 8B).

Figure 9A:
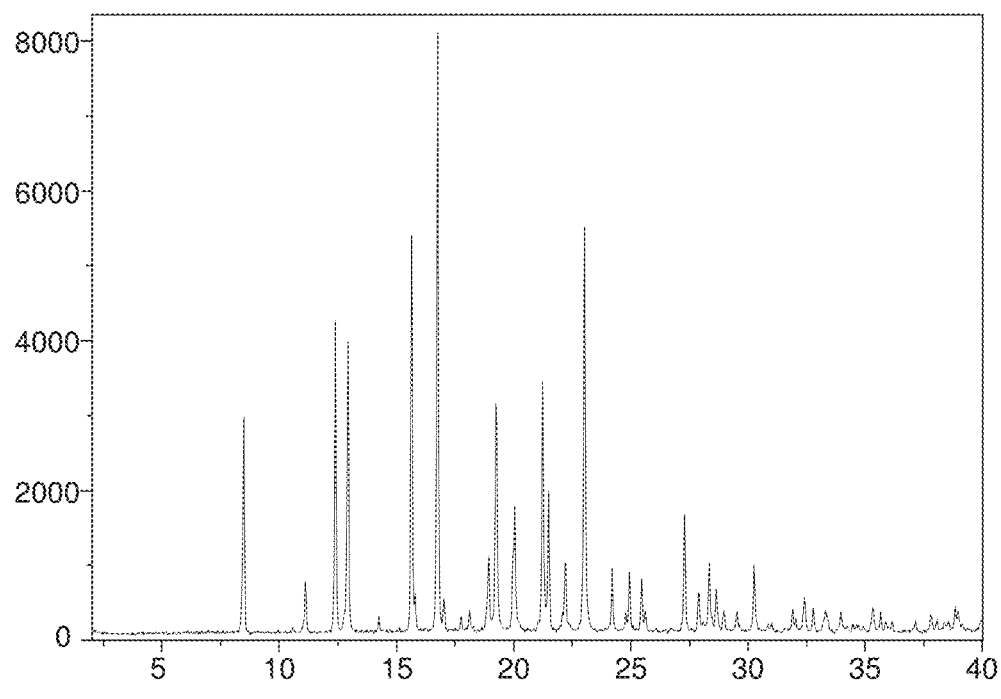
Figure 9B:
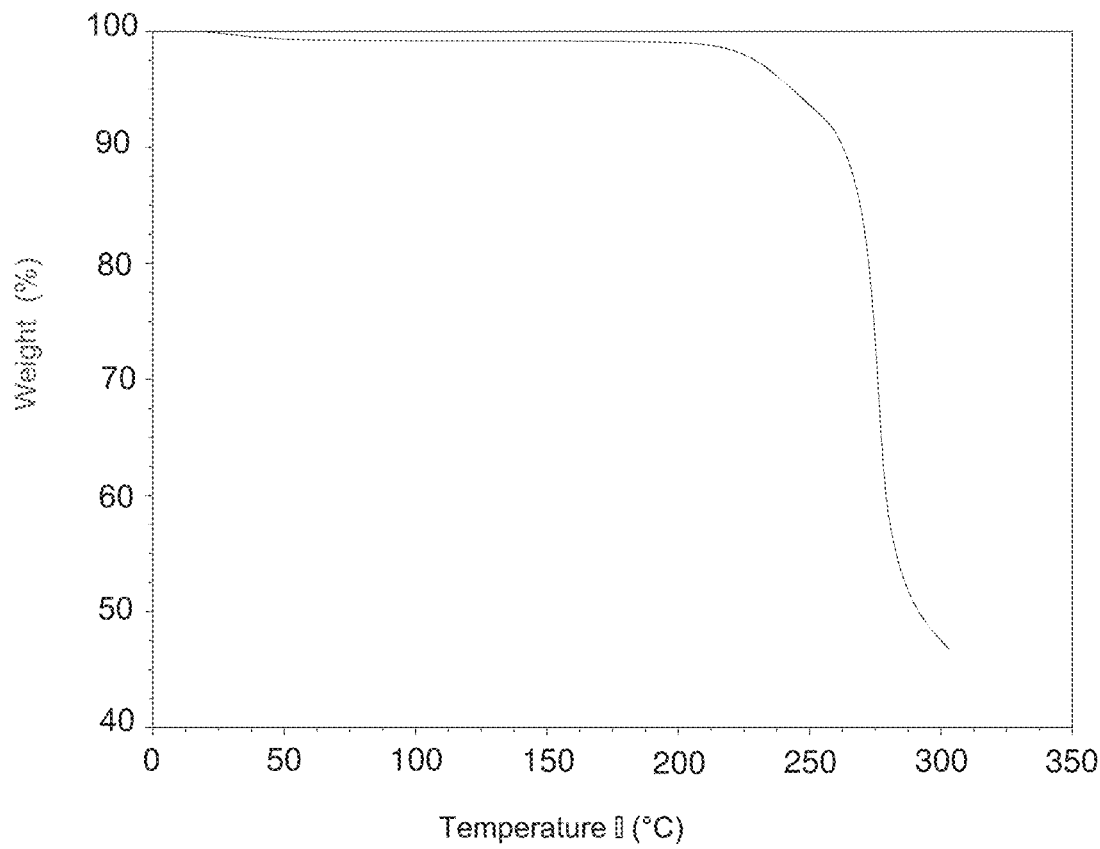

FIGS. 9A-9B: Characterisation of anhydrate (AH1) of compound (Id) by XRPD (FIG. 9A) and TGA (FIG. 9B).

Figure 10A:
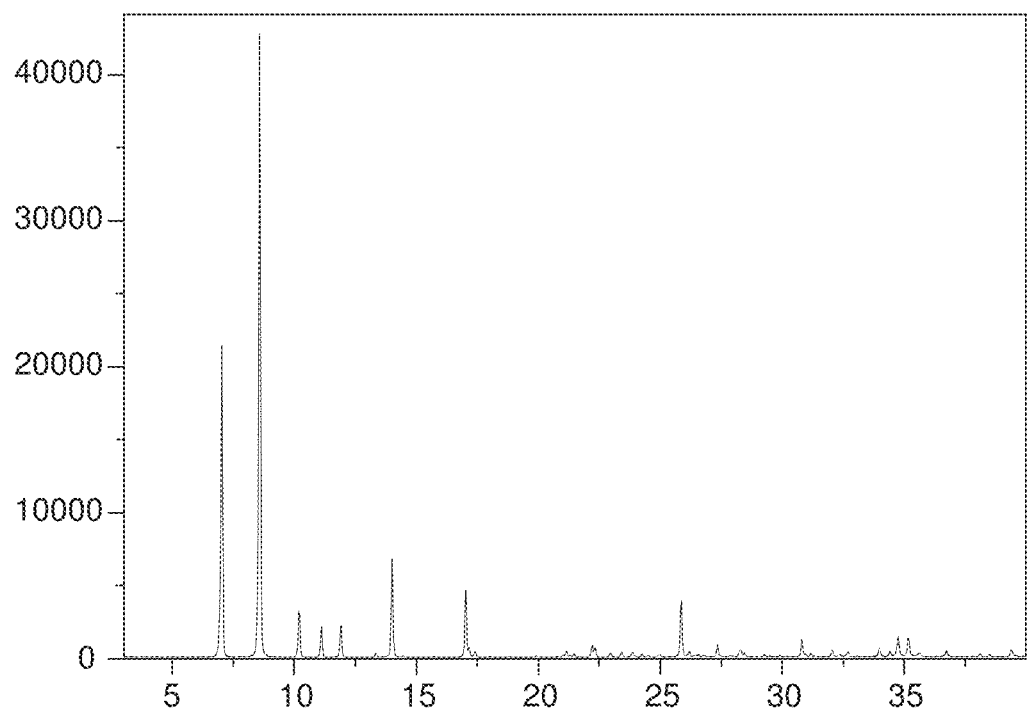
Figure 10B:
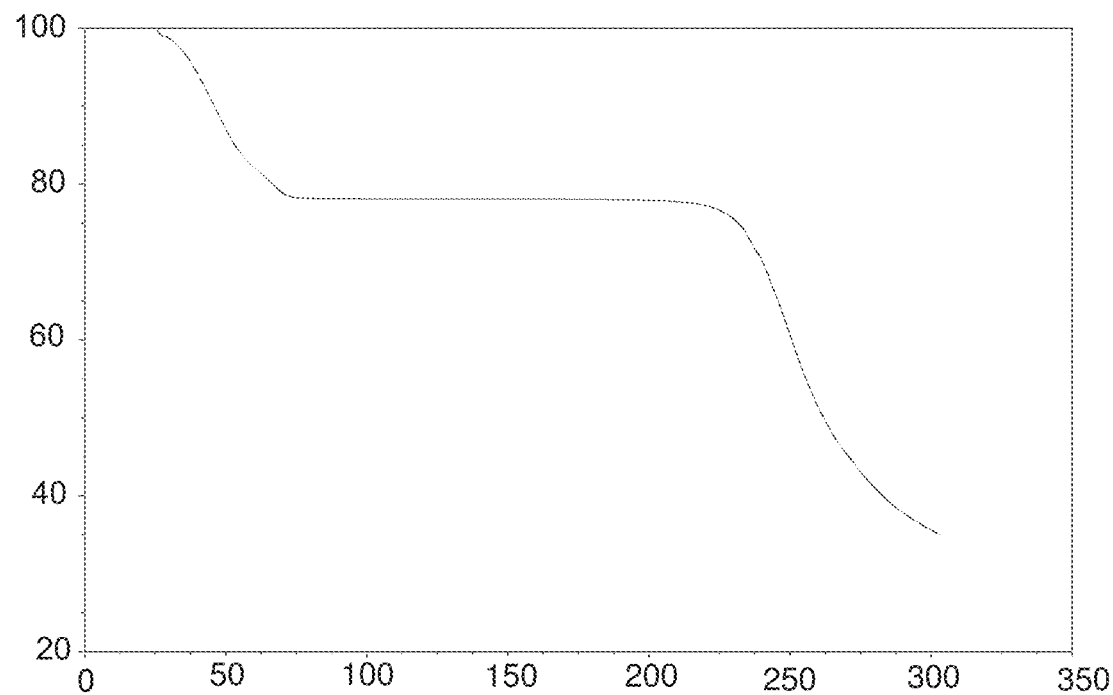

FIGS. 10A-10B: Characterisation of the heptahydrate of compound (Id) by XRPD (FIG. 10A) and TGA (FIG. 10B), FIG. 11: Characterisation of form A of compound (Id) by XRPD.

Figure 12:
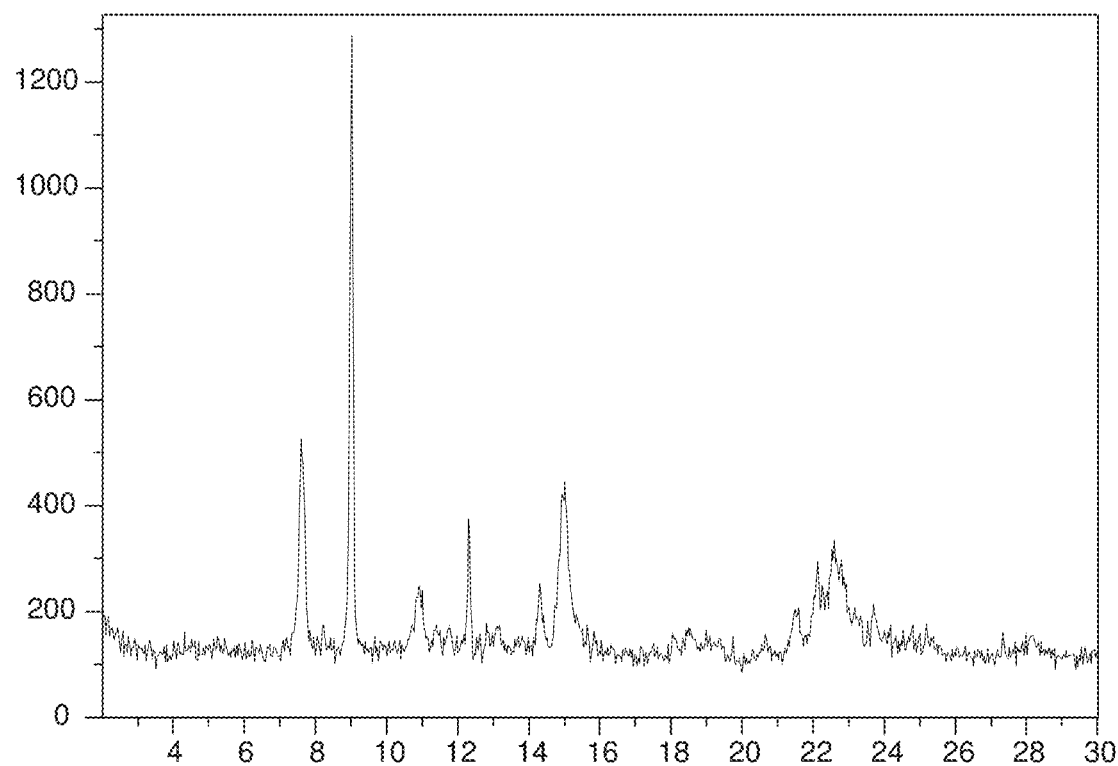

FIG. 12: Characterisation of form B compound (Id) by XRPD.

Figure 13:
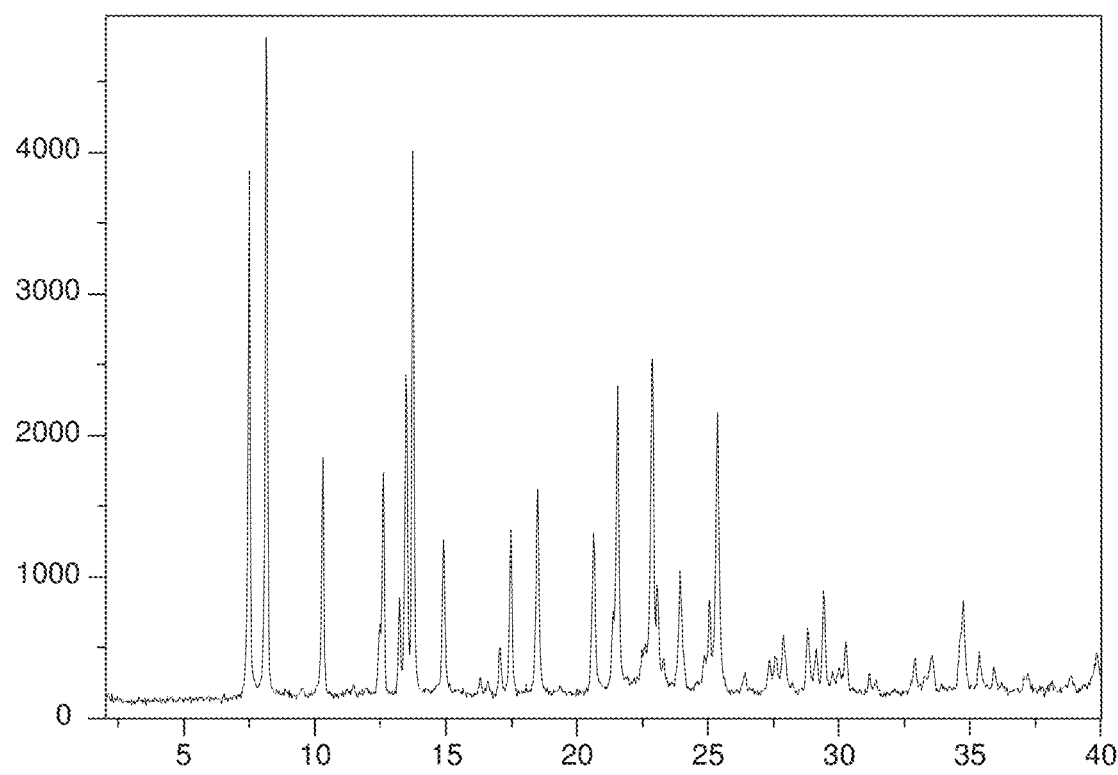

FIG. 13: Characterisation of form C of compound (Id) by XRPD.

Figure 14A:
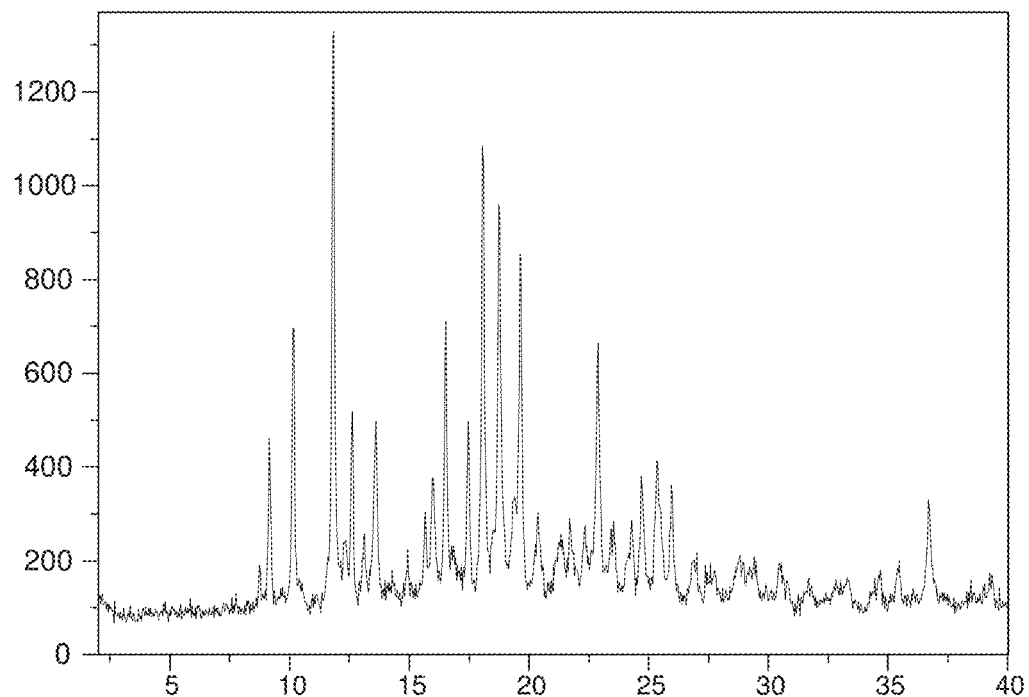
Figure 14B:
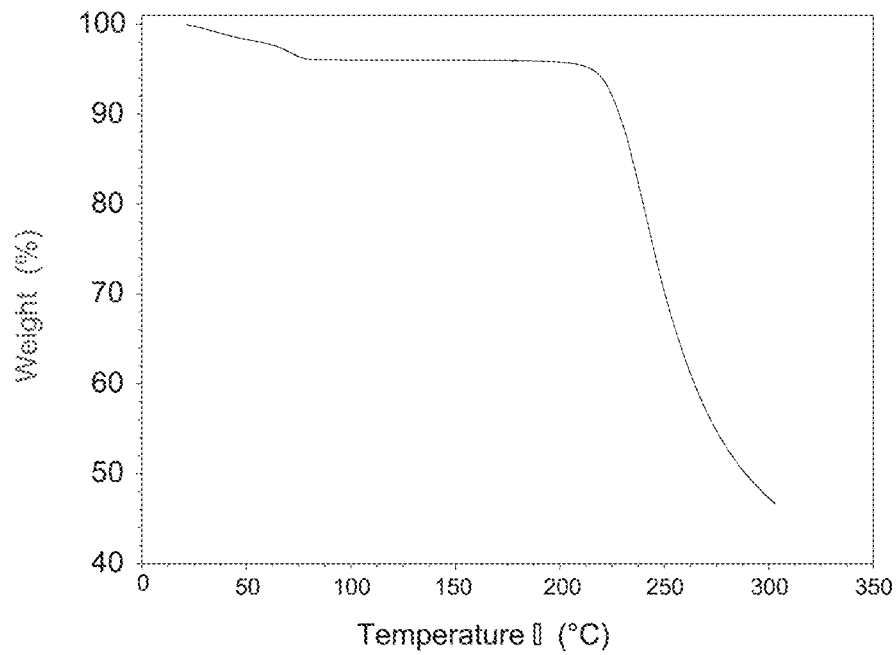

FIGS. 14A-14B: Characterisation of monohydrate (MH1) of compound (Id) by XRPD (FIG. 14A) and TGA (FIG. 14B).

Figure 15A:
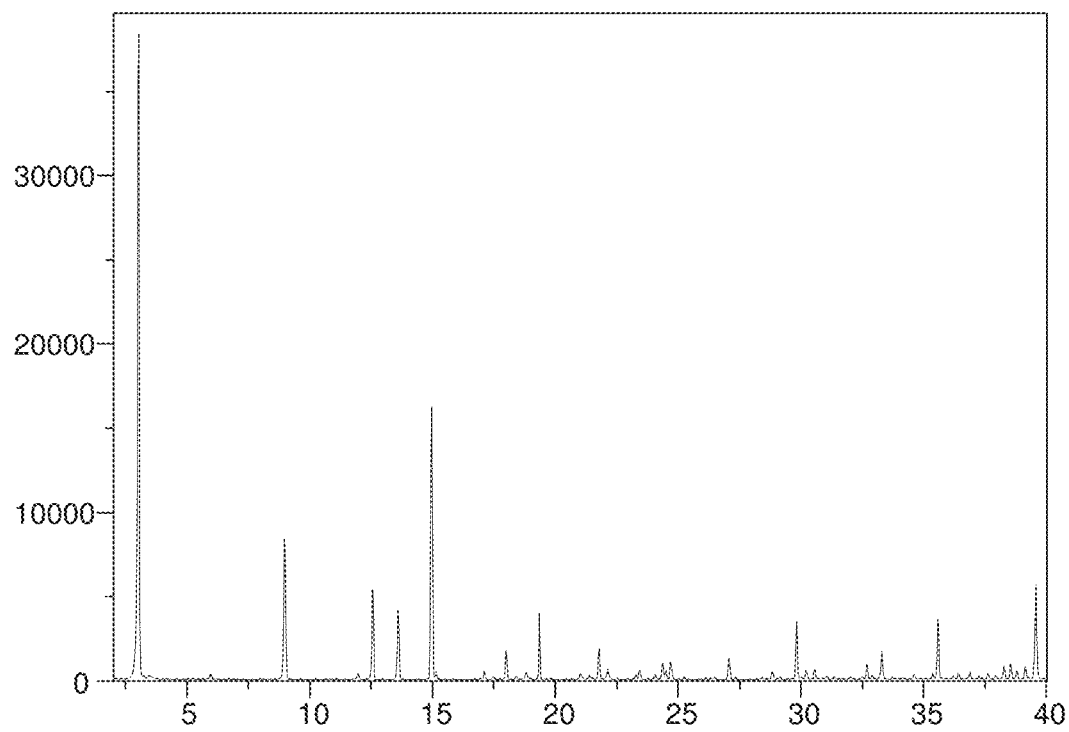
Figure 15B:
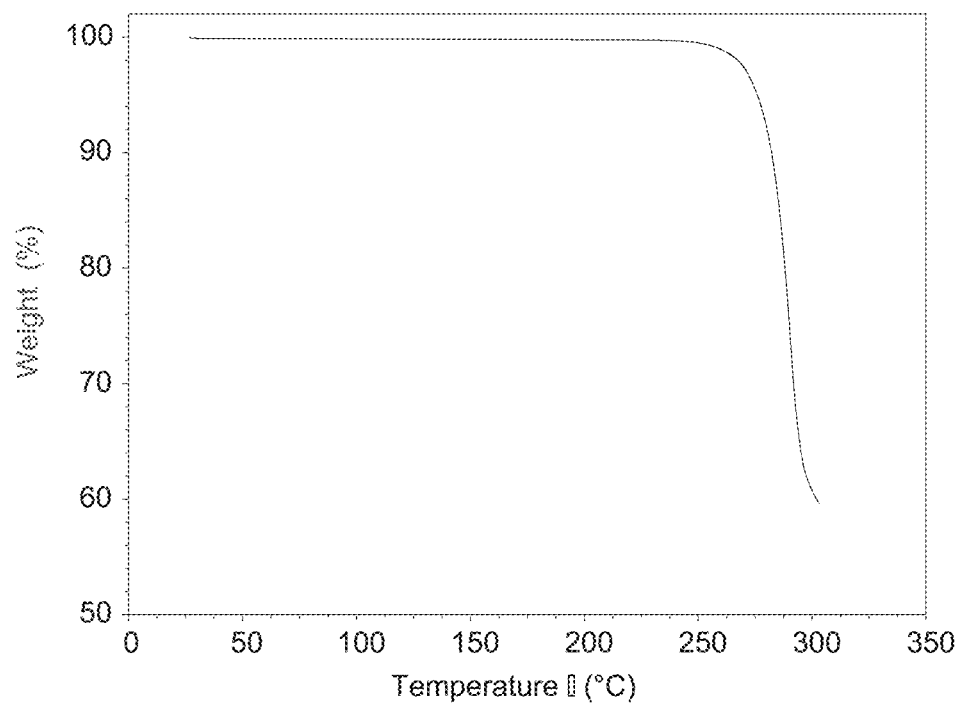

FIGS. 15A-15B: Characterisation of potassium salt of compound (Id) by XRPD (FIG. 15A) and TGA (FIG. 15B).

Figure 16A:
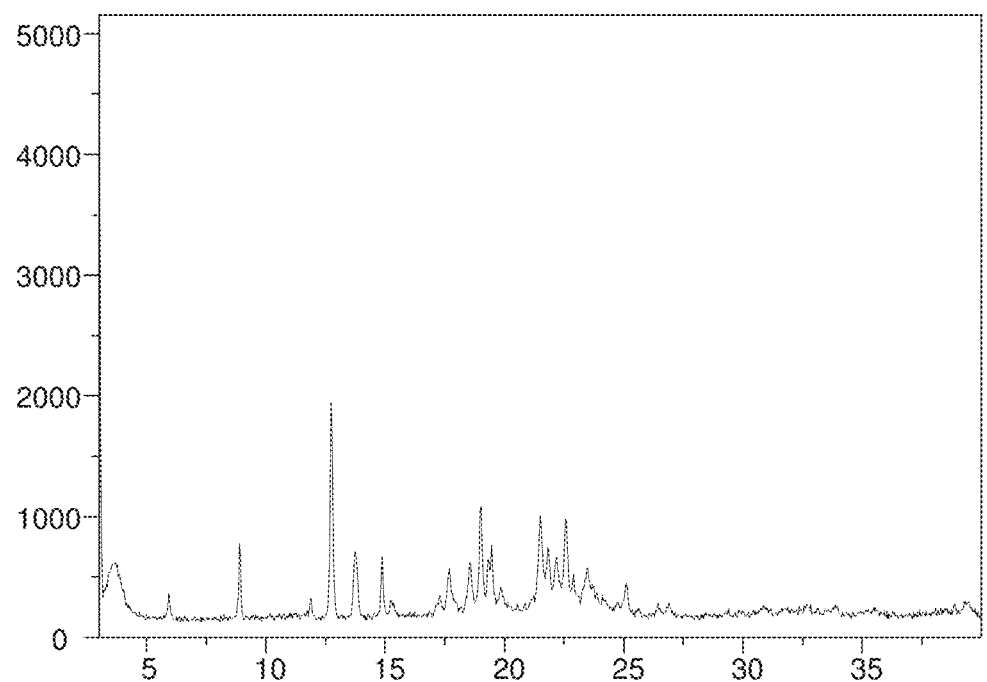
Figure 16B:
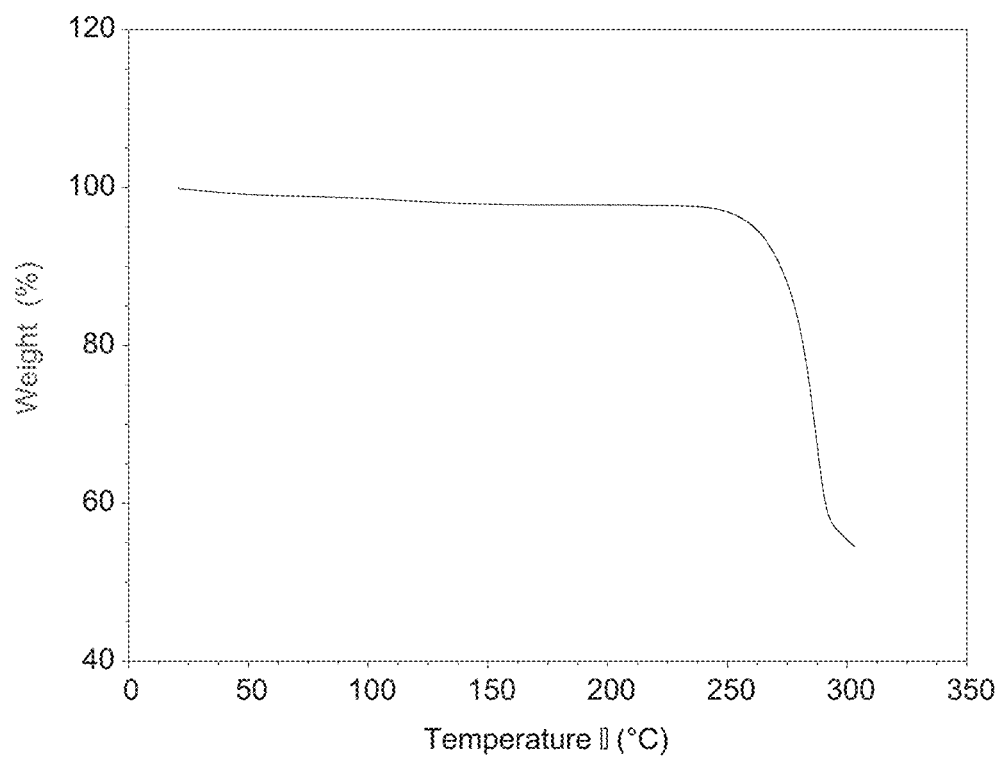

FIGS. 16A-16B: Characterisation of sodium salt form 1 of compound (Id) by XRPD (FIG. 16A) and TGA (FIG. 16B).

Figure 17A:
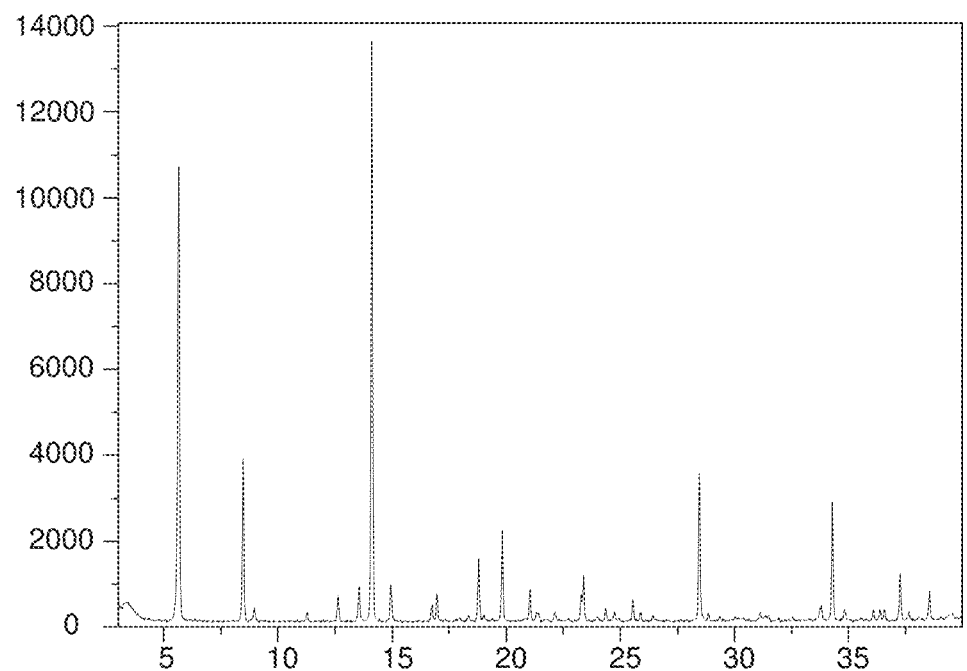
Figure 17B:
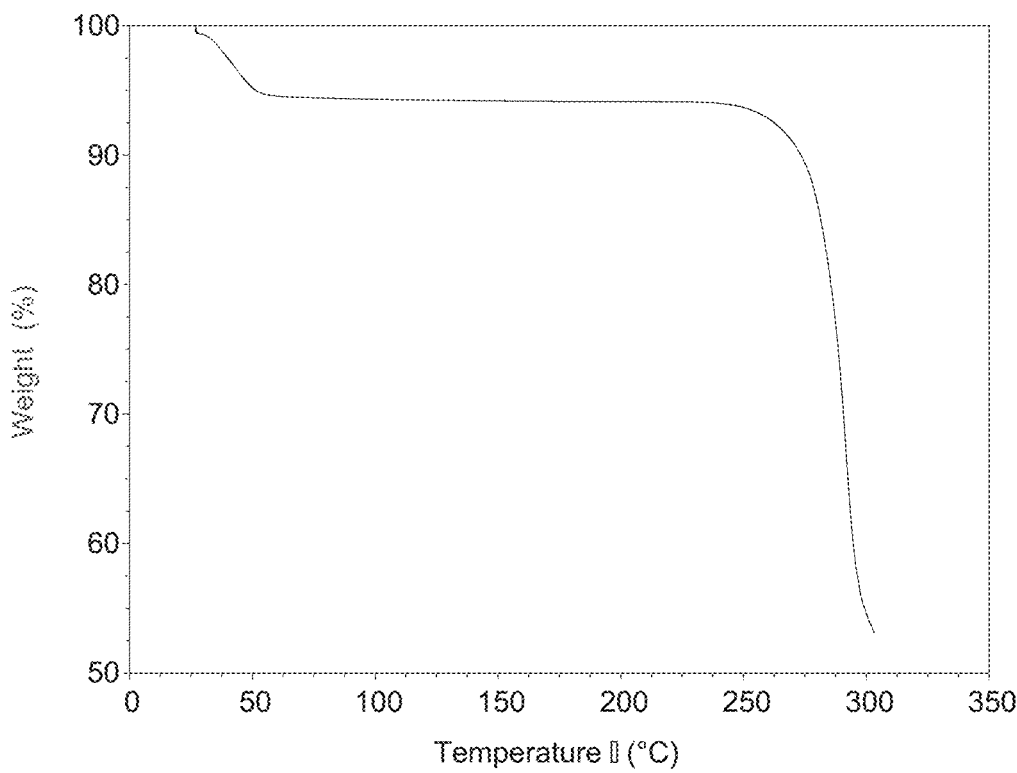

FIGS. 17A-17B: Characterisation of sodium salt form 2 of compound (Id) by XRPD (FIG. 17A) and TGA (FIG. 17B).

Figure 18:
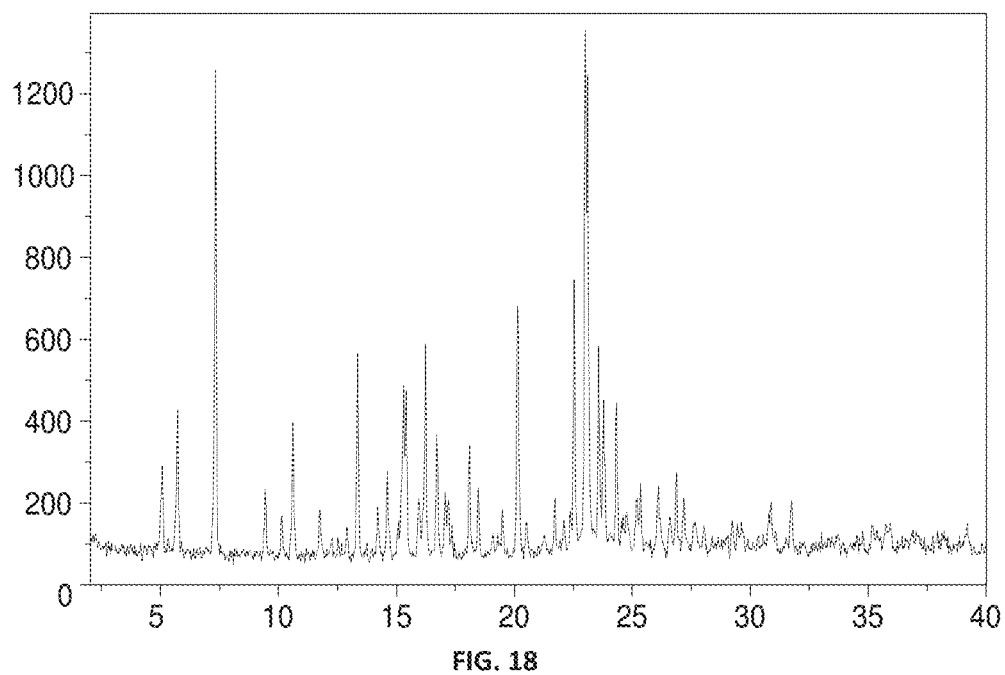

FIG. 18: Characterisation of hydrochloride salt of compound (Id) by XRPD.

Figure 19:
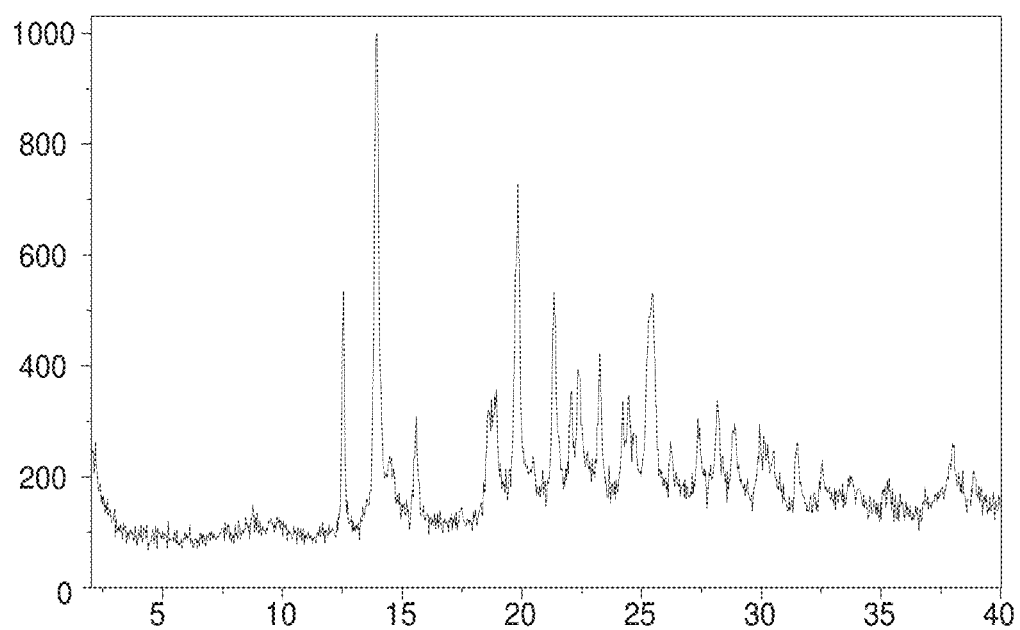

FIG. 19: Characterisation of hydrobromide salt of compound (Id) by XRPD.

Figure 20:
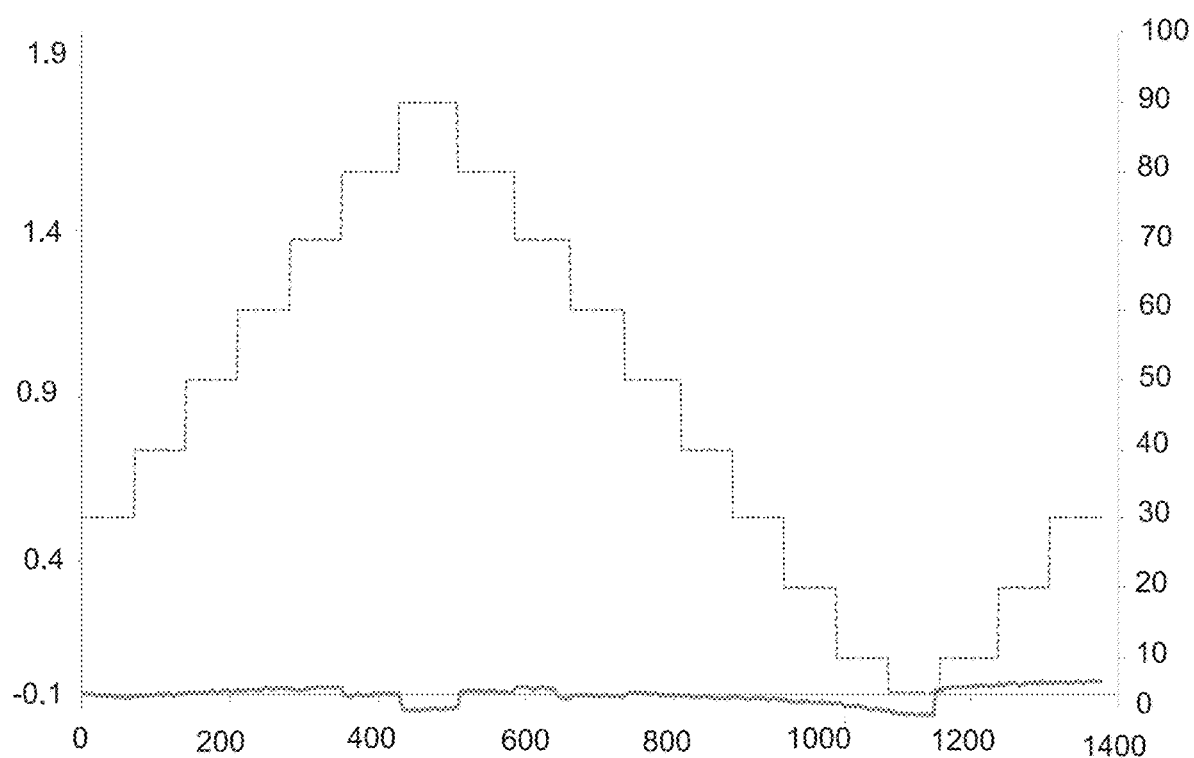

FIG. 20: Characteristic DVS curve of the dihydrate DH1 of the zwitterion of compound (Id). X axis: Time in minutes, Y axis left: Change in Mass %—Dry, Y axis right: Target Relative humidity in % P/Po. The fine broken line denotes the relative humidity, which was increased and decreased in steps of 5-10% RH between 5 and 90% RH, and the broader line denotes the change in mass of the dihydrate DH1 of compound (Id), FIG. 21: Characteristic DVS curve of potassium salt of compound (Id), X axis: Time in minutes, Y axis left: Change in Mass %—Dry, Y axis right: Target Relative humidity in % P/Po. The fine broken line denotes the relative humidity, which was increased and decreased in steps of 5-10% RH, and the broader line denotes the change in mass of the potassium salt of compound (Id).

X-ray powder diffractograms (XRPDs) according to FIGS. 8A-19 were measured on a PANalytical X'Pert PRO X-Ray Diffractometer using $CuK_{\alpha 1}$ radiation ($\lambda$=1.5406 Å). The samples were measured in reflection mode in the 2θ-range 2-40° or 3-40 using an X'celerator detector. The y-axis shows the intensity (counts) and the x-axis shows the 2θ-angles (°).

Thermo gravimetric analysis (TGA) according to FIGS. 8A-8B, 9A-9B, 10A-10B, 14A-14B, 15A-15B, 16A-16B, and 17A-17B were measured using a TA-instruments Discovery TGA. 1-10 mg sample was heated 10°/min in an open pan under nitrogen flow. The X axis shows the temperature (° C.) and the y-axis shows the weight loss (%).

DETAILED DESCRIPTION OF THE INVENTION

The present invention relates to new solid forms of the compound (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid with the formula (Id) below and salts thereof

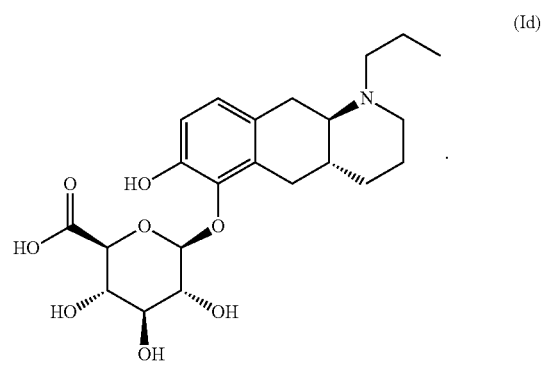 [SMILES: CCCN1CCC[C@@H]2Cc3c(ccc(O)c3O[C@@H]3O[C@H](C(=O)O)[C@@H](O)[C@H](O)[C@H]3O)C[C@H]21]

The compound of formula (Id) is a prodrug of (4aR,10aR)-1-Propyl-1,2,3,4,4a,5,10,10a-octahydro-benzo[g]quinoline-6,7-diol [compound (I)] which is a dual D1/D2 agonist with in vitro data listed in Table 7 of Example 8.

The inventors have observed that compound (I) is conjugated in rat and human hepatocytes to sulfate and glucuronide derivatives including compound (Id). The conjugates have shown to be converted to compound (I) by conjugation and de-conjugation in the body.

Glucuronide and sulfate derivatives are commonly known to be unstable in the intestine. The derivatives are formed as highly polar and soluble metabolites to facilitate the elimination of compounds from the body and are consequently easily excreted. For example, in bile duct cannulated rats, glucuronide and sulfate conjugates are often found in bile while their de-conjugate (i.e. the parent compound) is found in faeces. The back-conversion of glucuronide and sulfate conjugates in the intestine to the parent compound which is then sometimes subsequently reabsorbed, is known as part of the enterohepatic re-circulation process. As mentioned earlier, oral dosing of phenethyl catecholamines, such as apomorphine, has generally proven unsuccessful due to low bioavailability. Likewise, compound (I) suffers from low oral bioavailability (Liu et al., Bioorganic Med. Chem. (2008), 16: 3438-3444). With this in mind and considering the instability of glucuronide and sulfate conjugates in the gastrointestinal tract, it would not be expected that oral dosing of compounds of the invention can be used to achieve sufficient plasma exposure of the compound.

The principle of applying glucuronide derivatives as prodrugs for oral delivery has been explored for retinoic acid (Goswami et al., J. Nutritional Biochem. (2003) 14: 703-709) and for morphine (Stain-Texier et al., Drug Metab. and Disposition (1998) 26 (5): 383-387). Both studies showed very low exposure levels of the parent compounds after oral dosing of the derivatives. Another study suggests the use of budenoside-β-D-glucuronide as a prodrug for local delivery of budenoside to the large intestine for treatment of Ulcerative Colitis based on poor absorption of the prodrug itself from the intestinal system (Nolen et al., J. Pharm Sci. (1995), 84 (6): 677-681).

Nevertheless, surprisingly, it has been observed that oral dosing of compound (Id) which has been identified as a metabolite of compound (I) in rats and minipigs provides a systemic exposure of compound (I) in plasma, suggesting the usefulness of said compound as an orally active prodrug of compound (I).

Figure 1:
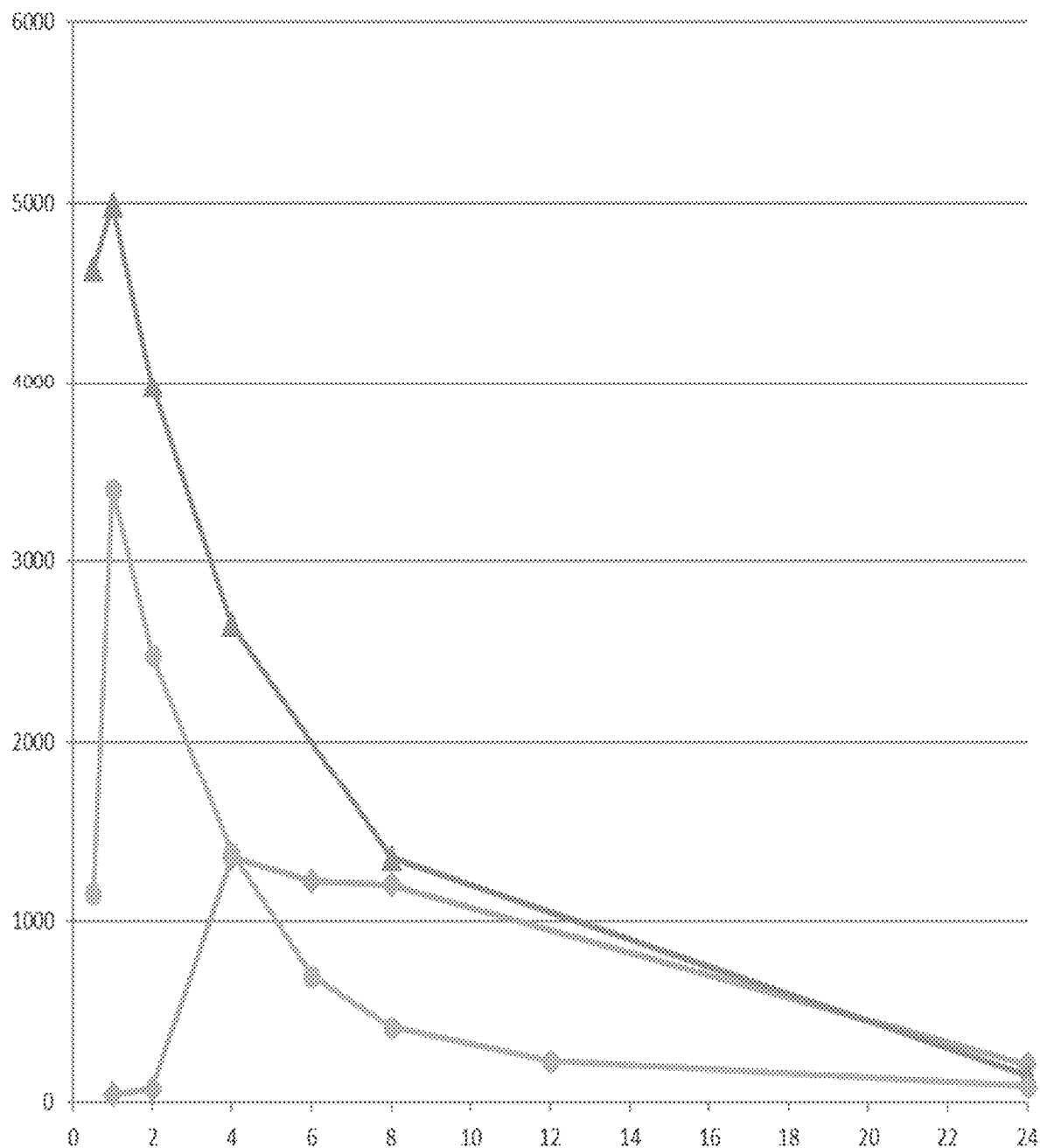
FIG. 1: PK profiles in Wistar rats obtained after oral dosing according to Example 9. Profiles are based on mean plasma concentrations from 3 subjects for each compound, X-axis: time (hours); Y-axis: Plasma concentration of Compound (I) (pg/mL) obtained after dosing of the following compounds ●: compound (Ia); ▲: compound (Ib); ♦: compound (Id).

The plasma profile of compound (I) resulting from oral dosing of compounds (Ia) and (Ib) and compound (Id) to Wistar rats according to Example 9 are shown in FIG. 1. For all the compounds, the doses were corrected by molecular weight to equal a dose of 300 μg/kg of compound (Ib) corresponding to 287 μg/kg of compound (I). The inventors have found that oral dosing of compounds (Ia) and (Ib) to Wistar rats results in early and high peak concentrations of compound (I). Such high peak concentrations are in humans likely to be associated with dopaminergic side effects such as for example nausea, vomiting and light headedness. In contrast, dosing of the compound (Id), results in a slower absorption rate avoiding rapid peak concentrations accompanied by a sustained exposure of compound (I) in plasma. Additionally, the plasma exposure of compound (I) in Wistar rats is maintained throughout 24 hours although the obtained AUC of compound (I) is generally lower than the AUC obtained after dosing of compound (Ib). However, since the peak concentrations of compound (I) which are expected to drive the side effects are lower, higher doses might be administered of the compound (Id) to potentially achieve higher overall plasma concentrations of compound (I) compared to what is achievable from dosing compounds (Ia) and (Ib). When investigating PK properties of compound (Ic), the inventors found that the plasma concentrations of compound (I) were extremely low, leaving compound (Ic) unsuitable as a prodrug of compound (I) for oral administration and confirming that the oral bioavailability demonstrated for the compound of formula (Id) was highly unpredictable. PK parameters for the PK studies in Wistar rats are listed in Table 8 of Example 9.

In vivo conversion of compound (Id) to compound (I) has also been observed by after oral dosing of compound (Id) in minipigs.

Bioconversion of compound (Id) in human is supported by the Experiments of Example 6 indicating conversion to the compound of formula (I) in rat and human hepatocytes and in rat and human blood (FIGS. 6 and 7).

Thus, in conclusion, the compound of formula (Id) is useful as an orally active prodrug of compound (I) and has been observed in rats to provide a PK profile avoiding the peak $C_{max}$ observed for the known prodrugs (Ia) and (Ib) and providing a significantly higher AUC of compound (I) than compound (Ic).

Figure 2:
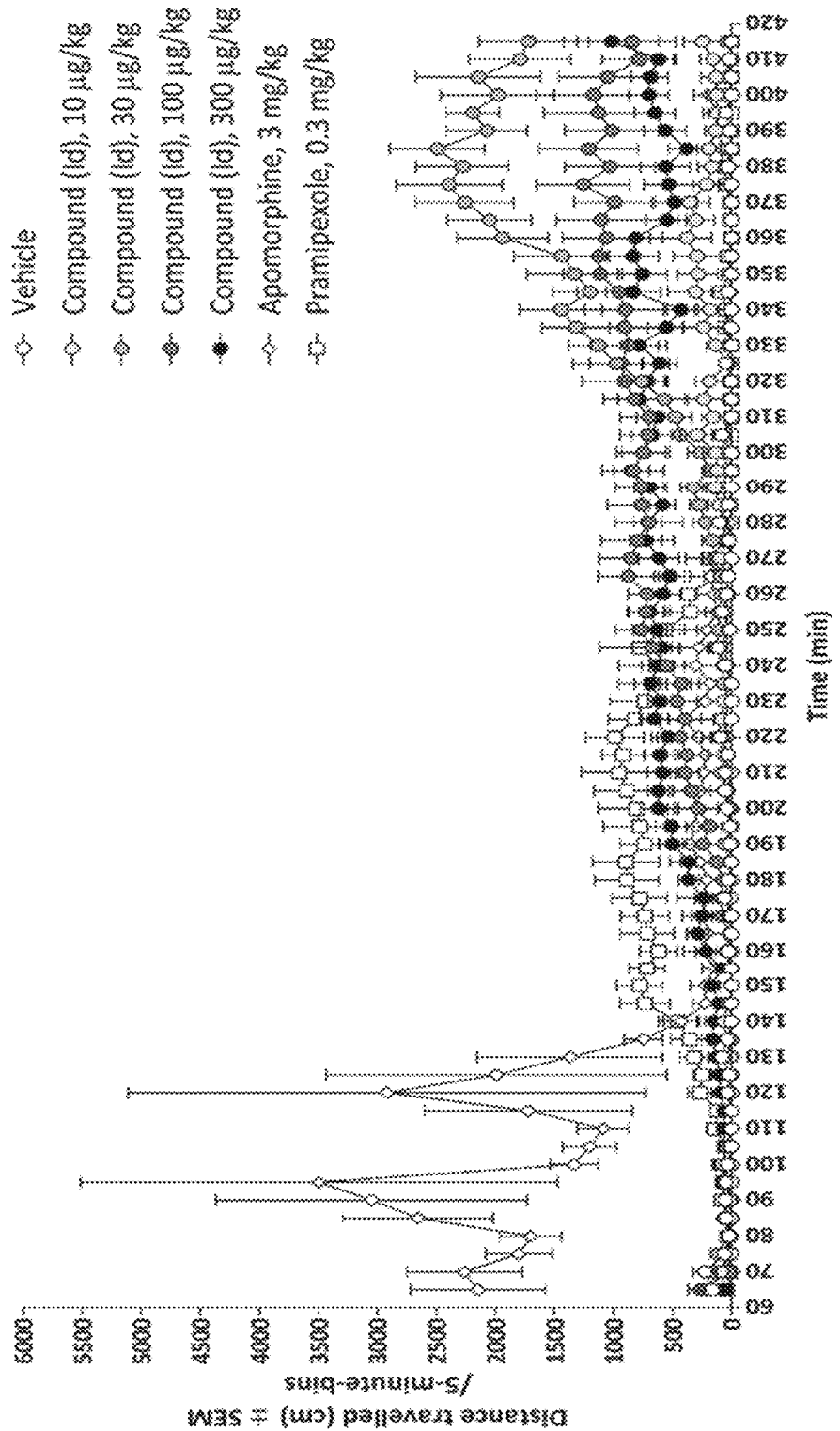
FIG. 2 and FIG. 3: Locomotor activity time-course (FIG. 2) and total distance travelled (FIG. 3) following treatment with vehicle ($H_2O$, p.o.), or compound (Id) (10, 30, 100 or 300 µg/kg, p.o.) and compared to standard-of-care (SoC) treatments: apomorphine (APO, 3 mg/kg, s.c.), pramipexole (PPX, 0.3 mg/kg, s.c.). Animals were dosed at t=60 minutes after a 60-min, habituation period in test chambers, and activity was monitored for 350 minutes thereafter. Data was evaluated by use of a Kruskal-Wallis test with Dunn's Multiple Comparisons test, resulting in an overall P-value of <0.0001.
Figure 3:
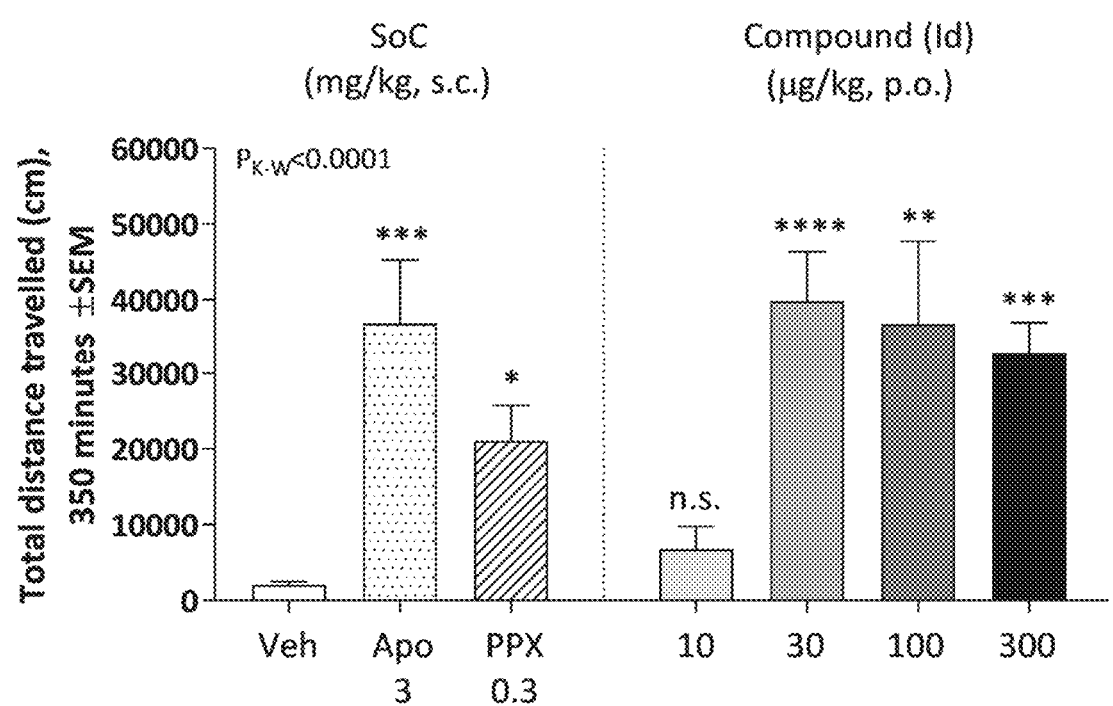
Figure 4:
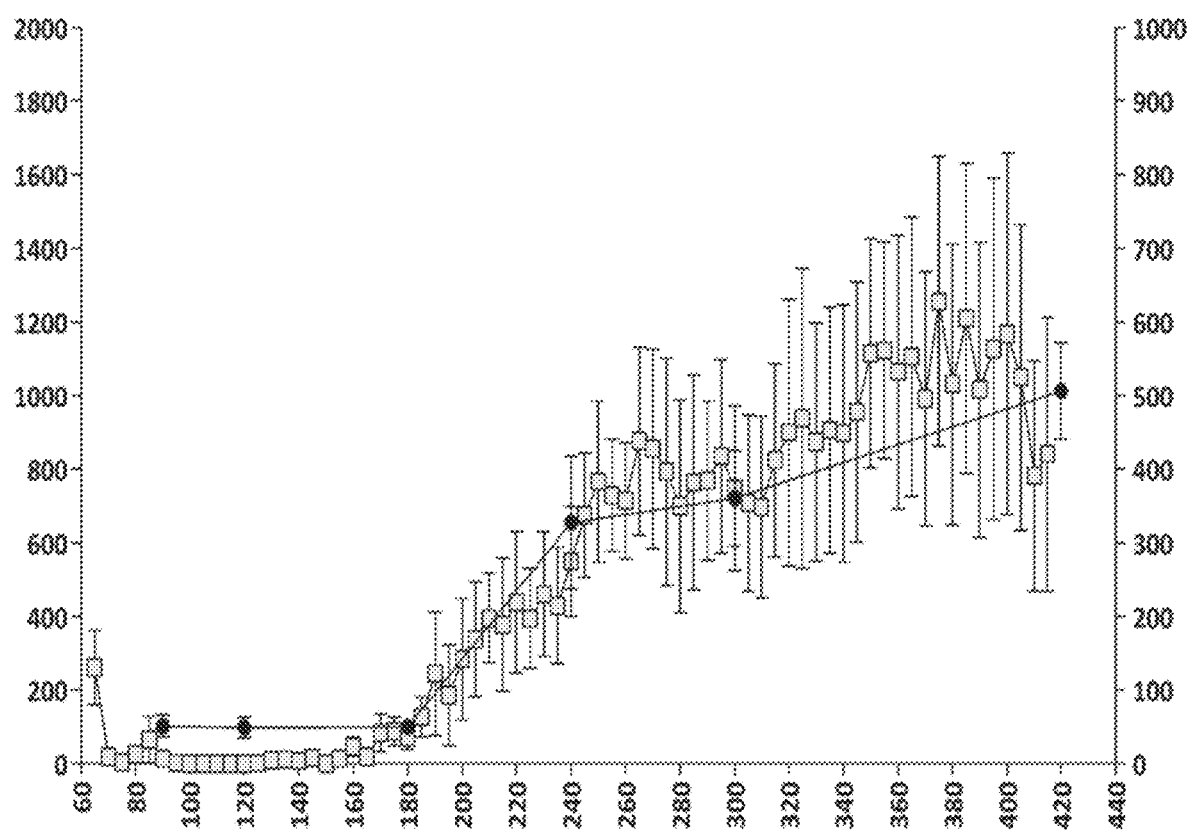
FIG. 4 and FIG. 5: Relationships between plasma concentrations of compound (Id) and compound (I) and hyperactivity induced by compound (Id) (100 µg/kg, p.o.) (FIG. 4) and the corresponding relationship between plasma apomorphine concentrations and hyperactivity induced by apomorphine (3 mg/kg, s.c.) (FIG. 5).
Figure 5:
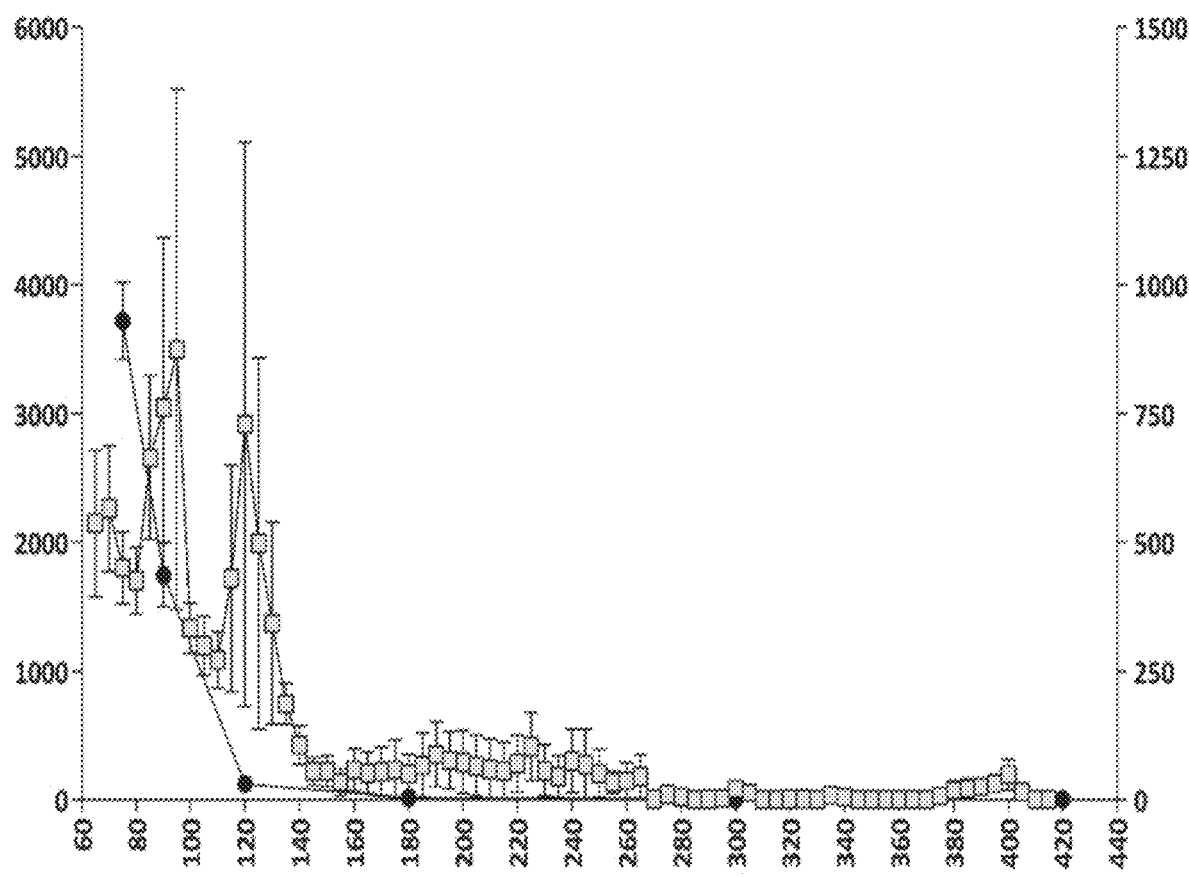

Compound (Id) has further been explored in the rat locomotor activity assay according to Example 10. The assay demonstrated a dopaminergic effect obtained after oral administration of compound (Id) c.f. FIGS. 2, 3 and 4. The fact that the compound of formula (Id) possesses no in vitro dopaminergic activity c.f. Example 7 and Table 3, further indicates that the effect of compound (Id) in the rat locomotor activity assay is obtained by conversion of compound (Id) to compound (I).

Finally; an important issue associated with the prior art compound (Ib) is that this compound is an agonist of the 5-HT2B receptor. Since 5-HT2B receptor agonists have been linked to pathogenesis of valvular heart disease (VHD) after long term exposure, such compounds are not suitable for use in the treatment of chronical diseases (Rothman et al., Circulation (2000), 102: 2836-2841; and Cavero and Guillon, J. Pharmacol. Toxicol. Methods (2014), 69: 150-161). Thus, a further advantage of the compounds of the invention is that these are not 5-HT2B agonists c.f. Example 8 and Table 7.

The compound of formula (Id) is useful in the treatment of neurodegenerative diseases and disorders such as Parkinson's disease and/or other conditions for which treatment with a dopamine agonist is therapeutically beneficial. The compound, being suitable for oral administration has the potential of providing a new treatment paradigm in Parkinson's Disease.

WO2019101917 discloses compound (Id), methods for producing the compound (Id) and uses of the compound (Id).

The present invention provides new solid forms of compound (Id).

The compound of formula (Id) has three pKa values which may be leading to different major species of ionization as depicted in the Table 1 below.

TABLE 1

Various major species of ionization of compound (Id)

pH < 2.8

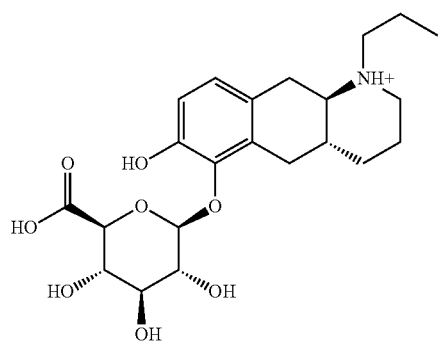

2.8 < pH < 8.8

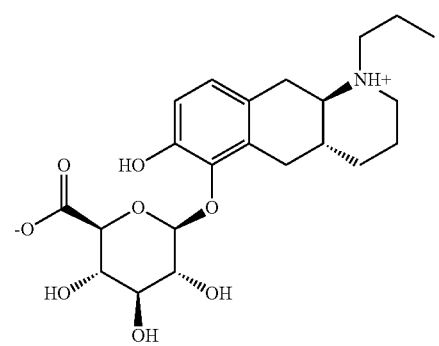

8.8 < pH < 10.1

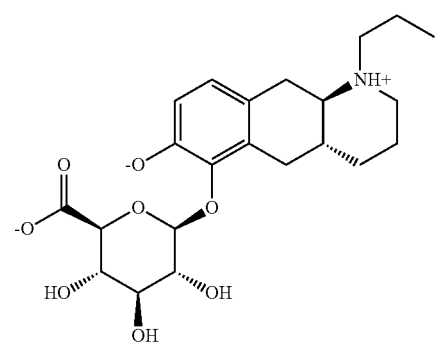

TABLE 1-continued

Various major species of ionization of compound (Id)

pH > 10.1

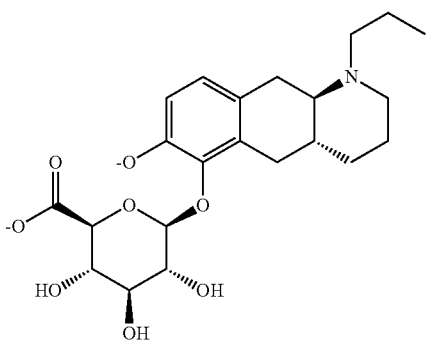

At physiological pH, the compound exists mainly on zwitterion form. The current invention comprises seven solid forms of the zwitterion which have been identified and characterized.

At low pH, acid addition salts can be formed with inorganic and/or organic acids on the nitrogen atom of the compound (Id). The present invention comprises two acid addition salts which have been identified and characterized. These are the hydrochloride salt and the hydrobromide salt.

At high pH, base addition salts can be formed with inorganic and/or organic bases on the acidic groups of the compound of formula (Id). The present invention comprises two base addition salts which have been identified and characterized. These are the sodium salt and the potassium salt.

The scope of the invention encompasses solid forms of compound (Id) selected from solid forms of the zwitterion of compound (Id); alkali metal salts of the compound of formula (Id); and halogen salts of the compound of formula (Id). The solid forms of the invention comprise hydrate and anhydrite forms and various polymorphic forms.

Exemplified solid forms encompassed by the invention and method for obtaining said forms are described in brief below.

Dihydrate (DH1) of the zwitterion of compound (Id) formed by crystallization at room temperature from a Water:EtOH mixture containing 10-30% vol. water, preferably 15-20%.

Anhydrate (AH1) of the zwitterion of compound (Id) obtained by crystallization at room temperature from Water:EtOH mixtures containing 1-5% vol. water, or by crystallization at 37° C. or higher temperature from Water:EtOH mixtures containing 10% vol. water.

Heptahydrate (HH) of the zwitterion of compound (Id) formed by crystallization of compound (Id) from water.

Forms A, B and C of the zwitterion of compound (Id), which forms are all non-stoichiometric hydrates. Form A was obtained by storage of HH at room temperature at ~5% RH. Form B was obtained by storage of HH at room temperature at ~10% RH. Form C was obtained by storage of HH at room temperature at ~15% RH.

Monohydrate (MH1) of the zwitterion of compound (Id). MH1 was obtained by heating of DH1 to 105° C. and subsequent water sorption at ambient conditions. MH1 can also obtained by drying DH1 at room temperature to 0% RH, and subsequent water sorption at ambient conditions.

The potassium salt of compound (Id), sodium salt form 1 and sodium salt form 2 of compound (Id) were prepared according to the experimental section herein.

Hydrochloride and hydrobromide salts of compound (Id) were prepared according to the experimental section herein.

In one specific embodiment, the solid forms as provided by the invention are crystalline forms.

In one embodiment, the invention provides solid forms that when analysed with XRPD shows at least one XRPD peak, as shown in FIGS. 8-19, or included in Table 2. In one specific embodiment, each of said solid form when analysed with XRPD shows respectively at least 5 or more of the peaks of the 2θ-angles included in Table 2 for each specific form ±0.2° 2θ, such as at least 5 to 10 peaks, e.g. 6, 7, 8, or 9 peaks of the 2θ-angles included in Table 2 for each specific form ±0.2° 2θ, or such as at least 10 to 15 peaks, e.g. such as 11, 12, 13, or 14 peaks of the 2θ-angles included in Table 2±0.2° 2θ for each specific form.

In an additional specific embodiment, each of said solid form is characterized respectively by at least 5 or more of the peaks of the 2θ-angles included in Table 2 group (a) for each specific form ±0.2° 2θ, such as at least 5 to 10 peaks, e.g. 6, 7, 8, or 9 peaks of the 2θ-angles included in Table 2 for each specific form ±0.2° 2θ, or such as at least 10 to 15 peaks, e.g. such as 11, 12, 13, or 14 peaks of the 2θ-angles included in Table 2±0.2° 2θ for each specific form.

In another more specific embodiment, each of said solid form when analysed with XRPD shows respectively at least 5 or more of the peaks of the 2θ-angles included in Table 2 for each specific form ±0.1° 2θ, such as at least 5 to 10 peaks, e.g. 6, 7, 8, or 9 peaks of the 2θ-angles included in Table 2 for each specific form ±0.1° 2θ, or such as at least 10 to 15 peaks, e.g. such as 11, 12, 13, or 14 peaks of the 2θ-angles included in Table 2±0.1° 2θ for each specific form.

In a further specific embodiment, each of said solid form is characterized respectively by at least 5 or more of the peaks of the 2θ-angles included in Table 2 group (a) for each specific form ±0.2° 2θ, such as at least 5 to 10 peaks, e.g. 6, 7, 8, or 9 peaks of the 2θ-angles included in Table 2 for each specific form ±0.1° 2θ, or such as at least 10 to 15 peaks, e.g. such as 11, 12, 13, or 14 peaks of the 2θ-angles included in Table 2±0.1° 2θ for each specific form.

In one embodiment, the invention provides solid forms of the present invention with XRPD as shown in FIGS. 8-19.

In one embodiment, the solid forms of the present invention are in a purified form. The term "purified form" is intended to indicate that the solid form is essentially free of other compounds or other forms of the same compound, as the case may be.

In one specific embodiment the solid form of the invention is a purified form of the heptahydrate of the zwitterion of compound (Id), the dihydrate of the zwitterion of compound (Id), or an alkali metal salt of the of compound of formula (Id), preferably a potassium salt of the compound of formula (Id).

In an even more specific embodiment of the present invention, the solid form is a purified form of the dihydrate of the zwitterion of compound (Id).

Methods for preparation of the exemplified solid forms are given in the Experimental section.

EMBODIMENTS OF THE INVENTION

In the following, embodiments of the invention are disclosed. The first embodiment is denoted E1, the second embodiment is denoted E2 and so forth:

E1. A solid form of the compound of formula (Id)

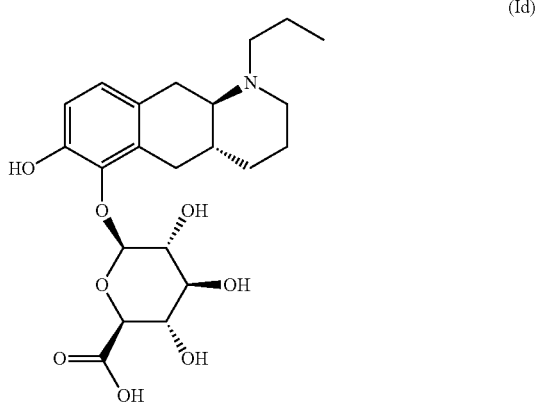 [SMILES: CCCN1CCC[C@@H]2Cc3c(ccc(O)c3O[C@@H]3O[C@H](C(=O)O)[C@@H](O)[C@H](O)[C@H]3O)C[C@H]21]

(Id)

wherein said solid form is selected from:
 a) a solid form of the zwitterion of compound (Id);
 b) an alkali metal salt of the compound of formula (Id): and
 c) a halogen salt of the compound of formula (Id).

E2. The solid form according to embodiment 1, wherein said solid form is a) a solid form of the zwitterion of compound (Id).

E3. The solid form according to any of embodiments 1-2, wherein said solid form is a dihydrate (DH1) of the zwitterion of compound (Id).

E4. The solid form according to embodiment 3, wherein said solid form has a crystal form characterized by an XRPD obtained using CuKα1 radiation (λ=1.5406 Å) showing peaks at the following 2θ-angles: 10.4, 11.6, 12.3, 13.1, 13.6, 14.3, 15.6, 16.0, 16.8 and 18.5°.

E5. The solid form according to any of embodiments 3-4, wherein said solid form has a crystal form characterized by an XRPD obtained using CuKα1 radiation (λ=1.5406 Å) showing peaks at the following 2θ-angles: 12.3, 13.1, 13.6, 16.0, 16.8, 18.5, 18.9, 19.4, 20.5, 21.4, 23.5, 24.7, 25.4, 26.9 and 28.7°.

E6. The solid form according to any of embodiments 3-5, wherein said solid form has a crystal form characterized by an XRPD obtained using CuKα1 radiation (λ=1.5406 Å) as depicted in FIG. 8a.

E7. The solid form according to any of embodiments 1-2, wherein said solid form is an anhydrate of the zwitterion of compound (Id).

E8. The solid form according to any of embodiments 1-2 and 7, wherein said solid form is an anhydrate (AH1) of the zwitterion of compound (Id).

E9. The solid form according to embodiment 8, wherein said solid form has a crystal form characterized by an XRPD obtained using CuKα1 radiation (λ=1.5406 Å) showing peaks at the following 2θ-angles: 8.5, 11.1, 12.4, 12.9, 15.6, 16.7, 18.9, 19.3, 20.0 and 21.2°.

E10. The solid form according to any of embodiments 8-9, wherein said solid form has a crystal form characterized by an XRPD obtained using CuKα1 radiation (λ=1.5406 Å) showing peaks at the following 2θ-angles: 8.5, 12.4, 12.9, 15.6, 16.7, 18.9, 19.3, 20.0, 21.2, 21.5, 22.2, 23.0, 24.2, 27.3 and 28.3°.

E11. The solid form according to any of embodiments 8-10, wherein said solid form has a crystal form characterized by an XRPD obtained using CuKα1 radiation (λ=1.5406 Å) as depicted in FIG. 9a.

E12. The solid form according to any of embodiments 1-2, wherein said solid form is a heptahydrate (HH) of the zwitterion of compound (Id).

E13. The solid form according to embodiment 12, wherein said solid form has a crystal form characterized by an XRPD obtained using CuKα1 radiation (λ=1.5406 Å) showing peaks at the following 2θ-angles: 7.0, 8.6, 10.2, 11.1, 11.9, 13.4, 14.0, 14.5, 17.0 and 17.4°.

E14. The solid form according to any of embodiments 12-13, wherein said solid form has a crystal form characterized by an XRPD obtained using CuKα1 radiation (λ=1.5406 Å) showing peaks at the following 2θ-angles: 7.0, 8.6, 10.2, 11.1, 11.9, 14.0, 17.0, 22.2, 25.9, 27.3, 28.3, 30.8, 34.0, 34.8 and 35.2°.

E15. The solid form according to any of embodiments 12-14, wherein said solid form has a crystal form characterized by an XRPD obtained using CuKα1 radiation (λ=1.5406 Å) as depicted in FIG. 10a.

E16. The solid form according to any of embodiments 1-2, wherein said solid form is form A of the zwitterion of compound (Id).

E17. The solid form according to embodiment 16, wherein said solid form has a crystal form characterized by an XRPD obtained using CuKα1 radiation (λ=1.5406 Å) showing peaks at the following 2θ-angles: 7.6, 9.5, 10.0, 11.2, 12.0, 14.3, 14.6, 15.3, 15.5 and 19.3°.

E18. The solid form according to any of embodiments 16-17, wherein said solid form has a crystal form characterized by an XRPD obtained using CuKα1 radiation (λ=1.5406 Å) showing peaks at the following 2θ-angles: 7.6, 9.5, 10.0, 11.2, 12.0, 14.3, 14.6, 15.3, 15.5, 18.7, 19.3, 23.9, 28.8, 33.7 and 38.7°.

Figure 11:
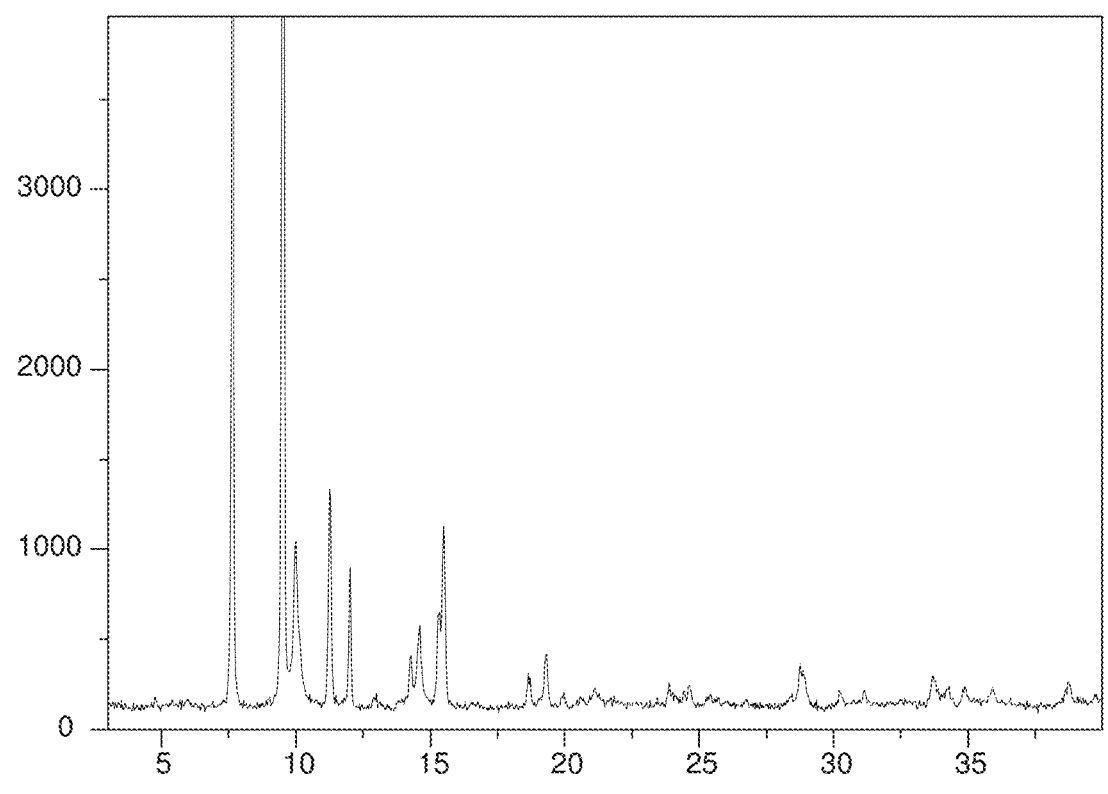

E19. The solid form according to any of embodiments 16-18, wherein said solid form has a crystal form characterized by an XRPD obtained using CuKα1 radiation (λ=1.5406 Å) as depicted in FIG. 11.

E20. The solid form according to any of embodiments 1-2, wherein said solid form is form B of the zwitterion of compound (Id).

E21. The solid form according to embodiment 20, wherein said solid form has a crystal form characterized by an XRPD obtained using CuKα1 radiation (λ=1.5406 Å) showing peaks at the following 2θ-angles: 7.6, 9.0, 10.9, 12.3, 14.3, 15.0, 21.5, 22.1, 22.6 and 23.7°.

E22. The solid form according to any of embodiments 20-21, wherein said solid form has a crystal form characterized by an XRPD obtained using CuKα1 radiation (λ=1.5406 Å) as depicted in FIG. 12.

E23. The solid form according to any of embodiments 1-2, wherein said solid form is form C of the zwitterion of compound (Id).

E24. The solid form according to embodiment 23, wherein said solid form has a crystal form characterized by an XRPD obtained using CuKα1 radiation (λ=1.5406 Å) showing peaks at the following 2θ-angles: 7.5, 8.1, 10.3, 12.6, 13.5, 13.8, 14.9, 17.5, 18.5 and 20.6°.

E25. The solid form according to any of embodiments 23-24, wherein said solid form has a crystal form characterized by an XRPD obtained using CuKα1 radiation (λ=1.5406 Å) showing peaks at the following 2θ-angles: 7.5, 8.1, 10.3, 12.6, 13.5, 13.8, 14.9, 17.5, 18.5, 20.6, 21.6, 22.9, 23.1, 24.0 and 25.4°.

E26. The solid form according to any of embodiments 23-25, wherein said solid form has a crystal form characterized by an XRPD obtained using CuKα1 radiation (λ=1.5406 Å) as depicted in FIG. 13.

E27. The solid form according to any of embodiments 1-2, wherein said solid form is a monohydrate (MH1) of the zwitterion of compound (Id).

E29. The solid form according to embodiment 27, wherein said solid form has a crystal form characterized by an XRPD obtained using CuKα1 radiation (λ=1.5406 Å) showing peaks at the following 2θ-angles: 9.2, 10.2, 11.8, 12.6, 13.6, 15.7, 16.0, 16.5, 17.5 and 18.1°.

E30. The solid form according to any of embodiments 27-28, wherein said solid form has a crystal form characterized by an XRPD obtained using CuKα1 radiation (λ=1.5406 Å) showing peaks at the following 2θ-angles: 9.2, 10.2, 11.8, 12.6, 13.6, 16.0, 16.5, 17.5, 18.1, 18.7, 19.6, 22.9, 24.7, 25.4 and 26.0°.

E31. The solid form according to any of embodiments 27-29, wherein said solid form has a crystal form characterized by an XRPD obtained using CuKα1 radiation (λ=1.5406 Å) as depicted in FIG. 14.

E32. The solid form according to embodiment 1, wherein said solid form is b) an alkali metal salt of the compound of formula (Id).

E33. The solid form according to any of embodiments 1 and 32, wherein said salt is a potassium salt of the compound of formula (Id).

E34. The solid form according to embodiment 33, wherein said potassium salt has a crystal form characterized by an XRPD obtained using CuKα1 radiation (λ=1.5406 Å) showing peaks at the following 2θ-angles: 3.0, 9.0, 12.6, 13.6, 15.0, 17.1, 18.0, 18.4, 18.8 and 19.4°.

E35. The solid form according to any of embodiments 33-34, wherein said potassium salt has a crystal form characterized by an XRPD obtained using CuKα1 radiation (λ=1.5406 Å) showing peaks at the following 2θ-angles: 3.0, 9.0, 12.6, 13.6, 15.0, 18.0, 19.4, 21.8, 24.7, 27.1, 29.8, 33.3, 35.6, 38.6 and 39.6°.

E36. The solid form according to any of embodiments 33-35, wherein said potassium salt has a crystal form characterized by an XRPD obtained using CuKα1 radiation (λ=1.5406 Å) as depicted in FIG. 15.

E37. The solid form according to any of embodiments 1 and herein said salt is a sodium salt of the compound of formula (Id).

E38. The solid form according to embodiment 37, wherein said sodium salt is sodium salt form 1 of the compound of formula (Id).

E39. The solid form according to any of embodiments 37-38, wherein said sodium salt has a crystal form characterized by an XRPD obtained using CuKα1 radiation (λ=1.5406 Å) showing peaks at the following 2θ-angles: 5.9, 8.9, 11.9, 12.8, 13.8, 14.9, 17.7, 18.6, 19.0 and 19.5°.

E40. The solid form according to any of embodiments 38-39, wherein said sodium salt has a crystal form characterized by an XRPD obtained using CuKα1 radiation (λ=1.5406 Å) showing peaks at the following 2θ-angles: 8.9, 12.8, 13.8, 14.9, 17.7, 18.6, 19.0, 19.5, 21.5, 21.8, 22.2, 22.6, 22.9, 23.4 and 25.1°.

E41. The solid form according to any of embodiments 38-40, wherein said sodium salt has a crystal form characterized by an XRPD obtained using CuKα1 radiation (λ=1.5406 Å) as depicted in FIG. 16.

E42. The solid form according to embodiment 37, wherein said sodium salt is sodium salt form 2 of the compound of formula (Id).

E43. The solid form according to any of embodiments 37 and 42, wherein said sodium salt has a crystal form characterized by an XRPD obtained using CuKα1 radiation (λ=1.5406 Å) showing peaks at the following 2θ-angles: 5.6, 8.5, 12.6, 13.6, 14.1, 15.0, 16.7, 17.0, 18.8 and 19.8°.

E44. The solid form according to any of embodiments 37 and 42-43, wherein said sodium salt has a crystal form characterized by an XRPD obtained using CuKα1 radiation (λ=1.5406 Å) showing peaks at the following 2θ-angles: 5.6, 8.5, 12.6, 13.6, 14.1, 15.0, 17.0, 18.8, 19.8, 21.0, 23.4, 28.5, 34.3, 37.3 and 38.5°.

E45. The solid form according to any of embodiments 37 and 42-44, wherein said sodium salt has a crystal form characterized by an XRPD obtained using CuKα1 radiation (λ=1.5406 Å) as depicted in FIG. 17.

E46. The solid form according to embodiment 1, wherein said solid form is a halogen salt of the compound of formula (Id).

E47. The solid form according to any of embodiments 1 and 46, wherein said salt is a hydrochloride salt of the compound of formula (Id).

E48. The solid form according to embodiment 47, wherein said hydrochloride salt has a crystal form characterized by an XRPD obtained using CuKα1 radiation (λ=1.5406 Å) showing peaks at the following 2θ-angles: 5.7, 7.3, 10.6, 13.3, 15.3, 15.4, 16.2, 20.1, 22.5 and 23.0°.

E49. The solid form according to any of embodiments 47-48, wherein said hydrochloride salt has a crystal form characterized by an XRPD obtained using CuKα1 radiation (λ=1.5406 Å) showing peaks at the following 2θ-angles: 5.1, 5.7, 7.3, 10.6, 13.3, 15.3, 15.4, 16.2, 16.7, 18.1, 20.1, 22.5, 23.0, 23.6 and 23.8°.

E50. The solid form according to any of embodiments 47-49, wherein said hydrochloride salt has a crystal form characterized by an XRPD obtained using CuKα1 radiation (λ=1.5406 Å) as depicted in FIG. 18.

E51. The solid form according to any of embodiments 1 and 46, wherein said salt is a hydrobromide salt of the compound of formula (Id).

E52. The solid form according to embodiment 51, wherein said hydrobromide salt has a crystal form characterized by an XRPD obtained using CuKα1 radiation (λ=1.5406 Å) showing peaks at the following 2θ-angles: 12.5, 13.9, 14.5, 15.6, 18.6, 18.9, 19.8, 21.3, 22.0 and 22.4°.

E53. The solid form according to any of embodiments 51-52, wherein said hydrobromide salt has a crystal form characterized by an XRPD obtained using CuKα1 radiation (λ=1.5406 Å) showing peaks at the following 2θ-angles: 12.5, 13.9, 14.5, 15.6, 18.6, 18.9, 19.8, 21.3, 22.0, 22.4, 23.3, 24.4, 25.5, 28.2 and 28.9°.

E54. The solid form according to any of embodiments 51-53, wherein said hydrobromide salt has a crystal form characterized by an XRPD obtained using CuKα1 radiation (λ=1.5406 Å) as depicted in FIG. 19.

E55. The solid form of the compound of formula (Id) according to any of embodiments 1-54, for use in therapy.

E56. The solid form of the compound of formula (Id) according to any of embodiments 1-54, for use as a medicament.

E57. The solid form of the compound of formula (Id) according to embodiment 56, wherein said medicament is an oral medicament such as a tablet or a capsule for oral administration.

E58. A pharmaceutical composition comprising a therapeutically effective amount of the solid form of the compound of formula (Id) according to any of embodiments 1-54, and one or more pharmaceutically acceptable excipients.

E59. The pharmaceutical composition according to embodiment 58, wherein said pharmaceutical composition is for oral administration.

E60. The pharmaceutical composition according to any of embodiments 58-59, wherein said pharmaceutical composition is an oral pharmaceutical composition.

E61. The pharmaceutical composition according to any of embodiments 58-60, wherein said pharmaceutical composition is a solid oral dosage form.

E62. The pharmaceutical composition according to any of embodiments 58-61, wherein said pharmaceutical composition is a tablet or a capsule for oral administration.

E63. The pharmaceutical composition according to any of embodiments 58-62, wherein said pharmaceutical composition further comprises another agent which is useful in the treatment of a neurodegenerative disease or disorder such as Parkinson's disease.

E64. The pharmaceutical composition according to any of embodiments 58-63, wherein said pharmaceutical composition further comprises a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or an antibody targeting alpha-synuclein, Tau or A-beta protein.

E65. A solid form of the compound of formula (Id) according to any of embodiments 1-54, for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

E66. The solid form of the compound of formula (Id) according to any of embodiments 1-54, for use in the treatment according to embodiment 65, wherein said neurodegenerative disease or disorder is Parkinson's Disease.

E67. The solid form of the compound of formula (Id) according to any of embodiments 1-54, for use in the treatment according to any of embodiments 65-66, wherein said compound is to be used in combination with another agent which is useful in the treatment of a neurodegenerative disease or disorder such as Parkinson's disease.

E68. The solid form of the compound of formula (Id) according to any of embodiments 1-54, for use in the treatment according to any of embodiments 66-67, wherein said compound is to be used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E69. The solid form of the compound of formula (Id) according to any of embodiments 1-54, for use in the treatment according to any of embodiments 66-68, wherein said treatment is performed by oral administration of said compound.

E70. The solid form of the compound of formula (Id) according to any of embodiments 1-54, for use in the treatment according to any of embodiments 66-69, wherein said compound is comprised in an oral pharmaceutical composition such as a tablet or a capsule for oral administration.

E71. A method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of solid form of the compound of formula (Id) according to any of embodiments 1-54, to a patient in need thereof.

E72. The method according to embodiment 71, wherein said neurodegenerative disease or disorder is Parkinson's Disease.

E73. The method according to any of embodiments 71-72, wherein said compound or pharmaceutically acceptable salt thereof according to any of embodiments 1-54, is used in combination with another agent which is useful in the treatment of a neurodegenerative disease or disorder such as Parkinson's disease.

E74. The method according to any of embodiments 72-73, wherein said compound or pharmaceutically acceptable salt thereof according to any of embodiments 1-23, is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E75. The method according to any of embodiments 71-74, wherein said administration is performed by the oral route.

E76. The method according to any of embodiments 71-75, wherein said compound or pharmaceutically acceptable salt thereof according to any of embodiments 1-23 is comprised in an oral pharmaceutical composition such as a tablet or a capsule for oral administration.

E77. Use of solid form of the compound of formula (Id) according to any of embodiments 1-54, in the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

E78. The use according to embodiment 77, wherein said neurodegenerative disease or disorder is Parkinson's Disease.

E79. The use according to any of embodiments 77-78, wherein said medicament is used in combination with another agent which is useful in the treatment of a neurodegenerative disease or disorder such as Parkinson's disease.

E80. The use according to any of embodiments 78-79, wherein said medicament is used in combination with a compound selected from the group consisting of L-DOPA, droxidopa, foliglurax a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E81. The use according to any of embodiments 77-80, wherein said medicament is an oral medicament such as a tablet or a capsule for oral administration.

Items

The following items serve to further define the invention.

Item 1. A solid form of the compound of formula (Id)

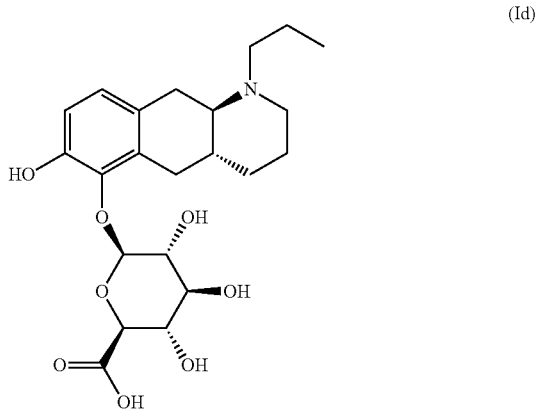 [SMILES: CCCN1CCC[C@@H]2Cc3c(ccc(O)c3O[C@@H]3O[C@H](C(=O)O)[C@@H](O)[C@H](O)[C@H]3O)C[C@H]21]

(Id)

wherein said solid form is selected from:
a) a form of the zwitterion of compound (Id);
b) an alkali metal salt of the compound of formula (Id); and
c) a halogen salt of the compound of formula (Id).

Item 2. The solid form according to item 1, wherein said solid form is a crystalline form.

Item 3. The solid form according to any one of items 1-2, wherein said solid form is a solid form of the zwitterion of compound (Id).

Item 4. The solid form according to any one of items 1-3, wherein said solid form is a hydrate of the zwitterion of compound (Id).

Item 5. The solid form according to any one of items 1-4, wherein said solid form is a hydrate solid form of the zwitterion of compound (Id) selected from the group consisting of a monohydrate form, a dihydrate form and a heptahydrate form.

Item 6. The solid form according to any one of items 1-5, wherein said solid form is a hydrate of the zwitterion of compound (Id) selected from the group consisting of the dihydrate form and the heptahydrate form.

Item 7. The solid form according to any one of items 1-6, wherein said solid form is the dihydrate (DH1) of the zwitterion of compound (Id).

Item 8. The solid form according to item 7, wherein said solid form is a crystal form characterized by an x-ray powder diffraction pattern as obtained using CuKα1 radiation (λ=1.5406 Å) comprising peaks at the following 2θ-angles±0.2° 2θ: 10.4, 11.6, 12.3 and 13.1 and 13.6°.

Item 9. The solid form according to any one of items 7-8, wherein said solid form is a crystal form characterized by an x-ray powder diffraction pattern as obtained using CuKα1 radiation (λ=1.5406 Å) comprising peaks at the following 2θ-angles±0.1° 2θ: 10.4, 11.6, 12.3, 13.1 and 13.6°.

Item 10. The solid form according to any one of items 8-9, wherein said x-ray powder diffraction pattern further comprises one or more peaks selected from the group consisting of peaks at the following 2θ-angles±0.2° 2θ: 14.3, 15.6, 16.0, 16.8 and 18.5°.

Item 11 The solid form according to any one of items 8 and 10, wherein said solid form is a crystal form characterized by an x-ray powder diffraction pattern as obtained using CuKα1 radiation (λ=1.5406 Å) comprising peaks at the following 2θ-angles±0.2° 2θ:10.4, 11.6, 12.3, 13.1, 13.6, 14.3, 15.6, 16.0, 16.8 and 18.5°.

Item 12. The solid form according to any one of items 9-10, wherein said solid form is a crystal form characterized by an x-ray powder diffraction pattern as obtained using CuKα1 radiation (λ=1.5406 Å) comprising peaks at the following 2θ-angles±0.1° 2θ:10.4, 11.6, 12.3, 13.1, 13.6, 14.3, 15.6, 16.0, 16.8 and 18.5°.

Item 13. The solid form according to any one of items 7, 8, 10 and 11, wherein said solid form is a crystal form characterized by an x-ray powder diffraction pattern as obtained using CuKα1 radiation (λ=1.5406 Å) comprising peaks at the following 2θ-angles±0.2° 2θ: 10.4, 11.6, 12.3, 13.1, 13.6, 14.3, 15.6, 16.0, 16.8 and 18.5°, Item 14. The solid form according to any one of items 7, 9 and 12, wherein said solid form is a crystal form characterized by an x-ray powder diffraction pattern as obtained using CuKα1 radiation (λ=1.5406 Å) comprising peaks at the following 2θ-angles±0.1° 2θ: 10.4, 11.6, 12.3, 13.1, 13.6, 14.3, 15.6, 16.0, 16.8 and 18.5°.

Item 15. The solid form according to any one of items 7, 8, 10, 11 and 13, wherein said solid form is a crystal form characterized by an x-ray powder diffraction pattern as obtained using CuKα1 radiation (λ=1.5406 Å) comprising peaks at the following 2θ-angles±0.2° 2θ: 12.3, 13.1, 13.6, 16.0, 16.8, 18.5, 18.9, 19.4, 20.5, 21.4, 23.5, 24.7, 25.4, 26.9 and 28.7°.

Item 16. The solid form according to any one of items 7, 9 and 14, wherein said solid form is a crystal form characterized by an x-ray powder diffraction pattern as obtained using CuKα1 radiation (λ=1.5406 Å) comprising peaks at the following 2θ-angles±0.1° 2θ: 12.3, 13.1, 13.6, 16.0, 16.8, 18.5, 18.9, 19.4, 20.5, 21.4, 23.5, 24.7, 25.4, 26.9 and 28.7°

Item 17. The solid form according to any one of items 7-16, wherein said solid form is a crystal form characterized by an x-ray powder diffraction pattern as obtained using CuKα1 radiation (λ=1.5406 Å) essentially as depicted in FIG. 8a.

Item 8, The solid form according to any one of items 7-17, exhibiting a weight loss of about 7.6% w/w compared to the initial weight when heated from about 30° C. to about 150° C. (heating rate 10° C./min), such as measured using thermogravimetric analysis.

Item 19. The solid form according to any one of items 7-18, wherein said solid form is a crystal form characterized by thermogravimetric analysis (using a heating rate 10° C./min) essentially as depicted in FIG. 8b.

Item 20. The solid form according to any one of items 1-3, wherein said solid form is an anhydrate of the zwitterion of compound (Id).

Item 21. The solid form according to any one of items 1-3 and 20, wherein said solid form is the anhydrate (AH1) of the zwitterion of compound (Id).

Item 22. The solid form according to any one of items 20-22, wherein said solid form is a crystal form characterized by an x-ray powder diffraction pattern as obtained using CuKα1 radiation (λ=1.5406 Å) comprising peaks at the following 2θ-angles±0.2° 2θ: 8.5, 11.1, 12.4, 12.9, and 15.6°.

Item 23. The solid form according to any one of items 20-22, wherein said solid form is a crystal form characterized by an x-ray powder diffraction pattern as obtained using CuKα1 radiation (λ=1.5406 Å) comprising peaks at the following 2θ-angles±0.1° 2θ: 8.5, 11.1, 12.4, 12.9, and 15.6°.

Item 24. The solid form according to any one of items 22-23, wherein said x-ray powder diffraction pattern further comprises one or more peaks selected from the group consisting of peaks at the following 2θ-angles±0.2° 2θ: 16.7, 18.9, 19.3, 20.0 and 21.2°.

Item 25. The solid form according to any one of items 20-22 and 24, wherein said solid form is a crystal form characterized by an x-ray powder diffraction pattern as obtained using CuKα1 radiation (λ=1.5406 Å) comprising peaks at the following 2θ-angles±0.2° 2θ: 8.5, 11.1, 12.4, 12.9, 15.6, 16.7, 18.9, 19.3, 20.0 and 21.2°.

Item 26. The solid form according to any one of items 20-25, wherein said solid form is a crystal form characterized by an x-ray powder diffraction pattern as obtained using CuKα1 radiation (λ=1.5406 Å) comprising peaks at the following 2θ-angles±0.1° 2θ: 8.5, 11.1, 12.4, 12.9, 15.6, 16.7, 18.9, 19.3, 20.0 and 21.2°.

Item 27. The solid form according to any one of items 20-25, wherein said solid form is a crystal form characterized by an x-ray powder diffraction pattern as obtained using CuKα1 radiation (λ=1.5406 Å) comprising peaks at the following 2θ-angles±0.2° 2θ: 8.5, 12.4, 12.9, 15.6, 16.7, 18.9, 19.3, 20.0, 21.2, 21.5, 22.2, 23.0, 24.2, 27.3 and 28.3°.

Item 28. The solid form according to any one of items 20-27, wherein said solid form is a crystal form characterized by an x-ray powder diffraction pattern as obtained using CuKα1 radiation (λ=1.5406 Å) comprising peaks at the following 2θ-angles±0.1° 2θ: 8.5, 12.4, 12.9, 15.6, 16.7, 18.9, 19.3, 20.0, 21.2, 21.5, 22.2, 23.0, 24.2, 27.3 and 28.3°.

Item 29. The solid form according to any one of items 20-28, wherein said solid form is a crystal form characterized by an x-ray powder diffraction pattern as obtained using CuKα1 radiation (λ=1.5406 Å) essentially as depicted in FIG. 9a.

Item 30. The solid form according to any one of items 20-29, exhibiting a weight loss of less than 1% w/w compared to the initial weight when heated from about 30° C. to about 150° C. (heating rate 10° C./min), such as measured using thermogravimetric analysis.

Item 31 The solid form according to any one of items 20-30, wherein said solid form is a crystal form characterized by thermogravimetric analysis (using a heating rate 10° C./min) essentially as depicted in FIG. 9b.

Item 32. The solid form according to any one of items 1-6, wherein said solid form is a heptahydrate (HH) of the zwitterion of compound (Id).

Item 33. The solid form according to item 32, wherein said solid form is a crystal form characterized by an x-ray powder diffraction pattern as obtained using CuKα1 radiation (λ=1.5406 Å) comprising peaks at the following 2θ-angles±0.2° 2θ: 7.0, 8.6, 10.2, 11.1 and 11.9°.

Item 34. The solid form according to any one of items 32-33, wherein said solid form is a crystal form characterized by an x-ray powder diffraction pattern as obtained using CuKα1 radiation (λ=1.5406 Å) comprising peaks at the following 2θ-angles±0.1° 2θ: 7.0, 8.6, 10.2, 11.1 and 11.9°.

Item 35. The solid form according to any one of items 33-34, wherein said x-ray powder diffraction pattern further comprises one or more peaks selected from the group consisting of peaks at the following 2θ-angles±0.2° 2θ: 13.4, 14.0, 14.5, 17.0 and 17.4°.

Item 36. The solid form according to any one of items 32-33 and 35, wherein said solid form is a crystal form characterized by an x-ray powder diffraction pattern as obtained using CuKα1 radiation (λ=1.5406 Å) comprising peaks at the following 2θ-angles±0.2° 2θ: 7.0, 8.6, 10.2, 11.1, 11.9, 13.4, 14.0, 14.5, 17.0 and 17.4°.

Item 37. The solid form according to any one of items 32-36, wherein said solid form is a crystal form characterized by an x-ray powder diffraction pattern as obtained using CuKα1 radiation (λ=1.5406 Å) comprising peaks at the following 2θ-angles±0.1° 2θ: 7.0, 8.6, 10.2, 11.1, 11.9, 13.4, 14.0, 14.5, 17.0 and 17.4°, Item 38. The solid form according to any one of items 32-33 and 35-36, wherein said solid form is a crystal form characterized by an x-ray powder diffraction pattern as obtained using CuKα1 radiation (λ=1.5406 Å) comprising peaks at the following 2θ-angles±0.2° 2θ: 7.0, 8.6, 10.2, 11.1, 11.9, 14.0, 17.0, 22.2, 25.9, 27.3, 28.3, 30.8, 34.0, 34.8 and 35.2°, Item 9, The solid form according to any one of items 32-38, wherein said solid form is a crystal form characterized by an x-ray powder diffraction pattern as obtained using CuKα1 radiation (λ=1.5406 Å) comprising peaks at the following 2θ-angles±0.1° 2θ: 7.0, 8.6, 10.2, 11.1, 11.9, 14.0, 17.0, 22.2, 25.9, 27.3, 28.3, 30.8, 34.0, 34.8 and 35.2°.

Item 40. The solid form according to any one of items 32-39, wherein said solid form is a crystal form characterized by an x-ray powder diffraction pattern as obtained using CuKα1 radiation (λ=1.5406 Å) essentially as depicted in FIG. 10a.

Item 41. The solid form according to any one of items 32-40, exhibiting a weight loss of about 21% w/w compared to the initial weight when heated from about 20° C. to about 150° C. (heating rate 10° C./min), such as measured using thermogravimetric analysis.

Item 42. The solid form according to any one of items 32-41, wherein said solid form is a crystal form characterized by thermogravimetric analysis (using a heating rate 10° C./min) essentially as depicted in FIG. 10b.

Item 43. The solid form according to any one of items 1-4, wherein said solid form is form A of the zwitterion of compound (Id).

Item 44. The solid form according to item 43, wherein said solid form is a crystal form characterized by an x-ray powder diffraction pattern as obtained using CuKα1 radiation (λ=1.5406 Å) comprising peaks at the following 2θ-angles±0.2° 2θ: 7.6, 9.5, 10.0, 11.2, and 12.0°.

Item 45. The solid form according to any one of items 43-44, wherein said solid form is a crystal form characterized by an x-ray powder diffraction pattern as obtained using CuKα1 radiation (λ=1.5406 Å) comprising peaks at the following 2θ-angles±0.1° 2θ: 7.6, 9.5, 10.0, 11.2, and 12.0°.

Item 46. The solid form according to any one of items 44-45, wherein said x-ray powder diffraction pattern further comprises one or more peaks selected from the group consisting of peaks at the following 2θ-angles±0.2° 2θ: 14.3, 14.6, 15.3, 15.5 and 19.3°.

Item 47. The solid form according to any one of items 43-44 and 46, wherein said solid form is a crystal form characterized by an x-ray powder diffraction pattern as obtained using CuKα1 radiation (λ=1.5406 Å) comprising peaks at the following 2θ-angles±0.2° 2θ: 7.6, 9.5, 10.0, 11.2, 12.0, 14.3, 14.6, 15.3, 15.5 and 19.3'.

Item 48. The solid form according to any one of items 43-47, wherein said solid form is a crystal form characterized by an x-ray powder diffraction pattern as obtained using CuKα1 radiation (λ=1.5406 Å) comprising peaks at the following 2θ-angles±0.1° 2θ: 7.6, 9.5, 10.0, 11.2, 12.0, 14.3, 14.6, 15.3, 15.5 and 19.3°.

Item 49. The solid form according to any one of items 43-44, and 46-47, wherein said solid form is a crystal form characterized by an x-ray powder diffraction pattern as obtained using CuKα1 radiation (λ=1.5406 Å) comprising peaks at the following 2θ-angles±0.2° 2θ: 7.6, 9.5, 10.0, 11.2, 12.0, 14.3, 14.6, 15.3, 15.5, 18.7, 19.3, 23.9, 28.8, 33.7 and 38.7°.

Item 50. The solid form according to any one of items 43-49, wherein said solid form is a crystal form characterized by an x-ray powder diffraction pattern as obtained using CuKα1 radiation (λ=1.5406 Å) comprising peaks at the following 2θ-angles±0.1° 2θ: 7.6, 9.5, 10.0, 11.2, 12.0, 14.3, 14.6, 15.3, 15.5, 18.7, 19.3, 23.9, 28.8, 33.7 and 38.7°.

Item 51. The solid form according to any one of items 43-50, wherein said solid form is a crystal form characterized by an x-ray powder diffraction pattern as obtained using CuKα1 radiation (λ=1.5406 Å) essentially as depicted in FIG. 11.

Item 52. The solid form according to any one of items 1-4, wherein said solid form is form B of the zwitterion of compound (Id).

Item 53. The solid form according to item 52, wherein said solid form is a crystal form characterized by an x-ray powder diffraction pattern as obtained using CuKα1 radiation (λ=1.5406 Å) comprising peaks at the following 2θ-angles±0.2° 2θ: 7.6, 9.0, 10.9, 12.3 and 14.3°.

Item 54. The solid form according to any one of items 52-53, wherein said solid form is a crystal form characterized by an x-ray powder diffraction pattern as obtained using CuKα1 radiation (λ=1.5406 Å) comprising peaks at the following 2θ-angles±0.1° 2θ: 7.6, 9.0, 10.9, 12.3 and 14.3°.

Item 55. The solid form according to any one of items 53-54, wherein said x-ray powder diffraction pattern further comprises one or more peaks selected from the group consisting of peaks at the following 2θ-angles±0.2° 2θ: 15.0, 21.5, 22.1, 22.6 and 23.7°.

Item 56. The solid form according to any one of items 52-53 and 55, wherein said solid form is a crystal form characterized by an x-ray powder diffraction pattern as obtained using CuKα1 radiation (λ=1.5406 Å) comprising peaks at the following 2θ-angles±0.2° 2θ: 7.6, 9.0, 10.9, 12.3, 14.3, 15.0, 21.5, 22.1, 22.6 and 23.7°.

Item 57. The solid form according to any one of items 52-57, wherein said solid form is a crystal form characterized by an x-ray powder diffraction pattern as obtained using CuKα1 radiation (λ=1.5406 Å) essentially as depicted in FIG. 12.

Item 58. The solid form according to any one of items 1-4, wherein said solid form is form C of the zwitterion of compound (Id).

Item 59. The solid form according to item 58, wherein said solid form is a crystal form characterized by an x-ray powder diffraction pattern as obtained using CuKα1 radiation (λ=1.5406 Å) comprising peaks at the following 2θ-angles±0.2° 2θ: 7.5, 8.1, 10.3, 12.6, and 13.5°.

Item 60. The solid form according to any one of items 58-59, wherein said solid form is a crystal form characterized by an x-ray powder diffraction pattern as obtained using CuKα1 radiation (λ=1.5406 Å) comprising peaks at the following 2θ-angles±0.1° 2θ: 7.5, 8.1, 10.3, 12.6, and 13.5°.

Item 61. The solid form according to any one of items 59-60, wherein said x-ray powder diffraction pattern further comprises one or more peaks selected from the group consisting of peaks at the following 2θ-angles±0.2° 2θ: 13.8, 14.9, 17.5, 18.5 and 20.6°.

Item 62. The solid form according to any one of items 58-59 and 61, wherein said solid form is a crystal form characterized by an x-ray powder diffraction pattern as obtained using CuKα1 radiation (λ=1.5406 Å) comprising peaks at the following 2θ-angles±0.2° 2θ: 7.5, 8.1, 10.3, 12.6, 13.5, 13.8, 14.9, 17.5, 18.5 and 20.6°.

Item 63. The solid form according to any one of items 58-59 and 61-62, wherein said solid form is a crystal form characterized by an x-ray powder diffraction pattern as obtained using CuKα1 radiation (λ=1.5406 Å) comprising peaks at the following 2θ-angles±0.2° 2θ: 7.5, 8.1, 10.3, 12.6, 13.5, 13.8, 14.9, 17.5, 18.5 and 20.6°.

Item 64. The solid form according to any one of items 58-63, wherein said solid form is a crystal form characterized by an x-ray powder diffraction pattern as obtained using CuKα1 radiation (λ=1.5406 Å) comprising peaks at the following 2θ-angles±0.1° 2θ: 7.5, 8.1, 10.3, 12.6, 13.5, 13.8, 14.9, 17.5, 18.5 and 20.6°.

Item 65. The solid form according to any one of items 58-59 and 61-63, wherein said solid form is a crystal form characterized by an x-ray powder diffraction pattern as obtained using CuKα1 radiation (λ=1.5406 Å) comprising peaks at the following 2θ-angles±0.2° 2θ: 7.5, 8.1, 10.3, 12.6, 13.5, 13.8, 14.9, 17.5, 18.5, 20.6, 21.6, 22.9, 23.1, 24.0 and 25.4°.

Item 66. The solid form according to any one of items 58-65, wherein said solid form is a crystal form characterized by an x-ray powder diffraction pattern as obtained using CuKα1 radiation (λ=1.5406 Å) comprising peaks at the following 2θ-angles±0.1° 2θ: 7.5, 8.1, 10.3, 12.6, 13.5, 13.8, 14.9, 17.5, 18.5, 20.6, 21.6, 22.9, 23.1, 24.0 and 25.4°.

Item 67. The solid form according to any one of items 58-66, wherein said solid form is a crystal form characterized by an x-ray powder diffraction pattern as obtained using CuKα1 radiation (λ=1.5406 Å) essentially as depicted in FIG. 13.

Item 68. The solid form according to any one of items 1-6, wherein said solid form is a monohydrate (MH1) of the zwitterion of compound (Id).

Item 69. The solid form according to item 68, wherein said solid form is a crystal form characterized by an x-ray powder diffraction pattern as obtained using CuKα1 radiation (λ=1.5406 Å) comprising peaks at the following 2θ-angles±0.2° 2θ: 9.2, 10.2, 11.8, 12.6, 13.6°.

Item 70. The solid form according to any one of items 68-69, wherein said solid form is a crystal form characterized by an x-ray powder diffraction pattern as obtained using CuKα1 radiation (λ=1.5406 Å) comprising peaks at the following 2θ-angles±0.1° 2θ: 9.2, 10.2, 11.8, 12.6, 13.6°.

Item 71. The solid form according to any one of items 69-70, wherein said x-ray powder diffraction pattern further comprises one or more peaks selected from the group consisting of peaks at the following 2θ-angles±0.2° 2θ: 15.7, 16.0, 16.5, 17.5 and 18.1°.

Item 72. The solid form according to any one of items 68-69 and 71, wherein said solid form is a crystal form characterized by an x-ray powder diffraction pattern as obtained using CuKα1 radiation (λ=1.5406 Å) comprising peaks at the following 2θ-angles±0.2° 2θ: 9.2, 10.2, 11.8, 12.6, 13.6, 15.7, 16.0, 16.5, 17.5 and 18.1°.

Item 73. The solid form according to any one of items 68-72, wherein said solid form is a crystal form characterized by an x-ray powder diffraction pattern as obtained using CuKα1 radiation (λ=1.5406 Å) comprising peaks at the following 2θ-angles±0.1° 2θ: 9.2, 10.2, 11.8, 12.6, 13.6, 15.7, 16.0, 16.5, 17.5 and 18.1°.

Item 74. The solid form according to any one of items 68-69 and 71-72, wherein said solid form is a crystal form characterized by an x-ray powder diffraction pattern as obtained using CuKα1 radiation (λ=1.5406 Å) comprising peaks at the following 2θ-angles±0.2° 2θ: 9.2, 10.2, 11.8, 12.6, 13.6, 16.0, 16.5, 17.5, 18.1, 18.7, 19.6, 22.9, 24.7, 25.4 and 26.0°.

Item 75. The solid form according to any one of items 68-74, wherein said solid form is a crystal form characterized by an x-ray powder diffraction pattern as obtained using CuKα1 radiation (λ=1.5406 Å) comprising peaks at the following 2θ-angles±0.1° 2θ: 9.2, 10.2, 11.8, 12.6, 13.6, 16.0, 16.5, 17.5, 18.1, 18.7, 19.6, 22.9, 24.7, 25.4 and 26.0°.

Item 76. The solid form according to any one of items 68-75, wherein said solid form is a crystal form characterized by an x-ray powder diffraction pattern as obtained using CuKα1 radiation (λ=1.5406 Å) essentially as depicted in FIG. 14a, Item 77. The solid form according to any one of items 68-76, exhibiting a weight loss of about 4% w/w compared to the initial weight when heated from about 20° C. to about 150° C. (heating rate 10° C./min), such as measured using thermogravimetric analysis.

Item 78. The solid form according to any one of items 68-77, wherein said solid form is a crystal form characterized by thermogravimetric analysis (using a heating rate 10° C./min) essentially as depicted in FIG. 14b.

Item 79. The solid form according to any one of items 1 and 2, wherein said solid form is an alkali metal salt of the compound of formula (Id).

Item 80. The solid form according to item 79, wherein said solid form is an alkali metal salt of the compound of formula (Id) selected from the group consisting of a potassium salt and a sodium salt.

Item 81. The solid form according to any of items 79-80, wherein said salt is a potassium salt of the compound of formula (Id).

Item 82. The solid form according to item 81, wherein said potassium salt has a crystal form characterized by an XRPD obtained using CuKα1 radiation (λ=1.5406 Å) comprising peaks at the following 2θ-angles±0.2° 2θ: 3.0, 9.0, 12.6, 13.6, and 15.0°.

Item 83. The solid form according to any one of items 81-82, wherein said potassium salt has a crystal form characterized by an XRPD obtained using CuKα1 radiation (λ=1.5406 Å) comprising peaks at the following 2θ-angles±0.1° 2θ: 3.0, 9.0, 12.6, 13.6, and 15.0°.

Item 84. The solid form according to any one of items 81-83, wherein said x-ray powder diffraction pattern further comprises one or more peaks selected from the group consisting of peaks at the following 2θ-angles±0.2° 2θ: 17.1, 18.0, 18.4, 18.8 and 19.4°.

Item 85. The solid form according to any one of items 81-82 and 84, wherein said potassium salt has a crystal form characterized by an XRPD obtained using CuKα1 radiation (λ=1.5406 Å) comprising peaks at the following 2θ-angles±0.2° 2θ: 3.0, 9.0, 12.6, 13.6, 15.0, 17.1, 18.0, 18.4, 18.8 and 19.4°.

Item 86. The solid form according to any one of items 81-85, wherein said potassium salt has a crystal form characterized by an XRPD obtained using CuKα1 radiation (λ=1.5406 Å) comprising peaks at the following 2θ-angles±0.1° 2θ: 3.0, 9.0, 12.6, 13.6, 15.0, 17.1, 18.0, 18.4, 18.8 and 19.4°.

Item 87. The solid form according to any one of items 81-82 and 84-85, wherein said potassium salt has a crystal form characterized by an XRPD obtained using CuKα1 radiation (λ=1.5406 Å) comprising peaks at the following 2θ-angles±0.2° 2θ: 3.0, 9.0, 12.6, 13.6, 15.0, 18.0, 19.4, 21.8, 24.7, 27.1, 29.8, 33.3, 35.6, 38.6 and 39.6°.

Item 88. The solid form according to any one of items 81-87, wherein said potassium salt has a crystal form characterized by an XRPD obtained using CuKα1 radiation (λ=1.5406 Å) comprising peaks at the following 2θ-angles±0.1° 2θ: 3.0, 9.0, 12.6, 13.6, 15.0, 18.0, 19.4, 21.8, 24.7, 27.1, 29.8, 33.3, 35.6, 38.6 and 39.6°.

Item 89. The solid form according to any one of items 81-88, wherein said potassium salt has a crystal form characterized by an XRPD obtained using CuKα1 radiation (λ=1.5406 Å) essentially as depicted in FIG. 15a.

Item 90. The solid form according to any one of items 81-89, exhibiting a weight loss of less than about 1% w/w compared to the initial weight when heated from about 20° C. to about 150° C. (heating rate 10° C./min), such as measured using thermogravimetric analysis.

Item 91. The solid form according to any one of items 81-90, wherein said solid form is a crystal form characterized by thermogravimetric analysis (using a heating rate 10° C./min) essentially as depicted in FIG. 15b.

Item 92. The solid form according to any one of items 1, 2, and 79-80, wherein said salt is a sodium salt of the compound of formula (Id).

Item 93. The solid form according to item 92, wherein said sodium salt is the sodium salt form 1 of the compound of formula (Id).

Item 94. The solid form according to item 93, wherein said sodium salt has a crystal form characterized by an XRPD obtained using CuKα1 radiation (λ=1.5406 Å) comprising peaks at the following 2θ-angles±0.2° 2θ: 5.9, 8.9, 11.9, 12.8, 13.8°.

Item 95. The solid form according to any one of items 93-94, wherein said sodium salt has a crystal form characterized by an XRPD obtained using CuKα1 radiation (λ=1.5406 Å) comprising peaks at the following 2θ-angles±0.1° 2θ: 5.9, 8.9, 11.9, 12.8, 13.8°.

Item 96. The solid form according to any one of items 94-95, wherein said x-ray powder diffraction pattern further comprises one or more peaks selected from the group consisting of peaks at the following 2θ-angles±0.2° 2θ: 14.9, 17.7, 18.6, 19.0 and 19.5°.

Item 97. The solid form according to any one of items 93-94 and 95-96, wherein said sodium salt has a crystal form characterized by an XRPD obtained using CuKα1 radiation (λ=1.5406 Å) comprising peaks at the following 2θ-angles±0.2° 2θ: 5.9, 8.9, 11.9, 12.8, 13.8, 14.9, 17.7, 18.6, 19.0 and 19.5°.

Item 98. The solid form according to any one of items 93-97, wherein said sodium salt has a crystal form characterized by an XRPD obtained using CuKα1 radiation (λ=1.5406 Å) comprising peaks at the following 2θ-angles±0.1° 2θ: 5.9, 8.9, 11.9, 12.8, 13.8, 14.9, 17.7, 18.6, 19.0 and 19.5°.

Item 99. The solid form according to any one of items 93-94 and 96-97, wherein said sodium salt has a crystal form characterized by an XRPD obtained using CuKα1 radiation (λ=1.5406 Å) comprising peaks at the following 2θ-angles±0.2° 2θ: 8.9, 12.8, 13.8, 14.9, 17.7, 18.6, 19.0, 19.5, 21.5, 21.8, 22.2, 22.6, 22.9, 23.4 and 25.1°.

Item 100. The solid form according to any one of items 93-99, wherein said sodium salt has a crystal form characterized by an XRPD obtained using CuKα1 radiation (λ=1.5406 Å) comprising peaks at the following 2θ-angles±0.1° 2θ: 8.9, 12.8, 13.8, 14.9, 17.7, 18.6, 19.0, 19.5, 21.5, 21.8, 22.2, 22.6, 22.9, 23.4 and 25.1°.

Item 101. The solid form according to any one of items 93-100, wherein said sodium salt has a crystal form characterized by an XRPD obtained using CuKα1 radiation (λ=1.5406 Å) essentially as depicted in FIG. 16a.

Item 102. The solid form according to any one of items 93-101, exhibiting a weight loss of about 2% w/w compared to the initial weight when heated from about 20° C. to about 175° C. (heating rate 10° C./min), such as when measured using thermogravimetric analysis.

Item 103. The solid form according to any one of items 93-102, wherein said solid form is a crystal form characterized by thermogravimetric analysis (using a heating rate 10° C./min) essentially as depicted in FIG. 16b.

Item 104. The solid form according to item 92, wherein said sodium salt is the sodium salt form 2 of the compound of formula (Id).

Item 105. The solid form according to item 104, wherein said sodium salt has a crystal form characterized by an XRPD obtained using CuKα1 radiation (λ=1.5406 Å) comprising peaks at the following 2θ-angles±0.2° 2θ: 5.6, 8.5, 12.6, 13.6, 14.1°.

Item 106. The solid form according to any one of items 104-105, wherein said sodium salt has a crystal form characterized by an XRPD obtained using CuKα1 radiation (λ=1.5406 Å) comprising peaks at the following 2θ-angles±0.1° 2θ: 5.6, 8.5, 12.6, 13.6, 14.1°.

Item 107. The solid form according to any one of items 105-106, wherein said x-ray powder diffraction pattern further comprises one or more peaks selected from the group consisting of peaks at the following 2θ-angles±0.2° 2θ: 15.0, 16.7, 17.0, 18.8 and 19.8°.

Item 108. The solid form according to any one of items 104-105 and 107, wherein said sodium salt has a crystal form characterized by an XRPD obtained using CuKα1 radiation (λ=1.5406 Å) comprising peaks at the following 2θ-angles±0.2° 2θ: 5.6, 8.5, 12.6, 13.6, 14.1, 15.0, 16.7, 17.0, 18.8 and 19.8°.

Item 109. The solid form according to any one of items 104-108, wherein said sodium salt has a crystal form characterized by an XRPD obtained using CuKα1 radiation (λ=1.5406 Å) comprising peaks at the following 2θ-angles±0.1° 2θ: 5.6, 8.5, 12.6, 13.6, 14.1, 15.0, 16.7, 17.0, 18.8 and 19.8°.

Item 110. The solid form according to any one of items 104-105 and 107-108, wherein said sodium salt has a crystal form characterized by an XRPD obtained using CuKα1 radiation (λ=1.5406 Å) comprising peaks at the following 2θ-angles±0.2° 2θ: 5.6, 8.5, 12.6, 13.6, 14.1, 15.0, 17.0, 18.8, 19.8, 21.0, 23.4, 28.5, 34.3, 37.3 and 38.5°.

Item 111. The solid form according to any one of items 104-110, wherein said sodium salt has a crystal form characterized by an XRPD obtained using CuKα1 radiation (λ=1.5406 Å) comprising peaks at the following 2θ-angles±0.1° 2θ: 5.6, 8.5, 12.6, 13.6, 14.1, 15.0, 17.0, 18.8, 19.8, 21.0, 23.4, 28.5, 34.3, 37.3 and 38.5°.

Item 112. The solid form according to any one of items 104-111, wherein said sodium salt has a crystal form characterized by an XRPD obtained using CuKα1 radiation (λ=1.5406 Å) essentially as depicted in FIG. 17a.

Item 113. The solid form according to any one of items 104-112, exhibiting a weight loss of about 5% w/w compared to the initial weight when heated from about 20° C. to about 175° C. (heating rate 10° C./min), such as when measured using thermogravimetric analysis.

Item 114. The solid form according to any one of items 104-113, wherein said solid form is a crystal form characterized by thermogravimetric analysis (using a heating rate 10° C./min) essentially as depicted in FIG. 17b.

Item 115. The solid form according to any one of items 1-2, wherein said solid form is a halogenide salt of the compound of formula (Id).

Item 116. The solid form according to items 1 and 115, wherein said solid form is a halogenide salt of the compound of formula (Id) selected from the group consisting of a hydrochloride salt and a hydrobromide salt of the compound of formula (Id).

Item 117. The solid form according to any of items 1 and 115-116, wherein said salt is a hydrochloride salt of the compound of formula (Id).

Item 118. The solid form according to any one of items 115-117, wherein said hydrochloride salt has a crystal form characterized by an XRPD obtained using CuKα1 radiation (λ=1.5406 Å) comprising peaks at the following 2θ-angles±0.2° 2θ: 5.7, 7.3, 10.6, 13.3, 15.3°.

Item 119. The solid form according to any one of items 115-118, wherein said hydrochloride salt has a crystal form characterized by an XRPD obtained using CuKα1 radiation (λ=1.5406 Å) comprising peaks at the following 2θ-angles±0.1° 2θ: 5.7, 7.3, 10.6, 13.3, 15.3°.

Item 120. The solid form according to any one of items 118-119, wherein said x-ray powder diffraction pattern further comprises one or more peaks selected from the group consisting of peaks at the following 2θ-angles±0.2° 2θ: 15.4, 16.2, 20.1, 22.5 and 23.0°.

Item 121. The solid form according to any one of items 115-118 and 120, wherein said hydrochloride salt has a crystal form characterized by an XRPD obtained using CuKα1 radiation (λ=1.5406 Å) comprising peaks at the following 2θ-angles±0.2° 2θ: 5.7, 7.3, 10.6, 13.3, 15.3, 15.4, 16.2, 20.1, 22.5 and 23.0°.

Item 122. The solid form according to any one of items 115-121, wherein said hydrochloride salt has a crystal form characterized by an XRPD obtained using CuKα1 radiation (λ=1.5406 Å) comprising peaks at the following 2θ-angles±0.1° 2θ: 5.7, 7.3, 10.6, 13.3, 15.3, 15.4, 16.2, 20.1, 22.5 and 23.0°.

Item 123. The solid form according to any one of items 115-118 and 121, wherein said hydrochloride salt has a crystal form characterized by an XRPD obtained using CuKα1 radiation (λ=1.5406 Å) comprising peaks at the following 2θ-angles±0.2° 2θ: 5.1, 5.7, 7.3, 10.6, 13.3, 15.3, 15.4, 16.2, 16.7, 18.1, 20.1, 22.5, 23.0, 23.6 and 23.8°.

Item 124. The solid form according to any one of items 115-123, wherein said hydrochloride salt has a crystal form characterized by an XRPD obtained using CuKα1 radiation (λ=1.5406 Å) comprising peaks at the following 2θ-angles±0.1° 2θ: 5.1, 5.7, 7.3, 10.6, 13.3, 15.3, 15.4, 16.2, 16.7, 18.1, 20.1, 22.5, 23.0, 23.6 and 23.8°.

Item 25, The solid form according to any one of items 115-124, wherein said hydrochloride salt has a crystal form characterized by an XRPD obtained using CuKα1 radiation (λ=1.5406 Å) essentially as depicted in FIG. 18.

Item 126. The solid form according to any one of items 1 and 115-116, wherein said salt is a hydrobromide salt of the compound of formula (Id).

Item 127. The solid form according to item 126, wherein said hydrobromide salt has a crystal form characterized by an XRPD obtained using CuKα1 radiation (λ=1.5406 Å) comprising peaks at the following 2θ-angles±0.2° 2θ: 12.5, 13.9, 14.5, 15.6, 18.6°.

Item 128. The solid form according to any one of items 126-127, wherein said hydrobromide salt has a crystal form characterized by an XRPD obtained using CuKα1 radiation (λ=1.5406 Å) comprising peaks at the following 2θ-angles±0.1° 2θ: 12.5, 13.9, 14.5, 15.6, 18.6°.

Item 129. The solid form according to any one of items 127-128, wherein said x-ray powder diffraction pattern further comprises one or more peaks selected from the group consisting of peaks at the following 2θ-angles±0.2° 2θ: 18.9, 19.8, 21.3, 22.0 and 22.4°.

Item 130. The solid form according to any one of items 126-127 and 129, wherein said hydrobromide salt has a crystal form characterized by an XRPD obtained using CuKα1 radiation (λ=1.5406 Å) comprising peaks at the following 2θ-angles±0.2° 2θ: 12.5, 13.9, 14.5, 15.6, 18.6, 18.9, 19.8, 21.3, 22.0 and 22.4°.

Item 131. The solid form according to any one of items 126-130, wherein said hydrobromide salt has a crystal form characterized by an XRPD obtained using CuKα1 radiation (λ=1.5406 Å) comprising peaks at the following 2θ-angles±0.1° 2θ: 12.5, 13.9, 14.5, 15.6, 18.6, 18.9, 19.8, 21.3, 22.0 and 22.4°.

Item 132. The solid form according to any one of items 126-127 and 129-131, wherein said hydrobromide salt has a crystal form characterized by an XRPD obtained using CuKα1 radiation (λ=1.5406 Å) comprising peaks at the following 2θ-angles±0.2° 2θ: 12.5, 13.9, 14.5, 15.6, 18.6, 18.9, 19.8, 21.3, 22.0, 22.4, 23.3, 24.4, 25.5, 28.2 and 28.9°, Item 133, The solid form according to any one of items 126-132, wherein said hydrobromide salt has a crystal form characterized by an XRPD obtained using CuKα1 radiation (λ=1.5406 Å) comprising peaks at the following 2θ-angles±0.1° 2θ: 12.5, 13.9, 14.5, 15.6, 18.6, 18.9, 19.8, 21.3, 22.0, 22.4, 23.3, 24.4, 25.5, 28.2 and 28.9°.

Item 134. The solid form according to any one of items 126-133, wherein said hydrobromide salt has a crystal form characterized by an XRPD obtained using CuKα1 radiation (λ=1.5406 Å) essentially as depicted in FIG. 19.

Item 135. The solid form of the compound of formula (Id) selected from the group consisting of the DH1 as defined in items 7-19, the HH as defined in items 32-42, and the potassium salt as defined in items 80-91.

Item 136. The solid form of the compound of formula (Id) selected from the group consisting of the DH1 as defined in items 7-19 and the potassium salt as defined in items 80-91.

Item 137. A solid form of the zwitterion of compound (Id), said solid form exhibiting a weight loss of about 7.6% w/w compared to the initial weight when heated from about 30° C. to about 150° C. (heating rate 10° C./min), such as measured using thermogravimetric analysis.

Item 138. A solid form of the zwitterion of compound (Id), said solid form wherein said solid form is a crystal form characterized by thermogravimetric analysis (using a heating rate 10° C./min) essentially as depicted in FIG. 8b.

Item 139. A solid form of the zwitterion of compound (Id), said solid form is exhibiting a weight loss of less than 1% w/w compared to the initial weight when heated from about 30° C. to about 150° C. (heating rate 10° C./min), such as measured using thermogravimetric analysis.

Item 140. A solid form of the zwitterion of compound (Id), wherein said solid form is characterized by thermogravimetric analysis (using a heating rate 10° C./min) essentially as depicted in FIG. 9b.

Item 141. A solid form of the zwitterion of compound (Id), wherein said solid form is exhibiting a weight loss of about 21% w/w compared to the initial weight when heated from about 20° C. to about 150° C. (heating rate 10° C./min), such as measured using thermogravimetric analysis.

Item 142. A solid form of the zwitterion of compound (Id), wherein said solid form is characterized by thermogravimetric analysis (using a heating rate 10° C./min) essentially as depicted in FIG. 10b.

Item 143. A solid form of the zwitterion of compound (Id), wherein said solid form is exhibiting a weight loss of about 4% w/w compared to the initial weight when heated from about 20° C. to about 150° C. (heating rate 10° C./min), such as measured using thermogravimetric analysis.

Item 144. A solid form of the zwitterion of compound (Id), wherein said solid form is characterized by thermogravimetric analysis (using a heating rate 10° C./min) essentially as depicted in FIG. 14b.

Item 145. A solid form of compound (Id), wherein said solid form is the potassium salt exhibiting a weight loss of less than about 1% w/w compared to the initial weight when heated from about 20° C. to about 150° C. (heating rate 10° C./min), such as measured using thermogravimetric analysis.

Item 146. A solid form of compound (Id), wherein said solid form is the potassium salt characterized by thermogravimetric analysis (using a heating rate 10° C./min) essentially as depicted in FIG. 15b.

Item 47, A solid form of compound (Id), wherein said solid form is the sodium salt form exhibiting a weight loss of about 2% w/w compared to the initial weight when heated from about 20° C. to about 175° C. (heating rate 10° C./min), such as when measured using thermogravimetric analysis.

Item 148. A solid form of the zwitterion of compound (Id), wherein said solid form is the sodium salt form characterized by thermogravimetric analysis (using a heating rate 10° C./min) essentially as depicted in FIG. 16b.

Item 149. A solid form of compound (Id), wherein said solid form is the sodium salt form exhibiting a weight loss of about 5% w/w compared to the initial weight when heated from about 20° C. to about 175° C. (heating rate 10° C./min), such as when measured using thermogravimetric analysis.

Item 150. A solid form of compound (Id), wherein said solid form is the sodium salt characterized by thermogravimetric analysis (using a heating rate 10° C./min) essentially as depicted in FIG. 17b.

Item 151. A solid form of the compound of formula (Id) according to any one of items 1-150, for use in therapy.

Item 152. The DH1 form according to any one of items 7-19 for use in therapy. Item 153. The potassium salt form according to any one of items 80-91 for use in therapy.

Item 154. The solid form of the compound of formula (Id) according to any of items 1-150, for use as a medicament.

Item 155. The solid DH1 form according to any one of items 7-19 for use as a medicament.

Item 156. The solid potassium salt form according to any one of items 80-91 for use as a medicament.

Item 157. The solid form of the compound of formula (Id) according to any one of items 151-156, wherein said medicament is an oral medicament such as a tablet or a capsule for oral administration.

Item 158. A pharmaceutical composition comprising a therapeutically effective amount of the solid form of the compound of formula (Id) according to any of items 1-150, and one or more pharmaceutically acceptable excipients.

Item 159. The pharmaceutical composition according to item 158, wherein said solid form is the dihydrate of the zwitterion of the compound of formula (Id) DH1 according to any one of items 7-19.

Item 160. The pharmaceutical composition according to item 158, wherein said solid form is the potassium salt of the compound of formula (Id) according to any one of items 80-91.

Item 161. The pharmaceutical composition according to any one of items 158-160, wherein said pharmaceutical composition is for oral administration.

Item 162. The pharmaceutical composition according to any one of items 158-161, wherein said pharmaceutical composition is an oral pharmaceutical composition.

Item 163. The pharmaceutical composition according to any one of items 158-162, wherein said pharmaceutical composition is a solid oral dosage form.

Item 164. The pharmaceutical composition according to any one of items 158-163, wherein said pharmaceutical composition is a tablet or a capsule for oral administration.

Item 165. The pharmaceutical composition according to any one of items 158-164, wherein said pharmaceutical composition further comprises another agent which is useful in the treatment of a neurodegenerative disease or disorder such as Parkinson's disease.

Item 166. The pharmaceutical composition according to any one of items 158-165, wherein said pharmaceutical composition further comprises a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or an antibody targeting alpha-synuclein, Tau or A-beta protein.

Item 167. A solid form of the compound of formula (Id) according to any of items 1-150, for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

Item 168. The solid form for use according to item 167, wherein said solid form is the dihydrate of the zwitterion of the compound of formula (Id) DH1 according to any one of items 7-19.

Item 169. The solid form for use according to item 167, wherein said solid form is the potassium salt form of the compound of formula (Id) as defined by any one of items 80-91.

Item 170. The solid form of the compound of formula (Id) for use according to any of items 167-169, wherein said neurodegenerative disease or disorder is Parkinson's Disease.

Item 171. The solid form for use according to item 170, wherein said solid form is the dihydrate of the zwitterion of the compound of formula (Id) DH1 according to any one of items 7-19, and wherein said neurodegenerative disease or disorder is Parkinson's Disease.

Item 172. The solid form for use according to item 170, wherein said solid form is the potassium salt form of the compound of formula (Id) as defined by any one of items 80-91, and wherein said neurodegenerative disease or disorder is Parkinson's Disease, Item 173. The solid form for use according to any one of items 167-172, wherein said solid form is to be used in combination with another agent which is useful in the treatment of a neurodegenerative disease or disorder such as Parkinson's disease.

Item 174. The solid form for use according to any of items 167-173, wherein said solid form is to be used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

Item 175. The solid form for use according to any one of items 167-174; wherein said treatment is performed by oral administration of said compound.

Item 176. The solid form for use according to any one of items 167-175; wherein said compound is comprised in an oral pharmaceutical composition such as a tablet or a capsule for oral administration.

Item 177. A method for the treatment of a neurodegenerative disease or disorder such as Parkinson's Disease; Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of solid form of the compound of formula (Id) according to any of items 1-150, to a patient in need thereof.

Item 178. The method according to item 177; which method comprises the administration of a therapeutically effective amount of the dihydrate of the zwitterion of the compound of formula (Id) according to any one of items 7-19, to a patient in need thereof.

Item 179. The method according to item 177, which method comprises the administration of a therapeutically effective amount of solid form of the potassium salt form of the compound of formula (Id) as defined by any one of items 80-91; to a patient in need thereof.

Item 80, The method according to any one of items 177-179, wherein said neurodegenerative disease or disorder is Parkinson's Disease.

Item 181. The method according to any one of items 177 and 180; which method comprises the administration of a therapeutically effective amount of the dihydrate of the zwitterion of the compound of formula (Id) according to any one of items 7-19, to a patient in need thereof, and wherein said neurodegenerative disease or disorder is Parkinson's Disease, Item 182. The method according to item 177, 179 and 180, which method comprises the administration of a therapeutically effective amount of solid form of the potassium salt form of the compound of formula (Id) as defined by any one of items 80-91, to a patient in need thereof, and wherein said neurodegenerative disease or disorder is Parkinson's Disease.

Item 183. The method according to any one of items 177-182, wherein said solid form of compound (Id) is used in combination with another agent which is useful in the treatment of a neurodegenerative disease or disorder such as Parkinson's disease.

Item 184. The method according to any one of items 177-183, wherein said solid form of compound (Id), is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

Item 185. The method according to any one of items 177-184, wherein said administration is performed by the oral route.

Item 186. The method according to any one of items 177-185, wherein said solid form is comprised in an oral pharmaceutical composition such as a tablet or a capsule for oral administration.

Item 187. Use of solid form of the compound of formula (Id) according to any one of items 1-150, in the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

Item 188. The use according to item 187, for wherein said solid form is the zwitterion of the compound of formula (Id) DH1 according to any one of items 7-19.

Item 189. The use according to item 187, for wherein said solid form is the potassium salt form of the compound of formula (Id) as defined by any one of items 80-91, Item 190. The use according to any one of items 172-174, wherein said neurodegenerative disease or disorder is Parkinson's Disease.

Item 191. The use according to any one of items 187-190, wherein said medicament is used in combination with another agent which is useful in the treatment of a neurodegenerative disease or disorder such as Parkinson's disease.

Item 192. The use according to any one of items 187-191, wherein said medicament is used in combination with a compound selected from the group consisting of L-DOPA, droxidopa, foliglurax a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein, Item 193. The use according to any one of items 187-192, wherein said medicament is an oral medicament such as a tablet or a capsule for oral administration.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only and should not be construed as limiting the invention in any way.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (including "for instance", "for example", "e.g.", and "as such") in the present specification is intended merely to better illuminate the invention and does not pose a limitation on the scope of invention unless otherwise indicated.

It should be understood that the various aspects, embodiments, items, implementations and features of the invention mentioned herein may be claimed separately, or in any combination.

The present invention includes all modifications and equivalents of the subject-matter recited in the claims appended hereto, as permitted by applicable law.

EXPERIMENTAL SECTION

Example 1: Preparation of Compound (Id)

The compound of formula (Id) may be prepared by method described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XII" (published with Wiley-Interscience). Preferred methods include, but are not limited to, those described below.

The schemes are representative of methods useful in synthesizing the compounds of the present invention. They are not intended to constrain the scope of the invention in any way.

Compound (I) which can for example be prepared as disclosed in WO 2009/026934 was used as an intermediate in the synthesis of compounds of the invention.

WO2019101917 further discloses methods for preparing compound (Id).

LC-MS Methods

Analytical LC-MS data were obtained using the methods identified below.

Method 550: LC-MS were run on Waters Aquity UPLC-MS consisting of Waters Aquity including column manager, binary solvent manager, sample organizer; PDA detector (operating at 254 nM), ELS detector, and TO-MS equipped with APPI-source operating in positive ion mode.

LC-conditions: The column was Acquity UPLC BEH C18 1.7 µm; 2.1×50 mm operating at 60° C. with 1.2 ml/min of a binary gradient consisting of water+0.05% trifluoroacetic acid (A) and acetonitrile/water (95:5)+0.05% trifluoroacetic acid.

Gradient (linear):

| 0.00 min | 10% B |
| 1.00 min | 100% B |
| 1.01 min | 10% B |
| 1.15 min | 10% B |

Total run time: 1.15 minutes.

Method 551: LC-MS were run on Waters Aquity UPLC-MS consisting of Waters Aquity including column manager, binary solvent manager, sample organizer, FDA detector (operating at 254 nM), ELS detector, and TO-MS equipped with APPI-source operating in positive ion mode.

LC-conditions: The column was Acquity UPLC HSS T3 1.8 µm; 2.1×50 mm operating at 60° C. with 1.2 ml/min of a binary gradient consisting of water+0.05% trifluoroacetic acid (A) and acetonitrile/water (95:5)+0.05% trifluoroacetic acid.

Gradient (linear):

| 0.00 min | 2% B |
| 1.00 min | 100% B |
| 1.15 min | 2% B |

Total run time: 1.15 minutes.

Method 555: LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 µm; 2.1×150 mm operating at 60° C. with 0.6 ml/min of a binary gradient consisting of water+0.05% trifluoroacetic acid (A) and acetonitrile/water (95:5)+0.05% trifluoroacetic acid.

Gradient (linear):

| 0.00 min | 10% B |
| 3.00 min | 100% B |
| 3.60 min | 10% B |

Total run time: 3.6 minutes.

Preparative LCMS was performed using the method identified below.

Waters AutoPurification system using combined mass/UV detection.

Column: Sunfire 30×100 mm, 5 um particles. Operating at 40° C. with 90 ml/min of a binary gradient consisting of water+0.05% trifluoroacetic acid (A) and acetonitrile/water (3:5)+0.05% trifluoroacetic acid.

Gradient (linear):

| 0.00 min | 98% A |
| 5.00 min | 50% A |
| 5.50 min | 98% A |
| 6.00 min | 98% A |

HighRes MS was run on a Bruker Compact qTOF equipped with electrospray operating in positive or negative mode. Direct infusion was used and calibration was done with sodium formate.

Compound (Id) was prepared together with compound (Id') depicted below and the two compounds were isolated from each other in the last step.

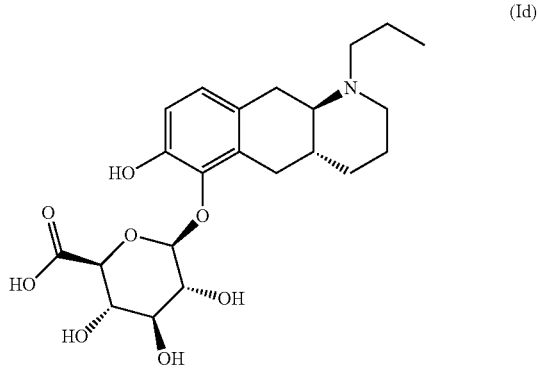

(Id)

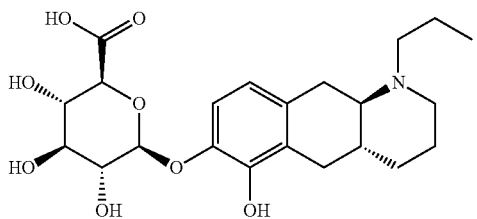

Example 2: Preparation of Intermediates for Preparation of Compound (Id) and (Id')

Intermediates:

(4aR,10aR)-1-propyl-7-((triisopropylsilyl)oxy)-1,2,3,4,4a,5,10,10a-octahydrobenzo[g]quinolin-6-al, and (4aR,10aR)-1-propyl-6-((triisopropylsilyl)oxy)-1,2,3,4,4a,5,10,10a-octahydrobenzo[g]quinolin-7-ol

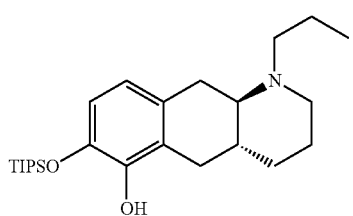

(4aR,10aR)-1-propyl-1,2,3,4,4a,5,10,10a-octahydrobenzo[g]quinoline-6,7-diol, hydrochloride (2.21 g, 7.43 mmol) was suspended in dichloromethane (80 ml) under nitrogen atmosphere at room temperature, N,N-diisopropylethylamine (4.44 g, 6.0 ml, 34.4 mmol) was added followed by triisopropylsilyl chloride (2.73 g, 3.0 ml, 14.16 mmol) and the mixture was stirred at room temperature for 92 hours. 10 mL MeOH was added, and the crude mixture was evaporated, coevaporated twice with dichloromethane/heptane, re-dissolved in dichloromethane, and evaporated directly on filter aid and purified by column chromatography (eluent: n-heptane/ethyl acetate/triethylamine, 100:0:0-35:60:5) affording 3.14 g as a mixture of (4aR,10aR)-1-propyl-7-((triisopropylsilyl)oxy)-1,2,3,4,4a,5,10,10a-octahydrobenzo[g]quinolin-6-ol (3.14 g) and (4aR,10aR)-1-propyl-6-((triisopropylsilyl)oxy)-1,2,3,4,4a,5,10,10a-octahydrobenzo[g]quinolin-7-ol as an oil.

NMR (CDCl3) showed >30:1 mixture of silylated isomers.

Intermediates:

tert-butyl ((4aR,10aR)-1-propyl-7-((triisopropylsilyl)oxy)-1,2,3,4,4a,5,10,10a-octahydrobenzo[g]quinolin-6-yl) carbonate [A], and tert-butyl ((4aR,10aR)-1-propyl-6-((triisopropylsilyl)oxy)-1,2,3,4,4a,5,10,10a-octahydrobenzo[g]quinolin-7-yl) carbonate [B]

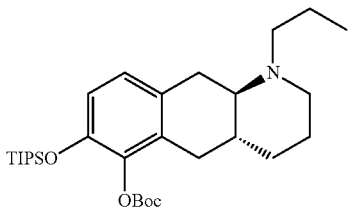

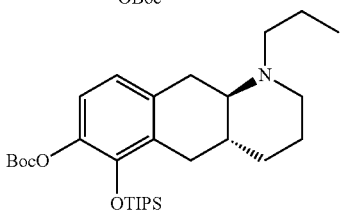

The mixture from the previous step (4aR,10aR)-1-propyl-7-((triisopropylsilyl)oxy)-1,2,3,4,4a,5,10,10a-octahydrobenzo[g]quinolin-6-ol and (4aR,10aR)-1-propyl-6-((triisopropylsilyl)oxy)-1,2,3,4,4a,5,10,10a-octahydrobenzo[g]quinolin-7-ol (2.94 g, 7.04 mmol) was dissolved in dichloromethane (30 ml) under a nitrogen atmosphere and cooled to 0° C. Pyridine (6.00 ml) followed by di-tert-butyl dicarbonate (6.30 g) were added and the reaction mixture was allowed to warm to room temperature over 3-4 hours and then stirred at room temperature overnight. 10 mL MeOH was added and the reaction mixture was evaporated, coevaporated with dichloromethane/n-heptane twice, dissolved in dichloromethane, and evaporated on filter aid.

Purification by column chromatography (eluent: n-heptane/ethyl acetate/triethylamine, 100:0:0-75:20:5) gave a mixture of tert-butyl ((4aR,10aR)-1-propyl-7-((triisopropylsilyl)oxy)-1,2,3,4,4a,5,10,10a-octahydrobenzo[g]quinolin-6-yl) carbonate [A] and tert-butyl ((4aR,10aR)-1-propyl-6-((triisopropylsilyl)oxy)-1,2,3,4,4a,5,10,10a-octahydrobenzo[g]quinolin-7-yl) carbonate [B] (3.6 g) as an oil.

NMR (CDCl3) after drying showed a mixture of regioisomers.

Intermediates:

(4aR,10aR)-6-((tert-butoxycarbonyl)oxy)-1-propyl-1,2,3,4,4a,5,10,10a-octahydrobenzo[g]quinolin-7-yl acetate, and (4aR,10aR)-7-((tert-butoxycarbonyl)oxy)-1-propyl-1,2,3,4,4a,5,10,10a-octahydrobenzo[g]quinolin-6-yl Acetate

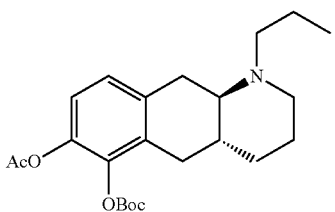

-continued

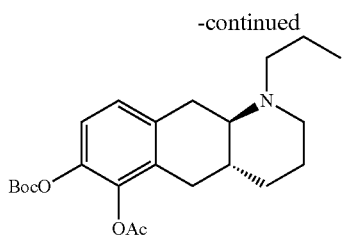

tert-Butyl-((4aR,10aR)-1-propyl-7-((triisopropylsilyl)oxy)-1,2,3,4,4a,5,10,10a-octahydrobenzo[g]quinolin-6-yl) carbonate (3.600 g, 6.95 mmol) (mixture of [A]:[B] from the previous step) was dissolved in THF (150 ml) under nitrogen atmosphere at 0° C., triethylamine trihydrofluoride (2.97 g, 3.00 ml, 18.42 mmol) was added and the mixture was stirred at 0° C. After 3 hours at 0° C., pyridine (10.0 ml, 124 mmol) and acetic anhydride (4.33 g, 4.00 ml, 42.4 mmol) were added directly to the reaction mixture at 0° C., and the reaction mixture was allowed to warm to room temperature. After 16 hours, 20 mL MeOH was added, and the reaction mixture was evaporated, redissolved in dichloromethane/n-heptane, and evaporated on filter aid followed by purification by dry column vacuum chromatography affording (4aR,10aR)-6-((tert-butoxycarbonyl)oxy)-1-propyl-1,2,3,4,4a,5,10,10a-octahydrobenzo[g]quinolin-7-yl acetate and (4aR,10aR)-7-((tert-butoxycarbonyl)oxy)-1-propyl-1,2,3,4,4a,5,10,10a-octahydrobenzo[g]quinolin-6-yl acetate as an oil/foam.

LCMS (method 550) rt=0.56 minutes, [M+H]$^+$=404 m/z.
Intermediates:

(2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate, and (2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl Triacetate (4aR,10aR)-6-((tert-butoxycarbonyl)oxy)-1-propyl-2,3,4,4a,5,10,10a-octahydrobenzo[g]quinolin-7-yl acetate (2.489 g, 6.17 mmol) (mixture of (4aR,10aR)-6-((tert-butoxycarbonyl)oxy)-1-propyl-1,2,3,4,4a,5,10,10a-octahydrobenzo[g]quinolin-7-yl acetate and (4aR,10aR)-7-((tert-butoxycarbonyl)oxy)-1-propyl-1,2,3,4,4a,5,10,10a-octahydrobenzo[g]quinolin-6-yl acetate assumed) was dissolved in dichloromethane (60 ml) under nitrogen atmosphere at room temperature, (2S,3R,4S,5S,6S)-6-(Methoxycarbonyl)tetrahydro-2H-pyran-2,3,4,5-tetrayl tetraacetate (7.529 g, 20.01 mmol) was added followed by the addition of boron trifluoride diethyl etherate (6.72 g, 6.0 ml, 47.3 mmol) and the mixture was stirred at room temperature for 5 days. The mixture was diluted with dichloromethane and MeOH and evaporated on filter aid. Purification by dry column vacuum chromatography to give a mixture of (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate and (2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyltriacetate (4.37 g) as a foam/solid.

LC-MS (method 555) rt=1.94 minutes, [M+H]$^+$=620 m/z.
(Id)

(2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic Acid, and (Id')

(2S,3S,4S,5R,6S)-3,4,5-trihydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic Acid, and

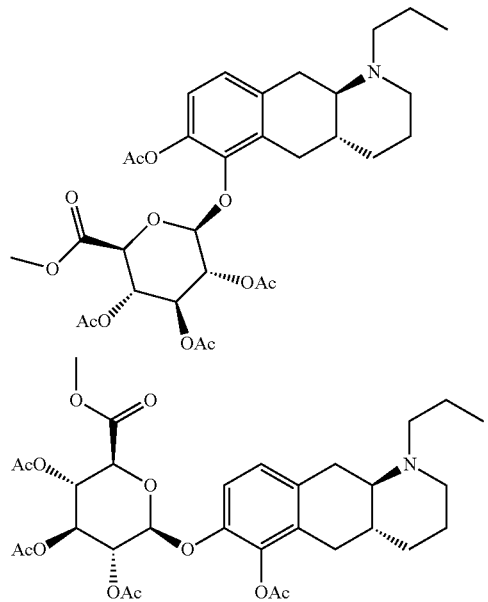

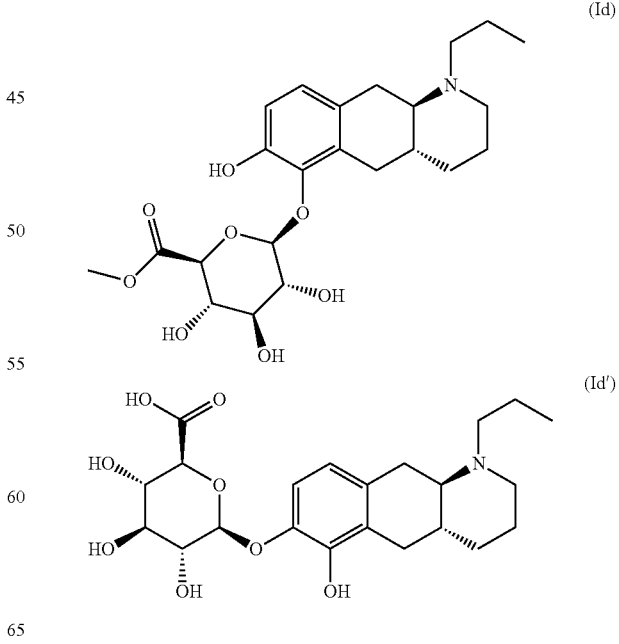

A mixture of (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate and (2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate (3.82 g, 6.17 mmol) was dissolved in MeOH (100 ml) and water (20 ml), cooled to 0° C., potassium cyanide (7.295 g, 112 mmol) was added and the suspension was allowed to slowly warm to room temperature for 17.5 hours. The crude mixture was evaporated on filter aid and dried. The crude mixture was purified by silica gel column chromatography (eluent: ethyl acetate/MeOH/water 100:0:0-0:50:50), affording a 5-6:1 ratio of (Id') and (Id). The mixture was separated by preparative LCMS.

Collected Peak 1 fractions containing (Id') were pooled, evaporated, and combined with another batch of 186 mg (Id')-TFA, which had been prepared in a similar manner, using MeOH, evaporated, and dried to give a solid. (Id') was re-suspended in 10 mL EtOH, and 100 mL MTBE was added, and the resulting suspension was stirred at room temperature for 8 hours, the suspension was filtered and the precipitate washed with 2×10 mL MTBE and dried in a vacuum oven overnight to afford (Id') 1.601 g, as a solid corresponding to (2S,3S,4S,5R,6S)-3,4,5-trihydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic acid.

Collected Peak 2 fractions containing (Id) were pooled, evaporated, transferred to smaller flask with MeOH, evaporated, redissolved in ca. 12 mL MeOH, and repurified by preparative LCMS, and evaporated to give a foam/solid. Appropriate fractions were pooled, evaporated, transferred with MeOH to a smaller flask, and evaporated and combined with another batch of 40.7 mg (Id), which had been prepared in a similar manner. The combined batch was dissolved in 2.5 mL EtOH, 25 mL MTBE was added, and the suspension was stirred at room temperature. After 8 hours, the suspension was filtered and the precipitate washed with 2×2.5 mL MTBE and dried in the vacuum oven overnight to give 362.2 mg of (Id) as a solid. (Id) was suspended in ca. 10 mL EtOH, 50 mL MTBE was added, and the suspension was stirred at room temperature and filtered after 19 hours and the precipitate was washed with 2×10 mL MTBE, and dried in the vacuum oven at 40° C. to give (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid (Id) 0.279 g as a solid.
(Id')
LCMS (method 551) rt=0.37 minutes, [M+H]$^+$=438.1 m/z.
$^1$H NMR (600 MHz, Methanol-d$_4$) δ 7.02 (d, J=8.4 Hz, 1H), 6.65 (d, J=8.4 Hz, 1H), 4.73 (d, J=7.7 Hz, 1H), 3.89 (d, J=9.7 Hz, 1H), 3.68-3.58 (m, 2H), 3.54 (dd, J=9.3, 7.7 Hz, 1H), 3.49 (t, J=9.1 Hz, 1H), 3.47-3.36 (m, 2H), 3.30 (dt, J=11.2, 5.6 Hz, 1H), 3.21-3.11 (m, 3H), 2.85 (dd, J=15.4, 11.3 Hz, 1H), 2.35 (dd, J=17.6, 11.5 Hz, 1H), 2.12-2.02 (m, 2H), 2.02-1.84 (m, 3H), 1.81-1.71 (m, 1H), 1.49 (qd, J=13.0, 3.7 Hz, 1H) 1.09 (t, J=7.3 Hz, 3H).
(Id)
LCMS (method 551) rt=0.39 minutes, [M+H]$^+$=438.1 m/z.
$^1$H NMR (600 MHz, Methanol-d$_4$) δ 6.87 (d, J=8.3 Hz, 1H), 6.74 (d, J=8.4 Hz, 1H), 4.62 (d, J=7.9 Hz, 1H), 3.75 (dd, J=17.7, 4.9 Hz, 1H), 3.66-3.62 (m, 2H), 3.61-3.51 (m, 2H), 3.50-3.35 (m, 3H), 3.31-3.22 (m, 1H), 3.14 (qd, J=12.7, 4.0 Hz, 2H), 2.83 (dd, J=15.2, 11.3 Hz, 1H), 2.37 (dd, J=17.7, 11.7 Hz, 1H), 2.12 (d, J=13.4 Hz, 1H), 2.08-2.00 (m, 1H), 1.98-1.83 (m, 3H), 1.81-1.71 (m, 1H), 1.44 (qd, J=13.2, 3.9 Hz, 1H), 1.09 (t, J=7.3 Hz, 3H).

Example 3: Preparation of Exemplified Solid Forms of the Invention

The present example describes preparation methods for the solid forms of the invention and a characterization of the solid forms with respect to X-Ray powder diffractograms (XRPD) and Thermo gravimetric analysis (TGA). The characterization was performed using the methods as described below.

XRPD:

X-Ray powder diffractograms were measured on a PANalytical X'Pert PRO X-Ray Diffractometer using CuK$_{\alpha 1}$ radiation (λ=1.5406 Å). The samples were measured in reflection mode in the 2θ-range 2-40° or 3-40 using an X'celerator detector.

Selected Peaks:

The peaks were found by peak-search on the diffractogram using the program "HighScore Plus" from panalytical. 10 peaks selected as characteristic for the compounds are listed in Table 2 below (a), as well as the 15 peaks with highest intensity for each compound (b). Diffraction data are indicated ±0.1°. It is well known that relative intensities between characterization of batches of the same solid form may vary considerable due to preferred orientation effects.

TABLE 2

| Overview of solid forms and XRPD peaks | | |
|---|---|---|
| Solid form | peaks | Peaks expressed in degree of diffraction angle 2θ |
| Dihydrate (DH1) | (a) | 10.4, 11.6, 12.3, 13.1, 13.6, 14.3, 15.6, 16.0, 16.8, 18.5° |
| | (b) | 12.3, 13.1, 13.6, 16.0, 16.8, 18.5, 18.9, 19.4, 20.5, 21.4, 23.5, 24.7, 25.4, 26.9, 28.7° |
| Anhydrate (AH1) | (a) | 8.5, 11.1, 12.4, 12.9, 15.6, 16.7, 18.9, 19.3, 20.0, 21.2° |
| | (b) | 8.5, 12.4, 12.9, 15.6, 16.7, 18.9, 19.3, 20.0, 21.2, 21.5, 22.2, 23.0, 24.2, 27.3, 28.3° |
| Heptahydrate (HH) | (a) | 7.0, 8.6, 10.2, 11.1, 11.9, 13.4, 14.0, 14.5, 17.0, 17.4° |
| | (b) | 7.0, 8.6, 10.2, 11.1, 11.9, 14.0, 17.0, 22.2, 25.9, 27.3, 28.3, 30.8, 34.0, 34.8, 35.2°. |
| Form A | (a) | 7.6, 9.5, 10.0, 11.2, 12.0, 14.3, 14.6, 15.3, 15.5, 19.3° |
| | (b) | 7.6, 9.5, 10.0, 11.2, 12.0, 14.3, 14.6, 15.3, 15.5, 18.7, 19.3, 23.9, 28.8, 33.7, 38.7° |
| Form B | (a) | 7.6, 9.0, 10.9, 12.3, 14.3, 15.0, 21.5, 22.1, 22.6, 23.7° |
| | (b) | Only ten peaks identified |
| Form C | (a) | 7.5, 8.1, 10.3, 12.6, 13.5, 13.8, 14.9, 17.5, 18.5, 20.6° |
| | (b) | 7.5, 8.1, 10.3, 12.6, 13.5, 13.8, 14.9, 17.5, 18.5, 20.6, 21.6, 22.9, 23.1, 24.0, 25.4° |
| Monohydrate (MH1) | (a) | 9.2, 10.2, 11.8, 12.6, 13.6, 15.7, 16.0, 16.5, 17.5, 18.1° |
| | (b) | 9.2, 10.2, 11.8, 12.6, 13.6, 16.0, 16.5, 17.5, 18.1, 18.7, 19.6, 22.9, 24.7, 25.4, 26.0° |
| Potassium salt (K$^+$ salt) | (a) | 3.0, 9.0, 12.6, 13.6, 15.0, 17.1, 18.0, 18.4, 18.8, 19.4° |
| | (b) | 3.0, 9.0, 12.6, 13.6, 15.0, 18.0, 19.4, 21.8, 24.7, 27.1, 29.8, 33.3, 35.6, 38.6, 39.6° |

TABLE 2-continued

Overview of solid forms and XRPD peaks

| Solid form | peaks | Peaks expressed in degree of diffraction angle 2θ |
|---|---|---|
| Na⁺ salt form 1 | (a) | 5.9, 8.9, 11.9, 12.8, 13.8, 14.9, 17.7, 18.6, 19.0 and 19.5° |
| | (b) | 8.9, 12.8, 13.8, 14.9, 17.7, 18.6, 19.0, 19.5, 21.5, 21.8, 22.2, 22.6, 22.9, 23.4, 25.1° |
| Na⁺ salt form 2 | (a) | 5.6, 8.5, 12.6, 13.6, 14.1, 15.0, 16.7, 17.0, 18.8 and 19.8° |
| | (b) | 5.6, 8.5, 12.6, 13.6, 14.1, 15.0, 17.0, 18.8, 19.8, 21.0, 23.4, 28.5, 34.3, 37.3, 38.5° |
| HCl salt | (a) | 5.7, 7.3, 10.6, 13.3, 15.3, 15.4, 16.2, 20.1, 22.5, 23.0°. |
| | (b) | 5.1, 5.7, 7.3, 10.6, 13.3, 15.3, 15.4, 16.2, 16.7, 18.1, 20.1, 22.5, 23.0, 23.6, 23.8°. |
| HBr salt | (a) | 12.5, 13.9, 14.5, 15.6, 18.6, 18.9, 19.8, 21.3, 22.0, 22.4° |
| | (b) | 12.5, 13.9, 14.5, 15.6, 18.6, 18.9, 19.8, 21.3, 22.0, 22.4, 23.3, 24.4, 25.5, 28.2, 28.9° |

TGA:

Thermo gravimetric analysis (TGA) was measured using a TA-instruments Discovery TGA. 1-10 mg sample is heated 10°/min in an open pan under nitrogen flow. Sample sizes of about 2-6.4 mg.

Preparation of Dihydrate (DH1) of Compound (Id):

Example A

To a 250 mL 1-necked round-bottomed flask were charged compound (Id) (4.0 g including some water of hydration), water (12 mL) and ethanol (12 mL). The white suspension was heated to 75° C., where a clear solution was obtained. The solution was cooled to 55° C. At 50-55° C. ethanol (56 mL) was added over 10 minutes. The suspension was stirred overnight at 50° C. The suspension was cooled over 6 hours to 23° C. and filtered. The filter cake was washed twice with ethanol (2×10 mL). The white filter cake was transferred to a drying tray and airdried in the fume hood for 1 day to constant weight. Yield 3.8 grams DH1.

Example B

To a 5 L 3-necked round-bottomed flask were charged compound (Id) (197 g including some water of hydration), water (0.60 L) and ethanol (0.60 L), The white suspension was heated to reflux, where a clear solution was obtained. The solution was kept at reflux for 30 minutes and then cooled over 35 minutes to 54° C. At 54° C. a slurry of the dihydrate (DH1) of compound (Id) (6.9 g) in ethanol (0.10 L) was added in one portion followed by additional ethanol (0.10 L). The temperature of the resulting suspension was increased from 52-54° C. in 5 minutes followed by addition of ethanol (1.60 L) over 17 minutes holding the temperature of the suspension at 53-55° C. during the addition. The suspension was stirred 1 hour at 53° C. and then cooled slowly overnight to 23° C. The suspension was filtered, and the resulting filter cake was washed twice with ethanol (2×0.40 L). The white filter cake was transferred to a drying tray and airdried in the fume hood for 2 days to constant weight. Yield 188 g DH1.

The prepared DH1 was characterized by XRPD (see Table 2 and FIG. 8) and TGA (see FIG. 8).

Preparation of Anhydrate (AH1) of Compound (Id):

Example A

In a 500 mL round bottom flask equipped with a stir bar 8.8 g compound (Id) (evaporated mother liquor from other batches) was suspended in 9:1 EtOH/H2O (90 mL) and warmed to 95° C. The suspension was stirred (320 rpm) for 1 h 20 minutes at 95° C. The heat bath was then switched off and the mixture was stirred (320 rpm) for 2 h until the bath had reached RT. The precipitate was collected by vacuum filtration and the flask/filter cake was washed with EtOH (2×50 mL). The resulting solid was dried on the filter pad (with vacuum running) for 1 hour, then scraped into a crystallization dish and air dried for 48 hours. Yield: 7.4 g AH1.

Example B

To a 250 mL 1-necked round-bottomed flask were charged with compound (Id) (3.0 g), water (9 mL) and ethanol (9 mL). The suspension was heated to 75° C., where a clear solution was obtained. The solution was cooled to 55° C. At 50-55° C. ethanol (162 mL) was added over 15 minutes. Precipitation was observed during the addition of ethanol. The suspension was stirred overnight at 50° C. The suspension was cooled over 6 hours to 23° C. and filtered. The filter cake was washed twice with ethanol (2×10 mL). The filter cake was transferred to a drying tray and airdried in the fume hood for 1 day to constant weight. Yield 2.7 g AH1.

The prepared AH1 was characterized by XRPD (see Table 2 and FIG. 9A) and TGA (see FIG. 9B).

Preparation of Heptahydrate (HH) of Compound (Id)

The heptahydrate (HH) of compound (Id) was prepared by precipitation from water. 45.5 mg DH1 of compound (Id) as prepared in example b above was added 0.5 mL of water and shaked for ~2 minutes. The wet crystals were removed from the solution and analysed by XRPD showing that HH was formed (see Table 2 and FIG. 10A). The HH was further analysed by TGA (see FIG. 10*b*).

Preparation of Form a of Compound (Id):

Form A is obtained by storage of the heptahydrate of compound (Id) (HH) at room temperature at ~5% RH.

The prepared form A of compound (Id) was characterized by XRPD (see Table 2 and FIG. 11).

Preparation of Form B of Compound (Id):

Form B was obtained by storage of the heptahydrate of compound (Id) (HH) at room temperature at ~10% RH.

The prepared form B of compound (Id) was characterized by XRPD (see Table 2 and FIG. 12).

Preparation of Form C of Compound (Id):

Form C was obtained by storage of the heptahydrate of compound (Id) (HH) at room temperature at ~15% RH.

The prepared form C of compound (Id) was characterized by XRPD (see Table 2 and FIG. 13).

Preparation of Monohydrate (MH1) of Compound (Id):

(MH1) was formed by heating of (DH1) to 105° C. and subsequent water sorption at ambient conditions to give a monohydrate. It is also obtained by drying (DH1) at room temperature to 0% RH, and subsequent water sorption at ambient conditions.

The prepared MH1 was characterized by XRPD (see Table 2 and FIG. 14*a*) and TGA (see FIG. 14*b*).

Preparation of the Potassium Salt of Compound (Id):

A 25 mL round bottomed flask with a magnetic stir bar was charged with compound (Id) heptahydrate (0.50 g).

Then, water (0.5 mL) and aqueous potassium hydroxide (0.11 g, 0.075 mL, 0.90 mmol, 46% (w/w)) was added, and the mixture became a slurry. The mixture was heated to 80° C., then cooled to 50-60° C. Additional water (0.2 mL) was added resulting in an almost clear solution, i-PrOH (1.5 mL) was added dropwise, first a clear solution was obtained, then a white solid precipitated out. The temperature was raised to 80° C. and a clear solution was obtained. i-PrOH (2.5 mL) was added dropwise, then the mixture was warmed to reflux and 1-2 mL was distilled off, and i-PrOH (1-2 mL) was added and the distillation/addition was repeated once. The mixture was cooled slowly to 5° C. and filtered affording 0.41 g potassium salt of compound (Id).

The prepared potassium salt was characterized by XRPD (see Table 2 and FIG. 15a) and TGA (see FIG. 15b).

Preparation of Sodium Salt Form 1 of Compound (Id):

A 25 mL round bottomed flask with a magnetic stir bar was charged with (Id) heptahydrate (0.5 g). Then, water (0.500 ml) and NaOH (0.083 ml, 10.8 molar) was added, and the mixture became a slurry). The mixture was heated to 50° C., then additional water (0.500 ml) was added resulting in a clear solution. The temperature was raised to 80° C. and i-PrOH (3.50 ml) was added dropwise and gel-like solid precipitated out. The mixture was stirred for 30 minutes and then allowed to cool slowly to room temperature and then to 5° C. Then, the precipitate was isolated by very slow filtration (filtration for a period of at least 6 hours) and the precipitate was washed with 2×0.5 mL iPrOH. The solid was dried in the vacuum oven at 40° C. overnight. This afforded a sodium salt of compound (Id) (0.35 g) as a solid.

The prepared sodium salt form 1 was characterized by XRPD (see Table 2 and FIG. 16a) and TGA (see FIG. 16b).

Preparation of Sodium Salt Form 2 of Compound (Id):

51.73 mg was added 70 µl water and the mixture was heated to 60° C. to dissolution where after 150 µl iPrOH was added. Then the mixture was heated to 60° C., 250 µl iPrOH was added and the mixture was heated to 60° C. After leaving at room temperature, a precipitation occurred. The liquid was sucked of and the solid part was placed at 90° C. which led to partial dissolution, so it was removed from the heat again and sodium salt form 2 was obtained.

The prepared sodium salt form 2 was characterized by XRPD (see Table 2 and FIG. 17a) and TGA (see FIG. 17b).

Preparation of Hydrochloride Salt of Compound (Id):

Ca. 500 mg of compound (Id) Heptahydrate was weighed and then slurried in 3.75 mL of IPA and 1.05 equivalents of HCl was added in 2.5 mL of IPA. The mixture of API/counterion/solvent was temperature cycled between ambient and 40° C. in 4-hour cycles. After ca. 1 day the preparation was observed to have dissolved at 40° C. and to contain a small amount of gum-like material at ambient. The experiment was allowed to evaporate at ambient temperature. The material appeared gum-like after incomplete evaporation and re-slurrying using IPA 500 µL IPA.

Scale-up was re-prepared using less IPA, ca. 500 mg of compound (Id) Heptahydrate was weighed and then slurried in 0.9 mL of IPA and 1.05 equivalents of HCl was added in 2.5 mL of IPA. The mixture of API/counterion/solvent was temperature cycled between ambient and 40° C. in 4-hour cycles. After ca. 1 day the preparation was allowed to evaporate at ambient, due to limited solid present. After incomplete evaporation the material was scraped with a spatula, isolated by centrifuge filtration and dried under vacuum at ambient temperature for ca. 20 hours.

The prepared hydrochloride salt was characterized by XRPD (see Table 2 and FIG. 18).

Preparation of Hydrobromide Salt of Compound (Id):

Ca. 500 mg of compound (Id) Heptahydrate was weighed and slurried in 3.75 mL of IPA and 1.05 equivalents of HBr was added in 2.5 mL of IPA. The mixture of API/counterion/solvent was temperature cycled between ambient and 40° C. in 4-hour cycles for ca. 3 days.

The prepared hydrobromide salt was characterized by XRPD (see Table 2 and FIG. 19).

Example 4: Stability Studies of Selected Solid Forms

Stability studies were performed on the heptahydrate (HH), the dihydrate (DH1) and the potassium salt of compound (Id) ($K^+$ salt). The substances were packed individually in sealed polyethylene bags, with a carton box as a secondary packaging material. During stability the different batches were tested for visual appearance, assay (anhydrous i.e. calculated as water free compound), impurities and water content. In addition, XRPD was been performed as described in Example 3 at selected time points.

In addition, stress stability studies were performed for the heptahydrate (HH), the dihydrate (DH1) and the potassium salt of compound (Id) ($K^+$ salt). For the stress stability studies, the substances were stored in open dishes in the dark at 40° C./75% RH, 60° C. and 60° C./80% RH.

The following methods were used for the characterization:

LC-UV Methods (Assay and Impurities)

LC-UV was run on Agilent HPLC consisting of Agilent 1200 HPLC or equivalent including autosampler and DAD detector (operating at 278 nm).

LC-conditions: The column was Synergi Polar-RP 4 µm; 4.6×150 mm operating at 40° C. with 1.0 ml/min of a binary gradient consisting of water/acetonitrile+2 ml TFA/ml (90:10) (A) and water/acetonitrile+2 ml TFA/ml (35:65) (B).

Gradient:

| | |
|---|---|
| 0.0 min | 0% B |
| 2.0 min | 10% B |
| 12.0 min | 100% B |
| 14.0 min | 100% B |
| 14.1 min | 0% B |
| 19.0 min | 0% B |
| Total run time: | 19 minutes |

The amount of impurities was determined as % area of the peak of impurity relative to the area of the main peak.

Karl Fischer Determination (Water Determination)

The water content was determined by coulometric Karl Fischer titration according to the European Pharmacopoeia, chapter 2.5.32 (Metrohm 874 Oven Sample Processor and Metrohm 851 KF Coulometer). The water content was evaporated by heating samples to 150° C. and the water vapor was transferred by nitrogen to the titration chamber where it was titrated to endpoint using Hydranal Coulomat AG Oven (article number 34739) titration reagent.

Results

Stability

Less than 0.1% degradation as determined by LC-UV were seen for both the heptahydrate (HH), the potassium salt ($K^+$ salt) and the dihydrate (DH1) of compound (Id). Changes in visual appearance, water content and physical form (XRPD) were seen for the heptahydrate (HH). After 3 months at 40° C./75% RH the heptahydrate changed appearance to a slightly grey colour and changed into the dihydrate. At 25° C./60% RH a slight change in colour is seen over time in addition to a clear change in physical form. Results are presented in the Table 3 below.

TABLE 3

Stability of HH of the zwitterion of compound (Id)

| Stability time point | HH | | | | | |
|---|---|---|---|---|---|---|
| | 25° C./60% RH | | | 40° C./75% RH | | |
| | Appearance | Water content, % | Physical form | Appearance | Water content, % | Physical form |
| Initial | White powder with lumps | 21.6 | HH | White powder with lumps | 21.6 | HH |
| 3 months | White powder with lumps | 22.3 | HH + some DH1 | Slightly greyish with lumps | 7.6 | DH1 |
| 6 months | White powder with lumps | 20.0 | NP | Slightly greyish with lumps | 7.6 | NP |
| 9 months | White powder with lumps | 21.6 | Form C | NP | NP | NP |
| 12 months | Off-white powder | 15.0 | DH1 + form C | NP | NP | NP |
| 18 months | Off-white powder | 20.9 | NP | NP | NP | NP |

NP: Not performed

For the potassium salt, the results showed that that the samples remained in the same physical form as determined by XRPD. However, some changes in water content were observed, and formation of brown lumps was also observed seen during stability testing. A summary of results for the potassium salt of compound (Id) is shown in Table 4 below.

TABLE 4

Stability of the potassium salt of compound (Id)

| Stability time point | $K^+$ salt | | | | | |
|---|---|---|---|---|---|---|
| | 25° C./60% RH | | | 40° C./75% RH | | |
| | Appearance | Water content, % | Physical form | Appearance | Water content, % | Physical form |
| Initial | Very slightly beige powder with lumps | 0.11 | Alfa form | Very slightly beige powder with lumps | 0.11 | Alfa form |
| 3 months | Very slightly beige powder with lumps and brown spots | 0.22 | NP | Slightly beige powder with lumps and brown spots | 0.38 | NP |
| 6 months | Very slightly beige powder with lumps and brown spots | 0.17 | Alfa form | Slightly beige powder with lumps and brown spots | 0.25 | Alfa form |
| 9 months | Very slightly beige powder with lumps and brown spots | <0.10 | Alfa form | NP | NP | NP |
| 13 months | Very slightly beige powder with white and brown lumps | <0.10 | Alfa form | NP | NP | NP |
| 18 months | Very slightly beige powder with white and brown lumps | 0.23 | Alfa form | NP | NP | NP |

NP: Not performed, Alpha form: The $K^+$ salt form shown in Table 2.

For the dihydrate, no changes in appearance, water content or physical form (XRPD) were seen for 6 months stability testing at 40° C./75% RH and at 25° C./60% RH. Even after 10 months at 25° C./60% RH, no changes were observed in the physical appearance and the water content. A summary of results for dihydrate of compound (Id) is shown in Table 5 below.

TABLE 5

Stability of the dihydrate of the zwitterion of compound (Id)

| Stability time point | DH1 | | | | | |
|---|---|---|---|---|---|---|
| | 25° C./60% RH | | | 40° C./75% RH | | |
| | Appearance | Water content, % | Physical form | Appearance | Water content, % | Physical form |
| Initial | White powder | 7.6 | DH1 | White powder | 7.6 | DH1 |
| 4 months | White powder | 7.6 | DH1 | White powder | 7.4 | DH1 |
| 6 months | White powder | 7.6 | DH1 | White powder | 7.5 | DH1 |
| 10 months | White powder | 7.4 | NP | NP | NP | NP |

NP: Not performed

The results of the stability studies indicated that the dihydrate of the zwitterion of the compound (Id) (DH1) had best stability with respect to physical appearance, water content at physical form as measured at 40° C./75% RH and at 25° C./60% RH for 6 months.

Stress Stability

The stress stability testing was performed as described above, and the amount of degradation products were determined based on the LC-UV method described above.

The total sum of impurities after 6 months storage is shown in the Table 6 below.

TABLE 6

Stress stability

| Total sum of impurities after 6 months storage | 40° C./75% RH | 60° C. | 60° C./80% RH |
|---|---|---|---|
| Heptahydrate* | <0.05% | 4.3% | <0.05% |
| Dihydrate | 0.05% | 1.0% | 0.05% |
| Potassium salt | 0.10% | 0.10% | 1.0% |

*The heptahydrate has turned into the dihydrate at 40° C./75% RH and 60° C./80% RH. At 60° C. the heptahydrate has turned into form A.

It can be seen from the results of the stress stability test in Table 6 that the tested solid forms were relatively stable with respect to chemical degradation, particularly the dihydrate and the potassium salt.

Example 5: Further Stability Studies of Selected Solid Forms

The following example describes further characterization of the heptahydrate (HH), the dihydrate (DH1) of compound (Id), and the potassium salt of compound (Id).

DVS

Dynamic vapor sorption (DVS) was further used to evaluate selected solid forms, Hygroscopicity and dehydration behavior can be investigated by DVS analysis. DVS experiments were performed using a DVS Advantage 01 instrument from Surface Measurement Systems. Samples of 4-10 mg of the solid forms were used for the analysis. The water absorption/desorption of the target solid was monitored while changing the relative humidity between about 0% to about 90% in steps of about 5-10% RH.

Figure 21:
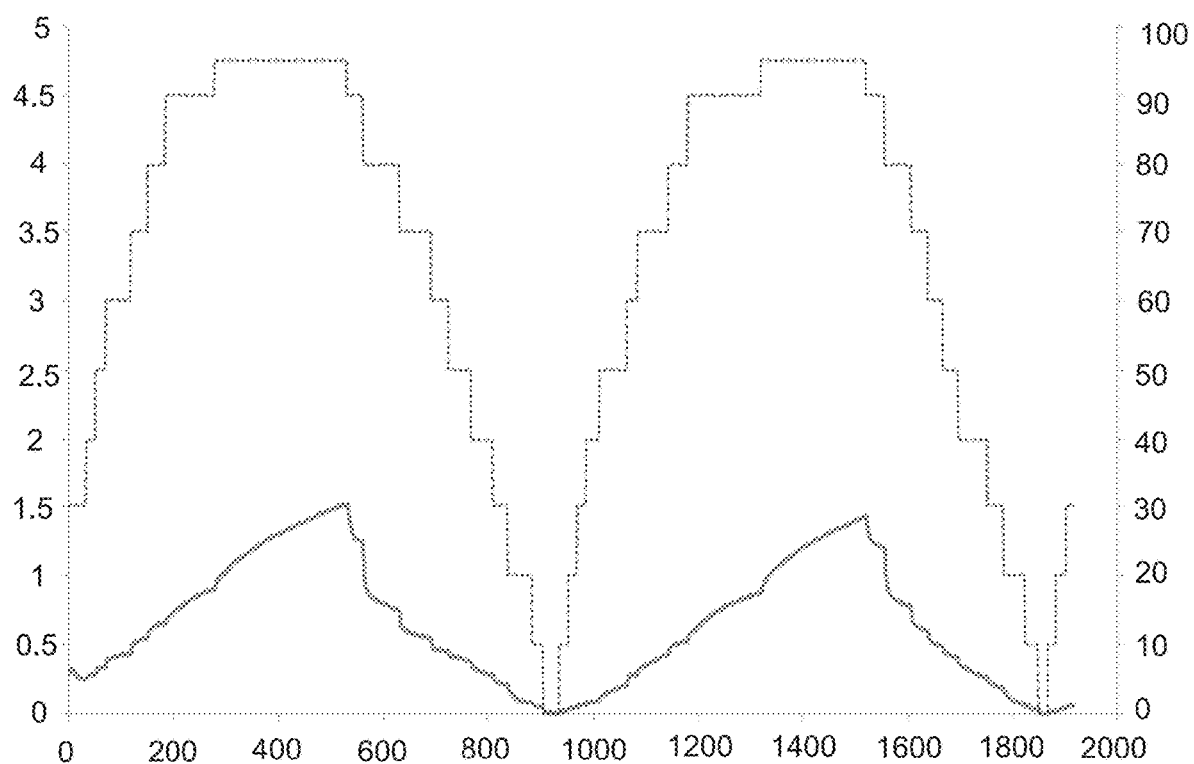

FIGS. 20 and 21 show the resulting curves for the DH1 and the K⁺ salt.

For the DH1, DVS analysis showed that the water content of DH1 is very stable in the humidity range 5-90% RH. Less than 0.1% of water is absorbed or desorbed.

For the potassium salt form of compound (Id) (K⁺ salt), the DVS showed a gradual weight change up to 0.6% at 80% RH, and further 1% at 90% RH. Only at 95% RH a steady increase in the weight was observed, however from the curve it can be seen that the water desorbed as soon as the humidity was lowered again. The curve of the second cycle showed the same behavior as the first cycle, thus no change in the crystal lattice occurred and the salt is stable towards change in humidity.

The DVS analysis of the heptahydrate (HH) indicated that the heptahydrate absorbs and desorbs water at humidity between 20% RH and 95% RH without changing the crystal form. At humidity below 20% the heptahydrate (HH) changes into other less hydrated forms and does not change back to the heptahydrate unless the material is exposed to high humidity.

Thus, from the DVS analysis, it can be concluded that the DH1 is non-hygroscopic in the humidity range between 5-80% RH.

Grinding and Pressure

HH of Compound (Id)

A sample of the heptahydrate was grinded by hand using mortar and pestle for 2 minutes, and subsequently analyzed by XRPD.

The XRPD was compared to the XRPD prior to grinding. Upon grinding the reflections became a bit broader and an amorphous halo became visible. The grinded sample was stored at 95% RH for 1 week, and a following XRPD analysis showed that the reflections corresponded to the initial sample prior to grinding. Thus, the heptahydrate regained crystallinity after storage.

DH1 of Compound (Id)

A sample of the DH1 of compound (Id) was grinded by hand using mortar and pestle for 2 minutes, and a sample was pressured with 300 PSI for 5 minutes.

Subsequently, the sample was analysed by XRPD. The XRPD after the treatments did not show sign of decreased crystallinity compared to the XRPD of the initial sample prior to grinding and pressure testing.

Further, another sample of the DH1 of compound (Id) was milled. XRPD of the milled sample compared with un-milled material did not show any difference in the XRPD pattern. Thus comparison of the XRPDs showed that there was no apparent change in crystallinity of the DH1 sample.

It is therefore concluded that the DH1 of compound (Id) is very stable towards physical stress.

Potassium Salt of Compound (Id)

Samples of the $K^+$ salt form as described in Table 2 of Example 3 were either grinded with mortar and pestle or pressed in an IR-press for 5 minutes. The samples were analysed by XRPD after the treatment. Subsequently, the samples were placed at 95% RH for 1 week and reanalysed by XRPD.

Results: Grinding lead to severe broadening of the XRPD reflections, but the subsequent exposure to high humidity lead to the sharp reflections again. Exposure to high pressure does also lead to some broadening of the XRPD reflections although to a less extent than grinding. The sharp reflections are regained by exposure to humidity, Thus, the $K^+$ salt form regained crystallinity after storage at high humidity.

In conclusion, the DVS and grinding studies of the present example showed that the dihydrate of the zwitterion of compound (Id) was the most stable solid form, since it is non-hygroscopic and also was found to be stable when tested after grinding and pressure.

Examples 6 to 10: In Vitro and In Vivo Characterization of Compound (Id)

Example 6a: Conversion of the Compound of Formula (Id) in Rat and Human Hepatocytes Compound (Id) was incubated at 1 µg/mL with hepatocytes from human or rat suspended in DMEM (Dulbecco's Modified Eagle Medium) with HEPES (4-(2-hydroxyethyl)-1-piperazineethanesulfonic acid) at pH 7.4. The cell concentration at incubation was $1 \times 10^6$ viable cells/mL. The incubations were performed in glass tubes at 37° C. with a total incubation volume of 3.5 mL and with duplicate incubations for each test item. The 3.5 mL of hepatocyte suspension was equilibrated for 10 minutes in a water bath set to 37° C. where after the incubations were initiated by adding 3.5 µL of a stock solution of the test item in DMSO (Dimethyl sulfoxide) and gently inverting the tubes. The final solvent concentration in the incubations was 0.1% DMSO, Samples of 600 µL were withdrawn from the incubations at the pre-determined time points of 0.25, 5, 15, 30 and 60 minutes after ensuring homogeneity of hepatocyte suspensions. The withdrawn volume was added to 1 mL Nunc cryo tubes on wet ice containing 60 µL of ice-cold ascorbic acid (100 mg/mL) and 30 µL of ice cold 100 mM saccharic acid 1.4-lactone in 0.5 M citric acid. The tubes were mixed and 35 µL of a solution of ice cold 20% formic acid was added. The tubes were mixed thoroughly and stored at −80° C. awaiting analysis. Analysis method and Instrumentation used for analysis of (I) from dosing compound (Id) was the one described in Examples 9 and 10 below in the section "Instrumentation used for analysis of compound (I) from dosing of compound (Ic) and (Id)."

FIG. 7 indicates a time dependent conversion to compound (I) from (Id) in both rat and human hepatocytes.

Example 6b: Conversion of the Compound of Formula (Id) in Fresh Rat and Human Blood Conversion of (Id) in human blood (average of 3 donors) and rat blood (average of 45 donors) to (I) was shown in fresh blood at 37° C. spiked with 1 µg/mL of (Id). (I) was measured at 0, 5, 15, 30 and 60 minutes in isolated plasma. Analysis method and Instrumentation as described in Examples 9 and 10 below in the section "Instrumentation used for analysis of compound (I) from dosing of compounds (Ic) and (Id)."

FIG. 8 indicates a time dependent conversion to compound (I) from (Id), in both rat and human blood.

Example 7: Dopamine Agonist Activity

Dopamine D1 Receptor Agonism

Dopamine D1 receptor agonism was measured using a HTRF cAMP from CisBio using the protocol developed by HD Biosciences (China). Briefly, the assay is a homogeneous time resolved-fluorescence resonance energy transfer (HTRF) assay that measures production of cAMP by cells in a competitive immunoassay between native cAMP produced by cells and cAMP-labeled with XL-665. A cryptate-labeled anti-cAMP antibody visualizes the tracer. The assay was performed in accordance with instructions from manufacturer.

Test compounds were added to wells of microplates (384 format). HEK-293 cells expressing the human D1 receptor were plated at 1000 cells/well and incubated 30 minutes at room temperature. cAMP-d2 tracer was added to wells and followed by addition of Anti-cAMP antibody-cryptate preparation and incubated for 1 hour at room temperature in dark. HTRF cAMP was measured by excitation of the donor with 337 nm laser (the "TRF light unit") and subsequent (delay time 100 microseconds) measurement of cryptate and d2 emission at 615 nm and 665 nm over a time window of 200 microseconds with a 2000 microseconds time window between repeats/100 flashes). HTRF measurements were performed on an Envision microplate reader (PerkinElmer). The HTRF signal was calculated as the emission-ratio at 665 nm over 615 nm. The HTRF ratio readout for test compounds was normalized to 0% and 100% stimulation using control wells with DMSO-solvent or 30 µM dopamine. Test compound potency ($EC_{50}$) was estimated by nonlinear regression using the sigmoidal dose-response (variable slope) using Xlfit 4 (IDBS, Guildford, Surrey, UK, model 205).

$$y=(A+((B-A)/(1+((C/x)^\wedge D))))$$

where y is the normalized HTRF ratio measurement for a given concentration of test compound, x is the concentration of test compound, A is the estimated efficacy at infinite compound dilution, and B is the maximal efficacy. C is the $EC_{50}$ value and D is the Hill slope coefficient. $EC_{50}$ estimates were obtained from an independent experiment and the logarithmic average was calculated.

Dopamine D2 Receptor Agonism

Dopamine D2 receptor agonism was measured using a calcium mobilization assay protocol developed by HD Biosciences (China). Briefly, HEK293/G15 cells expressing human D2 receptor were plated at a density of 15000 cells/well in clear-bottomed, Matrigel-coated 384-well plates and grown for 24 hours at 37° C. in the presence of 5% $CO_2$. The cells were incubated with calcium-sensitive fluorescent dye, Fluo8, for 60-90 minutes at 37° C. in the dark. Test compounds were prepared at 3-fold concentrated solution in 1×HBSS buffer with $Ca^{2+}$ and $Mg^{2+}$. Calcium Flux signal was immediately recorded after compounds were added from compound plate to cell plate at FLIPR (Molecular Devices). The fluorescence data were normalized to yield responses for no stimulation (buffer) and full stimulation (1 µM of dopamine) of 0% and 100% stimulation, respectively. Test compound potency ($EC_{50}$) was estimated by nonlinear regression using the sigmoidal dose-response (variable slope) using Xlfit 4 (IDBS, Guildford, Surrey, UK, model 205).

$$y = (A + ((B-A)/(1+((C/x)^D))))$$

where y is the normalized ratio measurement for a given concentration of test compound, x is the concentration of test compound, A is the estimated efficacy at infinite compound dilution, and B is the maximal efficacy. C is the $EC_{50}$ value and D is the Hill slope coefficient. $EC_{50}$ estimates were obtained from independent experiment and the logarithmic average was calculated.

Example 8: 5-HT2B Agonist Activity and Binding Assay

5-HT2B Agonist Activity Assay

Evaluation of the agonist activity of compounds (I), (Ia) and (Ib) at the human 5-HT2B receptor was performed by Eurofins/Cerep (France) measuring the compound effects on inositol monophosphate (IP1) production using the HTRF detection method. Briefly, the human 5-HT2B receptor was expressed in transfected CHO cells. The cells were suspended in a buffer containing 10 mM Hepes/NaOH (pH 7.4), 4.2 mM KCl, 146 mM NaCl, 1 mM CaCl2, 0.5 mM MgCl2, 5.5 mM glucose and 50 mM LiCl, then distributed in microplates at a density of 4100 cells/well and incubated for 30 minutes at 37° C. in the presence of buffer (basal control), test compound or reference agonist. For stimulated control measurement, separate assay wells contained 1 µM 5-HT. Following incubation, the cells were lysed and the fluorescence acceptor (fluorophen 02-labeled IP1) and fluorescence donor (anti-IP1 antibody labeled with europium cryptate) were added. After 60 minutes at room temperature, the fluorescence transfer was measured at lambda(Ex) 337 nm and lambda(Em) 620 and 665 nm using a microplate reader (Rubystar, BMG). The IP1 concentration was determined by dividing the signal measured at 665 nm by that measured at 620 nm (ratio). The results were expressed as a percent of the control response to 1 µM 5-HT. The standard reference agonist was 5-HT, which was tested in each experiment at several concentrations to generate a concentration-response curve from which its EC50 value is calculated as described above for dopamine functional assays.

5-HT2B Binding Assay

Evaluation of the affinity of compound (Id) for the human 5-HT2B receptor was determined in a radioligand binding assay at Eurofins/Cerep (France). Membrane homogenates prepared from CHO cells expressing the human 5HT2B receptor were incubated for 60 minutes at room temperature with 0.2 nM [125I](±)DOI (1-(4-iodo-2, 5-dimethoxyphenyl)propan-2-amine) in the absence or presence of the test compound in a buffer containing 50 mM Tris-HCl (pH 7.4), 5 mM $MgCl_2$, 10 µM pargyline and 0.1% ascorbic acid. Nonspecific binding is determined in the presence of 1 µM (±)DOI. Following incubation, the samples were filtered rapidly under vacuum through glass fiber filters (GF/B, Packard) presoaked with 0.3% polyethyleneimine (PEI) and rinsed several times with ice-cold 50 mM Tris-HCl using a 96-sample cell harvester (Unifilter, Packard). The filters were dried and counted for radioactivity in a scintillation counter (Topcount, Packard) using a scintillation cocktail (Microscint 0, Packard). The results are expressed as a percent inhibition of the control radioligand specific binding. The standard reference compound was (±)DOI, which was tested in each experiment at several concentrations to obtain a competition curve from which its $IC_{50}$ is calculated.

TABLE 7

In vitro activities for the compounds of formula (I), (Ia), (Ib), (Ic) and (Id) obtained according to Examples 7 and 8.

| | Compound | D1 $EC_{50}$ (nM)/ Emax | D2 $EC_{50}$ (nM)/ Emax | 5-HT2B $EC_{50}$ (nM)/ Emax |
|---|---|---|---|---|
| Parent compound | (I) | 3.3/99% | 1.3/91% | 2900 nM/50% |
| Prior art prodrugs | (Ia) | >1000 | >1000 | >6000 nM, 58% @30 µM |
| | (Ib) | >1000 | 46 nM/100% | 3.8 nM/79% |
| | (Ic) | nd | nd | −5% @10 µM |
| | (Id) | 2700/98% | 1100/92% | −25% @10 µM* |

*indicate binding affinity (% inhibition of control, specific binding at concentration indicated)
nd: not determined

Example 9: PK Experiments in Rats

For all the experiments, blood samples of approximately 0.68 mL were drawn from the tail or sublingual vein and put into K3EDTA tubes that had been pre-cooled and prepared with stabilizing solution consisting of 80 µL ascorbic acid and 40 µL 100 mM D-saccharic acid 1,4 lactone in water. The tubes were inverted gently 6-8 times to ensure thorough mixing and then placed in wet ice. The collecting tube was placed in wet ice for up to 30 minutes until centrifugation. Once removed from the wet ice the centrifugation was initiated immediately. Immediately after end of centrifugation the samples were returned to wet ice. Three sub-samples of 130 µL plasma were transferred to each of three appropriately labelled cryo tubes containing 6.5 µL pre-cooled formic acid (20%) (the tubes were pre-spiked and stored refrigerated prior to use). The tube lid was immediately replaced, and the plasma solution was thoroughly mixed by inverting gently 6-8 times. The samples were stored frozen at nominally −70° C. within 60 minutes after sampling. Centrifugation conditions at 3000 G for 10 minutes at 4° C. Plasma was placed on water-ice following collection. Final storage at approximately −70° C.

Plasma samples were analyzed by solid phase extraction or direct protein precipitation followed by UPLC-MS/MS. MS detection using electrospray in the positive ion mode with monitoring of specific mass-to-charge transitions for compound (I) using internal standards for correcting the response. The concentration-time data was analyzed, using standard software using appropriate noncompartmental techniques to obtain estimates of the derived PK parameters. Instrumentation Used for Analysis of Compound (I) from Dosing Compound (Ia):

Mass spectrometer (LC-MS/MS) Waters Acquity-Sciex API 5000. Analytical column Waters BEH FPLC Phenyl 100×2.1 mm column, 1.7 µm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring (multiple reaction monitoring) of test item and the added analytical standards Dosing and blood sampling: Han Wistar rats were supplied by Charles River Laboratories, Sulzfeld, Germany. An artificial, automatically controlled, light and dark cycle of 12 hours was maintained. The rats received a standard laboratory diet from Brogaarden (Altromin 1324 pellets). The rats had unrestricted access to the diet. During the study (a 4-week toxicity study) the rats received once daily doses of (Ia) orally by gavage. From rats given 300 µg/kg (Ia), blood samples) from 3 male satellite animals were collected on the following time points at Day 29: 0.5, 1, 2, 4, 6, 8, 12 and 24 hours after dosing.

Instrumentation Used for Analysis of Compound (I) from Dosing of Compound (Ib):

Mass spectrometer (LC-MS/MS) Waters Acquity-Sciex API 5000. Analytical column Waters BEH UPLC Phenyl 100×2.1 mm column, 1.7 µm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring of test item and the added analytical standards.

Dosing and blood sampling: Han Wistar rats were supplied by Charles River Laboratories, UK. An artificial, automatically controlled, light and dark cycle of 12 hours was maintained. The rats received a standard laboratory diet (Teklad 2014C Diet.). The rats had unrestricted access to the diet. During the study (a 26-week toxicity study) the rats received once daily doses of (Ib) orally by gavage. From rats given 300 µg/kg (Ib), blood samples from 3 male satellite animals were collected on the following time points at day 182: 0.5, 1, 2, 4, 8 and 24 hours after dosing.

Instrumentation Used for Analysis of Compound (I) from Dosing of Compounds (Ic) and (Id).

Mass spectrometer (LC-MS/MS) Waters Acquity—Waters Xevo TQ-S. Analytical column Acquity BEH O18 100×2.1 mm, 1.7 µm. Mobile phase A: 20 mM NH$_4$-Formate+0.2% formic acid. Mobile phase B: Acetonitrile+0.2% formic acid. Gradient run from 95/5% to 5/95% in 11.0 minutes. Flow rate 0.3 mL/min. MRM monitoring of test item and the added analytical standards.

Dosing and blood sampling for compound (Id): Han Wistar rats were supplied by Charles River Laboratories, Wiga GmbH, Germany. An artificial, automatically controlled, light and dark cycle of 12 hours was maintained. The rats received a standard laboratory diet from Brogaarden (Altromin 1324 pellets). The rats had unrestricted access to the diet, Male Han Wistar rats were dosed a single oral gavage administration of compound (Id) orally by gavage. Rats were given 633 µg/kg of compound (Id), blood samples from 3 male animals were collected on the following time points at Day 1: 1, 2, 4, 6, 8, and 24 hours after dosing.

Dosing and blood sampling for compound (Ic): Han Wistar rats were supplied by Envigo, UK. An artificial, automatically controlled, light and dark cycle of 12 hours was maintained. The rats received a standard laboratory diet Teklad 2014C. The rats had unrestricted access to the diet. Male Han Wistar rats were dosed a single oral gavage administration of (Ic), 494 µg/kg. Blood samples from 3 male animals were collected on the following time points at Day 1: 1, 2, 4, 6, 8, and 24 hours after dosing.

Instrumentation Used for Analysis of Apomorphine:

Mass spectrometer (UPCLC-MS/MS) Waters Acquity I-Class-Waters Xevo TQ-S. Analytical column Acquity HSS T3 C18 50×2.1 mm, 1.8 µm. Mobile phase A: 10 mM NH$_4$—Formate 0.2% formic acid:Acetonitril (95:5). Mobile phase B: 10 mM NH$_4$—Formate 0.2% formic acid:Acetonitril (5:95). Gradient run from 95/5% to 5/95% in 2.40 minutes. Flow rate 0.3 mL/min. MRM detection of test items and the added analytical standards.

Dosing and Blood Sampling for Apomorphine:

Animals for the study were as described in Example 10. Additionally, rats were administered a single dose of apomorphine subcutaneously. From rats administered 3000 µg/kg (apomorphine), blood samples from 3 male animals were collected on the following time points at Day 1: 0.25, 0.5, 1, 1½, 2, 3, 5 and 7 hours SC administration after dosing.

TABLE 8

PK parameters for (4aR,10aR)-1-Propyl-1,2,3,4,4a,5,10,10a-octahydro-benzo[g]quinoline-6,7-diol (compound (I)) after oral dosing of 0.300 mg/kg (Ia), 0.300 mg/kg (Ib), 0.633 mg/kg of (Id) and 494 µg/kg (Ic) to Wistar rats according to Example 9.

|  | compound | $T_{max}$ (h) | $C_{max}$ (pg/mL) | $AUC_{0-24}$ (pg*h/mL) | $t_{1/2}$ (h) | Exposure at 24 hours (pg/mL) |
|---|---|---|---|---|---|---|
| Prior art prodrugs | (Ia) | 1.0 | 3160 | 13600 | 4.09 | 48 ± 26 |
|  | (Ib) | 1.0 | 4990 | 31000 | N/A | 147 ± 28 |
|  | (Ic) | 1.0 | 14 | 104 | N/A | N/A |
| Compound (Id) | (Id) | 4.0 | 1350 | 15500 | 6.8 | 208 ± 89 |

Example 10: PK/PD of Compound (Id)/Compound (I) in Rat Hyperactivity Assay

Animals

In total, 206 male CD rats (Charles River, Germany) weighing 200-250 grams (165-190 grams upon arrival) were used in the study. Animals were housed at a standard temperature (22±1° C.) and in a light-controlled environment (lights on from 7 am to 8 µm) with ad libitum access to food and water. The experiment described below was performed in accordance with the standard operating procedures of Charles River Discovery Research Services Finland Ltd. and in accordance with the national Animal Experiment Board of Finland (Eläinkoelautakunta, ELLA) authority on animal testing.

Locomotor Activity Testing, Open Field

The test device is a square Plexiglass-arena (measuring 40×40×40 cm), in which the movement paths of the rats are recorded by an activity monitor (Med. Associates Inc.). Before the test period is initiated, rats are habituated to their test cage for 60 minutes. Upon completion of habituation, animals were treated with either compound or vehicle and placed back into the open field apparatus. The main test parameter measured is ambulatory distance (recorded in 5-minute segments). Overall time of measurement after receiving initial treatment was 360 minutes, Total follow up period in the study was 420 min, including 60 min of habituation.

Results

Oral administration of compound (Id) was assessed in the rat locomotor activity assay, and this functional readout was then correlated to plasma concentrations of compound (I). Apomorphine and pramipexole were also concomitantly tested in this assay as comparators (i.e. known standard-of-care (SoC) in the Parkinson's Disease field), and plasma concentration was analyzed for apomorphine.

As shown in FIG. 2, compound (Id) (10 to 300 µg/kg, p.o.) increases locomotor activity with an effect starting approximately 2 hours' post-administration (around the 180-minute time point) and lasting until the end of recording (at the 415-minute time point). In contrary, the increased locomotor activity (hyperactivity) induced by apomorphine (3 mg/kg, s.c.) is immediate but short-lasting as the effect is gone 1.5 hours post administration (at the 150-minute time point).

Pramipexole (0.3 mg/kg, s.c.) also induces an increase in activity, but it's effect appears about 1 hour post administration and is gone 2.5 hours later (at the 270-minute time point). The total distance travelled as seen in FIG. 3 demonstrates a significantly increased activity for both compound (Id) and the two comparators tested, and this effect is the one that is to be expected from dopamine agonists.

In parallel with the locomotor activity assessment, plasma samples were taken from satellite animals at 6 different time points (1.5, 2, 3, 4, 5 & 7 hours) post-dose for animals treated with compound (Id)). Pharmacokinetic analysis demonstrates that the behavioral effects of compound (Id) (100 µg/kg, p.o.) correlate with the plasma concentrations of compound (I) (see FIG. 4), demonstrating that the behavioral effect of compound (Id) is driven by Compound (I) rather than by Compound (Id) itself. The corresponding exposure analysis of apomorphine administered subcutaneously (at 1.25, 1.5, 2, 3, 5 & 7 hours post-dose) resulted in a correlation between plasma concentrations of apomorphine and hyperactive behavior (see FIG. 5).

REFERENCE LIST

U.S. Pat. No. 4,543,256
WO2001/078713
WO 02/100377
WO2009/026934
WO2009/026935
WO2010/097092
WO2019101917
Alexander et Crutcher, (1990) Trends in Neuroscience 13: 266-71;
Bibbiani et al., Chase Experimental Neurology (2005), 192: 73-78;
Campbell et al., Neuropharmacology (1982); 21(10): 953-961;
Cannon et al., J. Heterocyclic Chem. (1980); 17: 1633-1636;
Cavero and Guillon, J. Pharmacol. Toxicol. Methods (2014), 69: 150-161;
Delong, (1990) Trends in Neuroscience 13: 281-5;
Gerfen et al, Science (1990) 250: 1429-32;
Giardina and Williams; CNS Drug Reviews (2001), Vol. 7 (3): 305-316;
Goswami et al., J. Nutritional Biochem. (2003) 14: 703-709;
Grosset et al., Acta Neurol Scand. (2013), 128:166-171;
Hauser et al., Movement Disorders (2016), Vol. 32 (9): 1367-1372;
Liu et al., J. Med. Chem. (2006), 49: 1494-1498;
Liu et al., Bioorganic Med. Chem. (2008), 16: 3438-3444;
Nolen et al., J. Pharm Sci. (1995), 84 (6): 677-681;
Poewe et al., Nature Review, (2017) vol 3 article 17013: 1-21;
Remington, "The Science and Practice of Pharmacy", 22th revised edition (2013), Edited by Allen; Loyd V., Jr.
Rothman et al., Circulation (2000), 102: 2836-2841;
Sprenger and Poewe, CNS Drugs (2013), 27: 259-272;
Sozio et al., Exp. Opin, Drug Disc. (2012); 7(5): 385-406;
Stain-Texier et al., Drug Metab. and Disposition (1998) 26 (5): 383-387;
Wiley-Interscience (publisher): Compendium of Organic Synthetic Methods, Vol. I-XII

The invention claimed is:

1. A solid form of the compound of formula (Id)

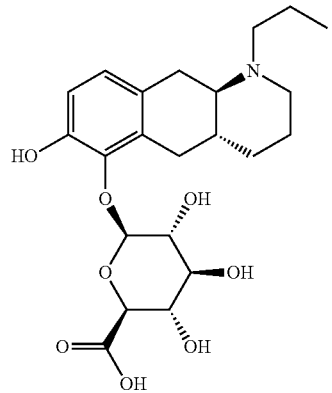

(Id)

wherein said solid form is selected from:
the group consisting of the dihydrate of the zwitterion of compound (Id), the heptahydrate of the zwitterion of compound (Id) and the potassium salt of the compound (Id).

2. The solid form according to claim 1, wherein said solid form is the dihydrate of the zwitterion of compound (Id) or the potassium salt of the compound (Id).

3. The solid form according to claim 1, wherein said solid form is the dihydrate characterized by an x-ray powder diffraction pattern as obtained using CuKα1 radiation (λ=1.5406 Å) comprising one or more XRPD peaks as listed for the dihydrate in Table 2, group (a).

4. The solid form according to claim 1, wherein said solid form is the dihydrate characterized by an x-ray powder diffraction pattern as obtained using CuKα1 radiation (λ=1.5406 Å) comprising peaks at the following 2θ-angles ±0.2° 2θ:10.4, 11.6, 12.3, 13.1, and 13.6°.

5. The solid form according to claim 4, wherein said x-ray powder diffraction pattern further comprises one or more peaks selected from the group consisting of peaks at the following 2θ-angles ±0.2° 2θ: 14.3, 15.6, 16.0, 16.8, and 18.5°.

6. The solid form according to claim 1, wherein said solid form is a crystal form characterized by an x-ray powder diffraction pattern as obtained using CuKα1 radiation (λ=1.5406 Å) essentially as depicted in FIG. 8a.

7. The solid form according to claim 1, said solid form exhibiting a weight loss of about 7.6% w/w compared to the initial weight when heated from about 30° C. to about 150° C. (heating rate 10° C./min).

8. The solid form according to claim 1, wherein said solid form is the potassium salt characterized by an x-ray powder diffraction pattern as obtained using CuKα1 radiation (λ=1.5406 Å) comprising one or more XRPD peaks as listed for the potassium salt in Table 2, group (a).

9. The solid form according to claim 8, wherein said potassium salt has a crystal form characterized by an XRPD obtained using CuKα1 radiation (λ=1.5406 Å) comprising peaks at the following 2θ-angles ±0.2° 2θ: 3.0, 9.0, 12.6, 13.6, and 15.0°.

10. The solid form according to claim 9, wherein said x-ray powder diffraction pattern further comprises one or more peaks selected from the group consisting of peaks at the following 2θ-angles ±0.2° 2θ: 17.1, 18.0, 18.4, 18.8 and 19.4°.

11. The solid form according to claim 1, said form exhibiting a weight loss of less than about 1% w/w compared to the initial weight when heated from about 20° C. to about 150° C. (heating rate 10° C/min).

12. A pharmaceutical composition comprising a therapeutically effective amount of the solid form of the compound of formula (Id) according to claim 1, and one or more pharmaceutically acceptable excipients.

13. A method for the manufacture of a medicament comprising combining the solid form of the compound of formula (Id) according to claim 1 with one or more pharmaceutically acceptable excipients.

14. The solid form according to claim 1, wherein said solid form is the dihydrate of the zwitterion of compound (Id).

15. The solid form according to claim 1, wherein said solid form is the heptahydrate of the zwitterion of compound (Id).

16. The solid form according to claim 1, wherein said solid form is the potassium salt of the compound (Id).

* * * * *